United States Patent
Liu et al.

(10) Patent No.: US 9,643,963 B2
(45) Date of Patent: May 9, 2017

(54) ANTIPARASITIC COMPOUNDS

(71) Applicant: Avista Pharma Solutions, Inc., Durham, NC (US)

(72) Inventors: Hao Liu, Raleigh, NC (US); Jessica Marie Sligar, Morrisville, NC (US); Jason Daniel Speake, Winston-Salem, NC (US); Joseph A. Moore, III, Wake Forest, NC (US); Brent Christopher Beck, Apex, NC (US)

(73) Assignee: Avista Pharma Solutions, Inc., Durham, NC (US)

( * ) Notice: Subject to any disclaimer, the term of this patent is extended or adjusted under 35 U.S.C. 154(b) by 0 days.

(21) Appl. No.: 15/036,335

(22) PCT Filed: Nov. 14, 2014

(86) PCT No.: PCT/US2014/065656
§ 371 (c)(1),
(2) Date: May 12, 2016

(87) PCT Pub. No.: WO2015/073797
PCT Pub. Date: May 21, 2015

(65) Prior Publication Data
US 2016/0280700 A1    Sep. 29, 2016

Related U.S. Application Data

(60) Provisional application No. 61/904,336, filed on Nov. 14, 2013.

(51) Int. Cl.
| | | |
|---|---|---|
| *C07D 213/02* | (2006.01) | |
| *C07D 417/04* | (2006.01) | |
| *A01N 43/82* | (2006.01) | |
| *A61K 45/06* | (2006.01) | |
| *A61K 31/4439* | (2006.01) | |
| *A61K 31/444* | (2006.01) | |
| *C07D 417/14* | (2006.01) | |
| *C07D 471/04* | (2006.01) | |
| *A01N 43/84* | (2006.01) | |
| *A01N 43/90* | (2006.01) | |
| *A01N 47/36* | (2006.01) | |
| *C07D 471/14* | (2006.01) | |

(52) U.S. Cl.
CPC .......... *C07D 417/04* (2013.01); *A01N 43/82* (2013.01); *A01N 43/84* (2013.01); *A01N 43/90* (2013.01); *A01N 47/36* (2013.01); *A61K 31/444* (2013.01); *A61K 31/4439* (2013.01); *A61K 45/06* (2013.01); *C07D 417/14* (2013.01); *C07D 471/04* (2013.01); *C07D 471/14* (2013.01)

(58) Field of Classification Search
CPC .................................................. C07D 213/02
USPC .......................................................... 546/255
See application file for complete search history.

(56) References Cited

U.S. PATENT DOCUMENTS

| 3,332,942 A | 7/1967 | Breivogel et al. |
|---|---|---|
| 5,756,523 A | 5/1998 | Heinemann et al. |
| 6,031,104 A | 2/2000 | Heinemann et al. |
| 8,273,772 B2 * | 9/2012 | Sutton .................. C07D 213/74 514/342 |
| 2008/0076771 A1 | 3/2008 | Reiter et al. |

FOREIGN PATENT DOCUMENTS

| WO | WO 02/100826 A2 | 12/2002 |
|---|---|---|
| WO | WO 2007/037543 A1 | 9/2007 |

OTHER PUBLICATIONS

International Search Report, mailed on Feb. 11, 2015, for PCT/US2014/065656 filed Nov. 14, 2014.
International Preliminary Report on Patentability, issued May 17, 2016, for PCT/US2014/065656 filed Nov. 14, 2014.

* cited by examiner

*Primary Examiner* — Niloofar Rahmani
(74) *Attorney, Agent, or Firm* — Brinks Gilson & Lione

(57) ABSTRACT

The invention relates to 1,2,4-thiadiazole derivatives and their use to treat parasites.

13 Claims, No Drawings

ANTIPARASITIC COMPOUNDS

This application is a National Stage application of International Application No. PCT/US2014/065656, filed Nov. 14, 2014, which claims the benefit of U.S. Provisional Application No. 61/904,336, filed Nov. 14, 2013, the entire contents of which are hereby incorporated herein by reference.

FIELD

Disclosed herein are 1,2,4-thiadiazole derivatives, compositions comprising them, processes for their preparation, intermediates useful in their synthesis, and their use as antiparasitic agents. In particular, the compounds of the invention are useful in the treatment or prevention of parasitic helminth infection.

BACKGROUND

There is an on-going need for new treatments for parasitic helminthic infection. Parasitic helminths (nematodes, trematodes, and cestodes) can cause many diseases and conditions of medical, veterinary, and agricultural importance. They can infect humans and other mammals, particularly companion animals such as dogs and cats as well as animals of agricultural importance such as sheep, cattle, horses, goats, fish, pigs, and poultry, causing many pathological effects and symptoms. These include, but are not limited to, malnutrition, weight loss, weakness, severe damage to tissues and organs of the infected host, elephantiasis, delayed intellectual development and other neurological effects, abdominal pain, anemia, stunting, insomnia, vomiting, diarrhoea, dermatitis, conjunctivitis, lymphangitis, meningitis, myocarditis, edema, asthma, and many others. These infections can be very debilitating and even fatal if left untreated. Parasitic nematodes can also infect plants, causing severe structural damage to roots, stems, leaves, and flowers, as well as opening a path for further infection by bacteria, fungi, and other nematodes, leading to crop damage and loss.

EP 455356 describes the preparation of 5-amino-1,2,4-thiadiazoles useful as immunosuppressants. International Patent Publication No. WO 2006/033005 discloses the preparation of oxazolyl, thiazolyl or thiadiazolyl pyrimidinylamino benzamide derivatives as thrombopoietin receptor agonists. WO2007/037543 discloses the preparation of biarylamide derivatives as inhibitors of metabotropic glutamate receptor 1 (mGluR1), WO2002/100826 discloses the preparation of 3,5-diaryl-1,2,4-oxadiazoles and analogs useful as activators of caspases and inducers of apoptosis. Journal of Medicinal Chemistry (2001), Vol. 44(5), 749-762 discloses thiazide and thiadiazole analogs as a novel class of adenosine receptor antagonists. Bioorganic & Medicinal Chemistry 21 (2013) 6385-6397 discloses structure activity relationships of 2-aminothiazoles effective against *mycobacterium tuberculosis*.

International Patent Publication No. WO1993/19054 discloses certain N-heterocyclic nitro anilines as fungicides, and refers to the use of these compounds to treat nematodes.

SUMMARY

In one aspect, provided herein are compounds of the formula (I):

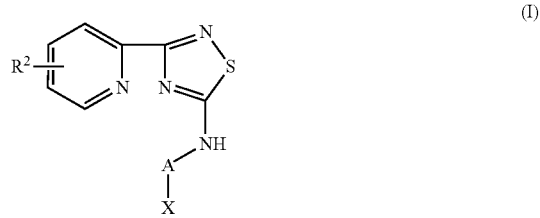

wherein:
A is C=O or $SO_2$;
X is $R^1$ Or $NHR^1$;
$R^1$ is:
phenyl optionally substituted by from one to three substituents which are the same or different, each selected from the group consisting of nitro, $-NR^3R^4$, cyano, $-NR^3COR^5$, alkyl, $-SO_2R^5$, $-NR^3SO_2R^5$, $-SO_2NR^3R^4$, $-CONR^3R^4$, $-CONHC_6H_5$, hydroxy, alkoxy, aryloxy, aryl, heterocyclyl, haloalkyl, haloalkoxy, mercapto (—SH), thioalkyl and halogen;
naphthyl optionally substituted by from one to three substituents which are the same or different, each selected from the group consisting of nitro, $-NR^3R^4$, cyano, $-NR^3COR^5$, -alkyl, $-SO_2R^5$, $-NR^3SO_2R^5$, $-SO_2NR^3R^4$, $-CONR^3R^4$, $-CONHC_6H_5$, hydroxy, alkoxy, aryloxy, aryl, heterocyclyl, haloalkyl, haloalkoxy, mercapto (—SH), thioalkyl and halogen;
quinoxolinyl optionally substituted by from one to three substituents which are the same or different, each selected from the group consisting of nitro, $-NR^3R^4$, cyano, $-NR^3COR^5$, alkyl, $-SO_2R^5$, $-NR^3SO_2R^5$, $-SO_2NR^3R^4$, $-CONR^3R^4$, $-CONHC_6H_5$, hydroxy, alkoxy, aryloxy, aryl, heterocyclyl, haloalkyl, haloalkoxy, mercapto (—SH), thioalkyl and halogen;
quinolyl optionally substituted by from one to three substituents which are the same or different, each selected from the group consisting of nitro, $-NR^3R^4$, cyano, $-NR^3COR^5$, $-CONHC_6H_5$, alkyl, $-SO_2R^5$, $-NR^3SO_2R^5$, $-SO_2NR^3R^4$, $-CONR^3R^4$, $-CONHC_6H_5$, hydroxy, alkoxy, aryloxy, aryl, heterocyclyl, haloalkyl, haloalkoxy, mercapto (—SH), thioalkyl and halogen;
or thionyl or furyl optionally substituted by from one to three substituents which are the same or different, each selected from the group consisting of nitro, $-NR^3R^4$, cyano, $-NR^3COR^5$, alkyl, $-SO_2R^5$, $-NR^3SO_2R^5$, $-SO_2NR^3R^4$, $-CONR^3R^4$, $-CONHC_6H_5$, hydroxy, alkoxy, aryloxy, aryl, heterocyclyl, haloalkyl, haloalkoxy, mercapto (—SH), thioalkyl and halogen;
$R^2$ is hydrogen, halogen, alkyl, alkoxy, haloalkyl, haloalkoxy, aminoalkyl, alkylaminoalkyl, aryl, heterocyclyl or $-CONR^3R^4$; or $R^2$, together with two adjacent carbon atoms of the pyridyl ring to which it is attached, forms a saturated or unsaturated ring containing from 4 to 6 ring atoms;
$R^3$ and $R^4$, which are the same or different, each represent hydrogen or alkyl; or when $R^3$ and $R^4$ are each attached to a nitrogen atom, they may form a saturated or unsaturated heterocyclic ring containing from 4 to 6 ring atoms;
$R^5$ is alkyl, haloalkyl;
or a pesticidally acceptable salt hereof.

In certain cases, the substituents $R^1$, $R^2$, $R^3$, $R^4$ and $R^5$ can contribute to optical and/or stereoisomerism. All such forms are encompassed by exemplary embodiments described herein.

In another aspect of the invention, provided are compositions comprising a compound of formula (I) along with a pesticidally acceptable excipient, carrier or diluent. The compositions of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

Also provided are compositions comprising a compound of formula (I) suitable for treatment of a locus that may be infected with parasites, such as a plant or animal, or for the prevention of infection of a locus with parasites.

In still another aspect of the present invention, there is provided a combination therapy whereby the compounds of formula (I) can be employed as such or in the form of their preparations (formulations) as combinations with other pesticidally active substances, such as, for example, insecticides, attractants, sterilants, nematicides, acaricides, fungicides, herbicides, and with safeners, fertilizers and/or growth regulators. The combinations may be part of the same formulation, or may be administered separately or sequentially to the locus.

In still another aspect, provided herein is a compound of formula (I), or a composition comprising a compound of formula (I), for use in treating or preventing parasitic infection.

In still another aspect, provided herein is the use of a compound of formula (I) for the manufacture of a medicament for use in treating or preventing parasitic infection.

In still another aspect, provided herein is a method of treating or preventing a parasitic infection comprising the administration of an effective amount of a compound of formula (I), or a composition comprising a compound of formula (I) to a locus.

DETAILED DESCRIPTION

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Definitions

When referring to the compounds and complexes disclosed herein, the following terms have the following meanings unless indicated otherwise.

"Alkoxy" where described in a substituent (e.g. 'alkoxy', 'haloalkoxy') refers to the group —OR where R is alkyl. This term is illustrated by the groups methoxy, ethoxy, n-propoxy, isopropoxy, n-butoxy, tert-butoxy, sec-butoxy, n-pentoxy, n-hexoxy and 1,2-dimethylbutoxy, cyclopentyloxy,cyclohexyloxy, 4-pyranyloxy.

"Alkyl" where described in a substituent (e.g. 'alkyl', 'haloalkyl', 'thioalkyl') refers to monovalent saturated aliphatic hydrocarbyl groups having from 1 to 20 carbon atoms, preferably 1-8 carbon atoms, preferably up to 6 (e.g. 1-6) carbon atoms. The hydrocarbon chain can be either straight-chained or branched. This term is illustrated by the groups methyl, ethyl, n-propyl, isopropyl, n-butyl, iso-butyl, and tert-butyl, cyclohexyl, cyclobutyl, cyclopentyl.

"Halogen" or "halo" where described in a substituent refers to a halogen, preferably Br, Cl or F.

"Heterocyclyl" refers to a saturated or unsaturated ring containing from 4 to 6 ring atoms and from 1 to 4 heteroatoms which may be the same or different selected from nitrogen, oxygen and sulphur, such as pyridyl, morpholino, piperidinyl, piperizinyl, pyrazolyl, tetrazolyl, oxazolyl, thiazolyl.

"Aryl" where described in a substituent (e.g. 'aryl', 'aryloxy') refers to a substituted or unsubstituted aromatic ring system of from 5 to 10 atoms, such as phenyl, naphthyl, 4-trifluoromethylphenyl.

A "saturated or unsaturated ring containing from 4 to 6 ring atoms" refers to a ring containing only carbon atoms, or a heterocyclic ring containing carbon atoms and non-carbon atoms (e.g. N).

"Pesticidally acceptable salt" refers to any salt of a compound disclosed herein which retains its biological properties and which is not toxic or otherwise undesirable for pesticidal use. Such salts may be derived from a variety of organic and inorganic counter-ions well known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, henzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only salts non-toxic organic or inorganic acids, such as halides, e.g., chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.21]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

It is to be understood that compounds having the same molecular formula but differing in the nature or sequence of bonding of their atoms or in the arrangement of their atoms in space are termed "isomers." Isomers that differ in the arrangement of their atoms in space are termed "stereoisomers."

Stereoisomers that are not minor images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds disclosed herein can possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, stereoisomers of the compounds provided herein are depicted upon treatment with base.

In certain embodiments, the compounds disclosed herein are "stereochemically pure". A stereochemically pure compound has a level of stereochemical purity that would be recognized as "pure" by those of skill in the art. Of course, this level of purity will be less than about 100%, In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" are used interchangeably herein. The terms "subject" and "subjects" refer to a primate (e.g., a monkey such as a cynomolgus monkey, a chimpanzee and a human) or non-primate animal. In one embodiment, the subject is a human. In another embodiment, the subject is a companion animal such as a dog or cat. In a further embodiment the subject is an animal of agricultural importance such as a sheep, cow, horse, goat, fish, pig, or domestic fowl (such as a chicken, turkey, duck or goose).

Compounds

In one embodiment there are provided compounds of formula (I) wherein:
A is C=O or $SO_2$;
X is $R^1$ or $NHR^1$;
$R^1$ is:
phenyl optionally substituted by from one to three substituents which are the same or different, each selected from the group consisting of nitro, $-NR^3R^4$, cyano, $-NR^3COR^5$, alkyl, $-SO_2R^5$, $-NR^3SO_2R^5$, $-SO_2NR^3R^4$, $-CONR^3R^4$, $-CONHC_6H_5$, hydroxy, alkoxy, haloalkyl, haloalkoxy, mercapto (—SH), thioalkyl and halogen;

naphthyl optionally substituted by from one to three substituents which are the same or different, each selected from the group consisting of nitro, $-NR^3R^4$, cyano, $-NR^3COR^5$, -alkyl, $-SO_2R^5$, $-NR^3SO_2R^5$, $-SO_2NR^3R^4$, $-CONR^3R^4$, $-CONHC_6H_5$, hydroxy, alkoxy, haloalkyl, haloalkoxy, mercapto (—SH), thioalkyl and halogen;

quinoxolinyl optionally substituted by from one to three substituents which are the same or different, each selected from the group consisting of nitro, $-NR^3R^4$, cyano, $-NR^3COR^5$, alkyl, $-SO_2R^5$, $-NR^3SO_2R^5$, $-SO_2NR^3R^4$, $-CONR^3R^4$, $-CONHC_6H_5$, hydroxy, alkoxy, haloalkyl, haloalkoxy, mercapto (—SH), thioalkyl and halogen;

quinolyl optionally substituted by from one to three substituents which are the same or different, each selected from the group consisting of nitro, $-NR^3R^4$, cyano, $-NR^3COR^5$, $-CONHC_6H_5$, alkyl, $-SO_2R^5$, $-NR^3SO_2R^5$, $-SO_2NR^3R^4$, $-CONR^3R^4$, $-CONHC_6H_5$, hydroxy, alkoxy, haloalkyl, haloalkoxy, mercapto (—SH), thioalkyl and halogen;

$R^2$ is hydrogen, halogen, alkyl, alkoxy, haloalkyl or haloalkoxy; or $R^2$, together with two adjacent carbon atoms of the pyridyl ring to which it is attached, forms a saturated or unsaturated ring containing from 4 to 6 ring atoms;

$R^3$ and $R^4$, which are the same or different, each represent hydrogen or alkyl;

and $R^5$ is alkyl.

In one embodiment, A is C=O. In another embodiment, A is $SO_2$.

In one embodiment X is $-NHR^1$. In a further embodiment, X is $R^1$.

In another embodiment, $R^1$ is phenyl optionally substituted by from one to three substituents which are the same or different selected from the group consisting of trifluoromethyl, trifluoromethoxy, halogen, methyl, ethyl, methoxy, ethoxy, thiomethyl, $-SO_2CH_3$, $-SO_2NH_2$, $-SO_2NHCH_3$, $-SO_2N(CH_3)_2$ and $-NHSO_2CH_3$.

In a further embodiment, $R^1$ is phenyl substituted by from 1 to 3 substituents which are the same or different selected from the group consisting of halogen, cyano, haloalkyl, alkoxy and haloalkoxy; $R^1$ is naphthyl optionally substituted by from 1 to 3 substituents which are the same or different selected from the group consisting of halogen, cyano, haloalkyl, alkoxy and haloalkoxy.

In a further embodiment $R^2$ is hydrogen or halogen. In yet a further embodiment $R^2$ is hydrogen.

In each of the emboditnents discussed above, A, X, $R^1$ and $R^2$ can be independently selected with respect to the A, X, $R^1$, $R^2$, $R^3$, $R^4$ and $R^5$ substituents, respectively.

In yet a further embodiment, there are provided compounds of formula (I) in which:
A is C=O;
X is $NHR^1$;
$R^1$ is phenyl optionally substituted by from one to three substituents which are the same or different selected from the group consisting of trifluoromethyl, trifluoromethoxy, halogen (e.g. chloro or fluoro), cyano, methyl, ethyl, methoxy, ethoxy, thiomethyl, $-SO_2CH_3$, $-SO_2NH_2$, $-SO_2NHCH_3$, $-SO_2N(CH_3)_2$ and $-NHSO_2CH_3$; and $R^2$ is hydrogen, fluoro, methyl, trifluoromethyl, methoxy or trifluoromethoxy.

In yet a further embodiment, there are provided compounds of formula (I) in which:

A is C=O;
X is $R^1$;
$R^1$ is phenyl substituted by from one to three substituents which are the same or different selected from the group consisting of trifluoromethyl, trifluoromethoxy, chloro, fluoro, cyano, methyl, ethyl, methoxy, ethoxy, aryloxy, thiomethyl, —SO$_2$CH$_3$, —SO$_2$NH$_2$, —SO$_2$NHCH$_3$, —SO$_2$N(CH$_3$)$_2$ and —NHSO$_2$CH$_3$; and
$R^2$ is hydrogen, fluoro, methyl, trifluoromethyl, methoxy, trifluoromethoxy, morpholino, aminoalkyl dimethylaminomethyl.

In yet a further embodiment, there are provided compounds of formula (I) in which:

A is SO$_2$;
X is $R^1$;
$R^1$ is phenyl substituted by from one to three substituents which are the same or different selected from the group consisting of trifluoromethyl, trifluoromethoxy, chloro, fluoro, cyano, methyl, ethyl, methoxy, ethoxy, thiomethyl, methanesulfonyl, sulfonamide, methylsulfonamide, dimethylsulfonamide, and methylsulfonanilide; and
$R^2$ is hydrogen.

In yet a further embodiment there are provided compounds of formula wherein:

A is C=O or SO$_2$;
X is $R^1$ or NHR$^1$;
$R^1$ is:
phenyl optionally substituted by from one to three substituents which are the same or different, each selected from the group consisting of nitro, —NR$^3$R$^4$, cyano, —NR$^3$COR$^5$, alkyl, alkoxy, aryl, helerocyclyl, aryloxy, haloalkyl, haloalkoxy, mercapto (—SH), thioalkyl and halogen;
$R^2$ is hydrogen, fluoro, methyl, trifluoromethyl, methoxy, trifluoromethoxy, morpholino, aminoalkyl or dimethylaminomethyl.

In one embodiment, the compounds of formula (I) provided herein are selected from the following compounds ("Cpd" means Compound) of Table 1:

TABLE 1

| Cpd | Name |
|---|---|
| 1 | 1-(4-methoxyphenyl)-3-[3-(2-pyridyl)-1,2,4-thiadiazol-5-yl]urea |
| 2 | 1-(2-chlorophenyl)-3-[3-(2-pyridyl)-1,2,4-thiadiazol-5-yl]urea |
| 3 | 1-[3-(2-pyridyl)-1,2,4-thiadiazol-5-yl]-3-[4-(trifluoromethyl)phenyl]urea |
| 4 | 1-(4-methoxyphenyl)-3-[3-(2-pyridyl)-1,2,4-thiadiazol-5-yl]urea |
| 5 | 1-[3-(2-pyridyl)-1,2,4-thiadiazol-5-yl]-3-[4-(trifluoromethoxy)phenyl]urea |
| 6 | 1-[3-(2-pyridyl)-1,2,4-thiadiazol-5-yl]-3-[3-(trifluoromethyl)phenyl]urea |
| 7 | 4-chloro-N-[3-(2-pyridyl)-1,2,4-thiadiazol-5-yl]benzamide |
| 8 | 3-chloro-N-[3-(2-pyridyl)-1,2,4-thiadiazol-5-yl]benzamide |
| 9 | 4-cyano-N-[3-(2-pyridyl)-1,2,4-thiadiazol-5-yl]benzamide |
| 10 | 3-fluoro-N-[3-(2-pyridyl)-1,2,4-thiadiazol-5-yl]benzamide |
| 11 | N-[3-(2-pyridyl)-1,2,4-thiadiazol-5-yl]-4-(trifluoromethyl)benzamide |
| 12 | N-[3-(2-pyridyl)-1,2,4-thiadiazol-5-yl]naphthalene-2-carboxamide |
| 13 | 4-trifluoromethoxy-N-[3-(2-pyridyl)-1,2,4-thiadiazol-5-yl]benzamide |
| 14 | 4-chloro-N-[3-(2-pyridyl)-1,2,4-thiadiazol-5-yl]benzenesulfonamide |
| 15 | 2-chloro-N-[3-(2-pyridyl)-1,2,4-thiadiazol-5-yl]benzenesulfonamide |
| 16 | 4-cyano-N-[3-(2-pyridyl)-1,2,4-thiadiazol-5-yl]benzenesulfonamide |
| 17 | 4-methoxy-N-[3-(2-pyridyl)-1,2,4-thiadiazol-5-yl]benzenesulfonamide |
| 18 | 2-methoxy-N-[3-(2-pyridyl)-1,2,4-thiadiazol-5-yl]benzenesulfonamide |
| 19 | N-[3-(2-pyridyl)-1,2,4-thiadiazol-5-yl]-3-(trifluoromethyl)benzenesulfonamide |
| 20 | N-[3-(2-pyridyl)-1,2,4-thiadiazol-5-yl]-4-(trifluoromethyl)benzenesulfonamide |
| 21 | N-[3-(3-fluoro-2-pyridyl)-1,2,4-thiadiazol-5-yl]-4-(trifluoromethyl)benzamide |
| 22 | N-[3-(4-morpholino-2-pyridyl)-1,2,4-thiadiazol-5-yl]-4-(trifluoromethyl)benzamide |
| 23 | N-[3-[4-[benzyl(methyl)amino]-2-pyridyl]-1,2,4-thiadiazol-5-yl]-4-(trifluoromethyl)benzamide |
| 24 | N-[3-[4-(dimethylamino)-2-pyridyl]-1,2,4-thiadiazol-5-yl]-4-(trifluoromethyl)benzamide |
| 25 | N-[3-[4-[2-methoxyethyl(methyl)amino]-2-pyridyl]-1,2,4-thiadiazol-5-yl]-4-(trifluoromethyl)benzamide |
| 26 | N-[3-(5-methoxy-2-pyridyl)-1,2,4-thiadiazol-5-yl]-4-(trifluoromethyl)benzamide |
| 27 | N-[3-(4-methoxy-2-pyridyl)-1,2,4-thiadiazol-5-yl]-4-(trifluoromethyl)benzamide |
| 28 | N-[3-[4-(triazolo[4,5-b]pyridin-3-yloxy)-2-pyridyl]-1,2,4-thiadiazol-5-yl]-4-(trifluoromethyl)benzamide |
| 29 | N-[3-(5-bromo-2-pyridyl)-1,2,4-thiadiazol-5-yl]-4-(trifluoromethyl)benzamide |
| 30 | methyl 2-[5-[[4-(trifluoromethyl)benzoyl]amino]-1,2,4-thiadiazol-3-yl]pyridine-4-carboxylate |
| 31 | N-[3-(2-pyridyl)-1,2,4-thiadiazol-5-yl]isoquinoline-7-carboxamide |
| 32 | 4-acetamido-N-[3-(2-pyridyl)-1,2,4-thiadiazol-5-yl]benzamide |
| 33 | 4-fluoro-N-[3-(2-pyridyl)-1,2,4-thiadiazol-5-yl]benzamide |
| 34 | 4-nitro-N-[3-(2-pyridyl)-1,2,4-thiadiazol-5-yl]benzamide |
| 35 | N-[3-(2-pyridyl)-1,2,4-thiadiazol-5-yl]quinoxaline-6-carboxamide |
| 36 | N-[3-(2-pyridyl)-1,2,4-thiadiazol-5-yl]thiophene-2-carboxamide |
| 37 | N-[3-(2-pyridyl)-1,2,4-thiadiazol-5-yl]thiophene-3-carboxamide |
| 38 | N-[3-(4-isopropyl-2-pyridyl)-1,2,4-thiadiazol-5-yl]-4-(trifluoromethyl)benzamide |
| 39 | N-[3-(3-isoquinolyl)-1,2,4-thiadiazol-5-yl]-4-(trifluoromethyl)benzamide |
| 40 | N-[3-(5-fluoro-2-pyridyl)-1,2,4-thiadiazol-5-yl]-4-(trifluoromethyl)benzamide |
| 41 | N-[3-(5-methyl-2-pyridyl)-1,2,4-thiadiazol-5-yl]-4-(trifluoromethyl)benzamide |
| 42 | 3-chloro-4-fluoro-N-[3-(5-fluoro-2-pyridyl)-1,2,4-thiadiazol-5-yl]benzamide |
| 43 | N-[3-(5-fluoro-2-pyridyl)-1,2,4-thiadiazol-5-yl]-4-(trifluoromethoxy)benzamide |
| 44 | 4-tert-butyl-N-[3-(5-fluoro-2-pyridyl)-1,2,4-thiadiazol-5-yl]benzamide |
| 45 | N-[3-(5-fluoro-2-pyridyl)-1,2,4-thiadiazol-5-yl]-3,5-bis(trifluoromethyl)benzamide |
| 46 | N-[3-(5-fluoro-2-pyridyl)-1,2,4-thiadiazol-5-yl]-3-(trifluoromethyl)benzamide |
| 47 | 3,4-dichloro-N-[3-(5-fluoro-2-pyridyl)-1,2,4-thiadiazol-5-yl]benzamide |
| 48 | 3-methylsulfonyl-N-[3-(2-pyridyl)-1,2,4-thiadiazol-5-yl]benzamide |
| 49 | N-[3-(2-pyridyl)-1,2,4-thiadiazol-5-yl]isoquinoline-5-carboxamide |
| 50 | 3-chloro-4-(4-methylpiperazin-1-yl)-N-[3-(2-pyridyl)-1,2,4-thiadiazol-5-yl]benzamide |
| 51 | methyl 4-[[3-(2-pyridyl)-1,2,4-thiadiazol-5-yl]carbamoyl]benzoate |
| 52 | 4-(diethylsulfamoyl)-N-[3-(2-pyridyl)-1,2,4-thiadiazol-5-yl]benzamide |
| 53 | 4-methyl-N-[3-(2-pyridyl)-1,2,4-thiadiazol-5-yl]thiophene-2-carboxamide |
| 54 | 3-chloro-4-fluoro-N-[3-(2-pyridyl)-1,2,4-thiadiazol-5-yl]benzamide |
| 55 | 2-fluoro-3-methoxy-N-[3-(2-pyridyl)-1,2,4-thiadiazol-5-yl]benzamide |
| 56 | N-[3-(2-pyridyl)-1,2,4-thiadiazol-5-yl]-3-(trifluoromethyl)benzamide |
| 57 | 2,5-dimethyl-N-[3-(2-pyridyl)-1,2,4-thiadiazol-5-yl]furan-3-carboxamide |
| 58 | 4-tert-butyl-N-[3-(2-pyridyl)-1,2,4-thiadiazol-5-yl]benzamide |
| 59 | N-[3-(2-pyridyl)-1,2,4-thiadiazol-5-yl]-1,3-benzodioxole-5-carboxamide |

TABLE 1-continued

| Cpd | Name |
|---|---|
| 60 | 3,4-dichloro-N-[3-(2-pyridyl)-1,2,4-thiadiazol-5-yl]benzamide |
| 61 | N-[3-(2-pyridyl)-1,2,4-thiadiazol-5-yl]-3,5-bis(trifluoromethyl)benzamide |
| 62 | 4-methoxy-N-[3-(2-pyridyl)-1,2,4-thiadiazol-5-yl]benzamide |
| 63 | 4-phenoxy-N-[3-(2-pyridyl)-1,2,4-thiadiazol-5-yl]benzamide |
| 64 | 4-fluoro-N-[3-(2-pyridyl)-1,2,4-thiadiazol-5-yl]-2-(trifluoromethyl)benzamide |
| 65 | N-[3-(2-pyridyl)-1,2,4-thiadiazol-5-yl]benzamide |
| 66 | 4-[[3-(2-pyridyl)-1,2,4-thiadiazol-5-yl]carbamoyl]benzoic acid |
| 67 | 4-iodo-N-[3-(2-pyridyl)-1,2,4-thiadiazol-5-yl]benzamide |
| 68 | 4-morpholino-N-[3-(2-pyridyl)-1,2,4-thiadiazol-5-yl]benzamide |
| 69 | 4-(morpholine-4-carbonyl)-N-[3-(2-pyridyl)-1,2,4-thiadiazol-5-yl]benzamide |
| 70 | tert-butyl 4-[4-[[3-(2-pyridyl)-1,2,4-thiadiazol-5-yl]carbamoyl]benzoyl]piperazine-1-carboxylate |
| 71 | tert-butyl 4-[[4-[[3-(2-pyridyl)-1,2,4-thiadiazol-5-yl]carbamoyl]benzoyl]amino]piperidine-1-carboxylate |
| 72 | 4-(piperidine-1-carbonyl)-N-[3-(2-pyridyl)-1,2,4-thiadiazol-5-yl]benzamide |
| 73 | 4-(piperazine-1-carbonyl)-N-[3-(2-pyridyl)-1,2,4-thiadiazol-5-yl]benzamide |
| 74 | N1-[3-(2-pyridyl)-1,2,4-thiadiazol-5-yl]terephthalamide |
| 75 | 4-(2-pyridylamino)-N-[3-(2-pyridyl)-1,2,4-thiadiazol-5-yl]benzamide |
| 76 | tert-butyl 4-[4-[[3-(2-pyridyl)-1,2,4-thiadiazol-5-yl]carbamoyl]anilino]piperidine-1-carboxylate |
| 77 | 4-phenyl-N-[3-(2-pyridyl)-1,2,4-thiadiazol-5-yl]benzamide |
| 78 | 4-piperazin-1-yl-N-[3-(2-pyridyl)-1,2,4-thiadiazol-5-yl]benzamide |
| 79 | 4-(4-piperidylamino)-N-[3-(2-pyridyl)-1,2,4-thiadiazol-5-yl]benzamide |
| 80 | tert-butyl 4-[4-[[3-(2-pyridyl)-1,2,4-thiadiazol-5-yl]carbamoyl]phenyl]piperazine-1-carboxylate |
| 81 | 3-chloro-2-fluoro-N-[3-(2-pyridyl)-1,2,4-thiadiazol-5-yl]-5-(trifluoromethyl)benzamide |
| 82 | N-[3-(2-pyridyl)-1,2,4-thiadiazol-5-yl]-4-(1,1,2,2-tetrafluoroethoxy)benzamide |
| 83 | 2-methoxy-N-[3-(2-pyridyl)-1,2,4-thiadiazol-5-yl]-4-(trifluoromethoxy)benzamide |
| 84 | N-[3-(2-pyridyl)-1,2,4-thiadiazol-5-yl]-5-(trifloromethyl)furan-2-carboxamide |
| 85 | N-[3-(2-pyridyl)-1,2,4-thiadiazol-5-yl]-5-(trifluoromethyl)thiophene-2-carboxamide |
| 86 | 4-formyl-N-[3-(2-pyridyl)-1,2,4-thiadiazol-5-yl]benzamide |
| 87 | 4-[hydroxy(phenyl)methyl]-N-[3-(2-pyridyl)-1,2,4-thiadiazol-5-yl]benzamide |
| 88 | 3-bromo-N-[3-(2-pyridyl)-1,2,4-thiadiazol-5-yl]benzamide |
| 89 | 4-benzyl-N-[3-(2-pyridyl)-1,2,4-thiadiazol-5-yl]benzamide |
| 90 | N4-[3-(2-pyridyl)-1,2,4-thiadiazol-5-yl]terephthalamide |
| 91 | 4-bromo-N-[3-(2-pyridyl)-1,2,4-thiadiazol-5-yl]benzamide |
| 92 | 3-chloro-N-[3-(2-pyridyl)-1,2,4-thiadiazol-5-yl]-4-(trifluoromethoxy)benzamide |
| 93 | N-[3-(4-phenyl-2-pyridyl)-1,2,4-thiadiazol-5-yl]-4-(trifluoromethyl)benzamide |
| 94 | 4-(trifluoromethyl)-N-[3-[5-(trifluoromethyl)-2-pyridyl]-1,2,4-thiadiazol-5-yl]benzamide |
| 95 | N4-phenyl-N1-[3-(2-pyridyl)-1,2,4-thiadiazol-5-yl]terephthalamide |
| 96 | N-[3-(2-pyridyl)-1,2,4-thiadiazol-5-yl]-2-(trifluoromethyl)benzamide |
| 97 | 2-fluoro-N-[3-(2-pyridyl)-1,2,4-thiadiazol-5-yl]-4-(trifluoromethoxy) benzamide |
| 98 | N-[3-(2-pyridyl)-1,2,4-thiadiazol-5-yl]-2-(trifluoromethoxy)benzamide |
| 99 | N-[3-(2-pyridyl)-1,2,4-thiadiazol-5-yl]-3-(trifluoromethoxy)benzamide |
| 100 | 4-(4-fluorophenoxy)-N-[3-(2-pyridyl)-1,2,4-thiadiazol-5-yl]benzamide |
| 101 | 3-hydroxy-N-[3-(2-pyridyl)-1,2,4-thiadiazol-5-yl]-5-(trifluoromethyl) thiophene-2-carboxamide |
| 102 | 4-(2,4-difluorophenoxy)-N-[3-(2-pyridyl)-1,2,4-thiadiazol-5-yl]benzamide |
| 103 | N-[3-(2-pyridyl)-1,2,4-thiadiazol-5-yl]-4-[4-(trifluoromethyl)phenoxy] benzamide |
| 104 | N-(3-(2-pyridyl)-1,2,4-thiadiazol-5-yl]-3-[4-(trifluoromethyl)phenoxy]benzamide |
| 105 | 3-(4-fluorophenoxy)-N-[3-(2-pyridyl)-1,2,4-thiadiazol-5-yl]benzamide |
| 106 | 3-phenoxy-N-[3-(2-pyridyl)-1,2,4-thiadiazol-5-yl]benzamide |
| 107 | N1-(4-piperidyl)-N4-[3-(2-pyridyl)-1,2,4-thiadiazol-5-yl]terephthalamide |
| 108 | N-[3-(5-piperazin-1-yl-2-pyridyl)-1,2,4-thiadiazol-5-yl]-4-(trifluoromethyl)benzamide |
| 109 | 4-(4-piperidyloxy)-N-[3-(2-pyridyl)-1,2,4-thiadiazol-5-yl]pyridine-2-carboxamide |
| 110 | N-[3-(6-piperazin-1-yl-2-pyridyl)-1,2,4-thiadiazol-5-yl]-4-(trifluoromethyl)benzamide |
| 111 | 4-(3-pyridyl)-N-[3-(2-pyridyl)-1,2,4-thiadiazol-5-yl] benzamide |
| 112 | N-[3-(5-phenyl-2-pyridyl)-1,2,4-thiadiazol-5-yl]-4-(trifluoromethyl)benzamide |
| 113 | 4-(trifluoromethyl)-N-[3-(5-vinyl-2-pyridyl)-1,2,4-thiadiazol-5-yl]benzamide |
| 114 | N-[3-[5-(3,6-dihydro-2H-pyran-4-yl)-2-pyridyl]-1,2,4-thiadiazol-5-yl]-4-(trifluoromethyl)benzamide |
| 115 | N-[3-(6-phenyl-2-pyridyl)-1,2,4-thiadiazol-5-yl]-4-(tifluoromethyl)benzamide |
| 116 | N-[3-[6-(3-pyridyl)-2-pyridyl]-1,2,4-thiadiazol-5-yl]-4-(trifluoromethyl)benzamide |
| 117 | 4-anilino-N-[3-(2-pyridyl)-1,2,4-thiadiazol-5-yl]benzamide |
| 118 | 4-(benzylamino)-N-[3-(2-pyridyl)-1,2,4-thiadiazol-5-yl]benzamide |
| 119 | 3-anilino-N-[3-(2-pyridyl)-1,2,4-thiadiazol-5-yl]benzamide |
| 120 | N-[3-[5-(3-pyridylamino)-2-pyridyl]-1,2,4-thiadiazol-5-yl]-4-(trifluoromethyl)benzamide |
| 121 | N-[3-(5-morpholino-2-pyridyl)-1,2,4-thiadiazol-5-yl]-4-(trifluoromethyl)benzamide |
| 122 | N-[3-[5-[2-methoxyethyl(methyl)amino]-2-pyridyl]-1,2,4-thiadiazol-5-yl]-4-(trifluoromethyl)benzamide |
| 123 | N-[3-(5-pyrrolidin-1-yl-2-pyridyl)-1,2,4-thiadiazol-5-yl]-4-(trifluoromethyl)benzamide |
| 124 | N-[3-[5-(2-pyridylamino)-2-pyridyl]-1,2,4-thiadiazol-5-yl]-4-(trifluoromethyl)benzamide |
| 125 | N-[3-[5-(4-methylpiperazin-1-yl)-2-pyridyl]-1,2,4-thiadiazol-5-yl]-4-(trifluoromethyl)benzamide |
| 126 | tert-butyl 4-[6-[5-[[4-(trifluoromethyl)benzoyl]amino]-1,2,4-thiadiazol-3-yl]-3-pyridyl]piperazine-1-carboxylate |
| 127 | N-[3-[5-(1-piperidyl)-2-pyridyl]-1,2,4-thiadiazol-5-yl]-4-(trifluoromethyl)benzamide |
| 128 | N-[3-(5-anilino-2-pyridyl)-1,2,4-thiadiazol-5-yl]-4-(trifluoromethyl)benzamide |
| 129 | N-[3-[5-(4-hydroxy-1-piperidyl)-2-pyridyl]-1,2,4-thiadiazol-5-yl]-4-(trifluoromethyl)benzamide |
| 130 | N-[3-[6-(4-methylpiperazin-1-yl)-2-pyridyl]-1,2,4-thiadiazol-5-yl]-4-(trifluoromethyl)benzamide |
| 131 | tert-butyl 4-[6-[5-[[4-(trifluoromethyl)benzoyl]amino]-1,2,4-thiadiazol-3-yl]-2-pyridyl]piperazine-1-carboxylate |
| 132 | N-[3-(4-Methyl-2-pyridyl)-1,2,4-thiadiazol-5-yl]-4-(trifluoromethyl)benzamide |
| 133 | N-[3-(6-Methyl-2-pyridyl)-1,2,4-thiadiazol-5-yl]-4-(trifluoromethyl)benzamide |
| 134 | N-[3-[4-(dimethylaminomethyl)-2-pyridyl]-1,2,4-thiadiazol-5-yl]-4-(trifluoromethyl)benzamide |
| 135 | N-[3-[4-[methyl-[2-(1-piperidyl)ethyl]amino]-2-pyridyl]-1,2,4-thiadiazol-5-yl]-4-(trifluoromethyl)benzamide |
| 136 | N-[3-[4-[methyl(2-morpholinoethyl)amino]-2-pyridyl]-1,2,4-thiadiazol-5-yl]-4-(trifluoromethyl)benzamide |
| 137 | N-[3-(4-pyrrolidin-1-yl-2-pyridyl)-1,2,4-thiadiazol-5-yl]-4-(trifluoromethyl)benzamide |
| 138 | N-[3-[4-(4-methylpiperazin-1-yl)-2-pyridyl]-1,2,4-thiadiazol-5-yl]-4-(trifluoromethyl)benzamide |
| 139 | N-[3-[4-[2-hydroxyethyl(methyl)amino]-2-pyridyl]-1,2,4-thiadiazol-5-yl]-4-(trifluoromethyl)benzamide |
| 140 | N-[3-[4-[2-(1-piperidyl)ethoxy]-2-pyridyl]-1,2,4-thiadiazol-5-yl]-4-(trifluoromethyl)benzamide |
| 141 | N-[3-[4-(2-methoxyethoxy)-2-pyridyl]-1,2,4-thiadiazol-5-yl]-4-(trifluoromethyl)benzamide |
| 142 | N-[3-[4-(2-dimethylaminoethyloxy)-2-pyridyl]-1,2,4-thiadiazol-5-yl]-4-(trifluoromethyl)benzamide |
| 143 | N-[3-[4-(2,2-dimethylpropoxy)-2-pyridyl]-1,2,4-thiadiazol-5-yl]-4-(trifluoromethyl)benzamide |
| 144 | N-[3-[4-[(1-methyl-4-piperidyl)oxy]-2-pyridyl]-1,2,4-thiadiazol-5-yl]-4-(trifluoromethyl)benzamide |

TABLE 1-continued

| Cpd | Name |
|---|---|
| 145 | N-[3-(4-tetrahydropyran-4-yloxy-2-pyridyl)-1,2,4-thiadiazol-5-yl]-4-(trifluoromethyl)benzamide |
| 146 | N-[3-[4-(oxetan-3-yloxy)--2-pyridyl]-1,2,4-thiadiazol-5-yl]-4-(trifluoromethyl)benzamide |
| 147 | N-[3-[4-(hydroxymethyl)-2-pyridyl]-1,2,4-thiadiazol-5-yl]-4-(trifluoromethyl)benzamide |

The Compound numbers 1 to 147 are used to identify the above compounds hereafter.

The compounds of formula (I) can be prepared, isolated or obtained by any method apparent to those of skill in the art. Exemplary methods of preparation are described in detail in the examples below.

In general, compounds of formula (I) in which X is $R^1$ can be prepared by the reaction of a compound of formula (II):

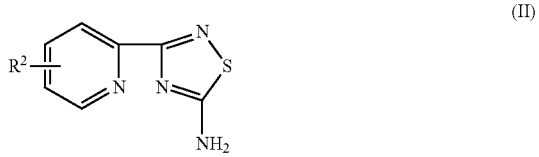

(II)

wherein $R^2$ is as defined above, with a compound of formula (III):

$R^1$-A-$X^1$    (III)

wherein $R^1$ and A are as defined above and $X^1$ is a leaving group. The reaction is generally carried out in an aprotic solvent (e.g. tetrahydrofuran) at a temperature from about 0 to about 100° C. In one embodiment, $X^1$ is a halogen, such as chlorine.

In another aspect compounds of formula (I) in which A is C═O and X is $NHR^1$ can be prepared by the reaction of a compound of formula (II) as defined above, with a compound of formula O═C═$NR^1$, wherein $R^1$ is as defined above. The reaction is generally carried out in an aprotic solvent (e.g. tetrahydrofuran) at a temperature from about 0 to about 100° C.

In another aspect compounds of formula (I) in which A is $SO_2$ and X is $NHR^1$ can be prepared by the reaction of a compound of formula (I) with a compound of formula $X^1SO_2NHR^1$, wherein $X^1$ and $R^1$ are as defined above.

Compounds of formula (II) above are known in the literature or can be prepared by known methods; see for example European Patent No. 455356. Compound of formula (III) above are known in the literature or can be prepared by known methods.

Compositions and Methods of Administration

The compounds of formula (I) used in the methods disclosed herein can be administered in certain embodiments using pesticidal compositions including at least one compound of general formula (I), if appropriate in the salt form, either used alone or in the form of a combination with one or more compatible and pesticidally acceptable carriers, such as diluents or adjuvants, or with another agent.

According to a further feature, there are provided compositions which comprise a thiadiazole derivative of formula (I) or a salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups or elixirs. Compositions intended for oral use can be prepared according to any method known in the art for the manufacture of pharmaceutical compositions and such compositions can contain one or more agents selected from the group consisting of sweetening agents, bittering agents, flavoring agents, coloring agents and preserving agents in order to provide pharmaceutically elegant and palatable preparations.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions can also contain sweetening agents, bittering agents, flavoring agents, and/or preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion.

The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents can be a naturally-occuring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such foramlations may also contain a demulcent, a preservative, flavoring agent(s) and/or coloring agent(s).

The compositions can be in the form of a sterile injectable aqueous or oleagenous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent of solvent, for example, as a solution in 1,3-butane diol. Among the acceptable vehicles and solvents that can be employed are water, Ringer's solution and isotonic sodium chloride solution. Cosolvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose any bland fixed oil can be employed including synthetic mono- or diglycerides. in addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention can be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations (formulations) as combinations with other pesticidally active substances, such as, for example, insecticides, attractants, sterilants, nematicides, acaricides, fungicides, herbicides, and with safeners, fertilizers and/or growth regulators.

The compounds of formula I according to the invention may be combined with one or more agents having the same sphere of activity e.g. to increase activity, or with substances having another sphere of activity e.g. to broaden the range of activity. It can also be sensible to add so-called repellents. By combining the compounds of the formula I with other suitable parasiticides not only the parasiticidal activity can be enhanced but the greatest part of those parasites that produce great economic damage will be covered. Moreover, this action will contribute substantially to avoiding the formation of resistance. Preferred groups of combination partners and especially preferred combination partners are named in the following, whereby combinations may contain one or more of these partners in addition to a compound of formula I. Suitable partners may also be afoxolaner, sarolaner, or fluralaner or a combination thereof. Any of the individually listed agents can be used in combination with compounds of formula (I) along with any other one or more listed agents independently.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broadband insecticides, broad-band acaricides and nematicides; and also the well known anthelminthics and insect- and/or acarid-deterring substances, said repellents or detachers. Non-limitative examples of suitable insecticides and acaricides are shown in the following table:

1. Abamectin 96. Dioxathion 191. Omethoate
2. Acephate 97. Disulfoton 192. Oxamyl
3. Acequinocyl 98. DNOC 193. Oxydemethon M
4. Acetamiprid 99. Doramectin 194. Oxydeprofos
5. Acetoprole 100. DPX-HGW86 195. Parathion
6. Acrinathrin 101. Edifenphos 196. Parathion-methyl
7. AKD-1022 102. Emamectin 197. Permethrin
8. Alanycarb 103. Empenthrin 198. Phenothrin
9. Aldicarb 104. Endosulfan 199. Phenthoate
10. Aldoxycarb 105. Esfenvalerat 200. Phorate
11. Allethrin 106. Ethiofencarb 201. Phosalone
12. Alpha-cypermethrin 107. Ethion 202. Phosmet
13. Alphamethrin 108. Ethiprole 203. Phosphamidon
14. Amidoflumet 109. Ethoprophos 204. Phoxim
15. Amitraz 110. Etofenprox 205. Pirimicarb
16. Anabasine 111. Etoxazole 206. Pirimiphos A
17. Avermectin B1 112. Etrimphos 207. Pirimiphos M
18. Azadirachtin 113. Fenamiphos 208. Polynactins
19. Azamethiphos 114. Fenazaquin 209. Prallethrin
20. Azinphos-ethyl 115. Fenbutatin oxid 210. Profenofos
21. Azinphos-methyl 116. Fenitrothion 211. Profluthrin
22. Azocyclotin 117. Fenobucarb 212. Promecarb
23. *Bacillus* subtil, toxin 118. Fenothiocarb 213. Propafos
24. *Bacillus thuringiensis* 119. Fenoxycarb 214. Propargite
25. Benclothiaz 120. Fenpropathrin 215. Propoxur
26. Bendiocarb 121. Fenpyroximate 216. Prothiofos
27. Benfuracarb 122. Fenthion 217. Prothoate
28. Bensultap 123. Fenvalerate 218. Protrifenbute
29. Benzoximate 124. Fipronil 219. Pymetrozine
30. Beta-cyfluthrin 125. Flonicamid 220. Pyrachlofos
31. Beta-cypermethrin 126. Fluacrypyrim 221. Pyrafluprole
32. Bifenazate 127. Fluazinam 222. Pyresmethrin
33. Bifenthrin 128 Fluazuron 223. Pyrethrin
34. Bioallethrin 129. Flubendiamide 224. Pyrethrum
35. Bioresmethrin 130. Flucycloxuron 225. Pyridaben
36. Bistrifluron 131. Flucythrinate 226. Pyridalyl
37. BPMC 132. Flufenerim 227. Pyridaphenthion
38. Brofenprox 133. Flufenoxuron 228. Pyrifluquinazon
39. Bromophos A 134. Flufenprox 229. Pyrimidifen
40. Bromopropylate 135. Flumethrin 230. Pyriprole
41. Bufencarb 136. Fonophos 231. Pyriproxyfen
42. Buprofezin 137. Formothion 232. Quinalphos
43. Butocarboxim 138. Fosthiazate 233. Resmethrin
44. Cadusafos 139. Fubfenprox 234. Rotenone
45. Carbaryl 140. Furathiocarb 235. RU 15525
46. Carbofuran 141. Gamma-cyhalothrin 236. Sabadilla
47. Carbophenothion 142. Halfenprox 237. Salithion
48. Carbosulfan 143. Halofenozide 238. Selamectin
49. Cartap 144. HCH 239. Silafluofen
50. Chloethocarb 145. Heptenophos 240. Spinetoram
51. Chlorantraniliprole 146. Hexaflumuron 241. Spinosad
52. Chlorethoxyfos 147. Hexythiazox 242. Spirodiclofen
53. Chlorfenapyr 148. Hydramethylnon 243. Spiromesifen
54. Chlorfenvinphos 149. Hydroprene 244. Spirotetramat
55. Chlorfluazuron 150. Imidacloprid 245. Sulcofuron sodium
56. Chlormephos 151. Imiprothrin 246. Sulfluramid
57. Chlorpyrifos 152. Indoxacarb 247. Sulfotep
58. Chlorpyrifos-methyl 153. insect-active fungi 248. Sulfur
59. Chromafenozide 154. insect-active 249. Sulprofos nematodes
60. Cis-Resmethrin 155. insect-active viruses 250. Taufluvalinate
61. Clofentezin 156. Iprobenfos 251. Tebufenozide
62. Clothianidin 157. Isofenphos 252. Tebufenpyrad
63. Coumaphos 158. lsoprocarb 253. Tebupirimfos
64. Cyanophos 159. Isoxathion 254. Teflubenzuron
65. Cycloprothrin 160. Ivermectin 255. Tefluthrin
66. Cyenopyrafen 161. Karanjin 256. Temephos
67. Cyflumetofen 162. Kinoprene 257. Terbufos
68. Cyfluthrin 163. Lamba-Cyhalothrin 258. Tetrachlorvinphos
69. Cyhalothrin 164. Lepimectin 259. Tetradifon
70. Cyhexatin 165. Lufenuron 260. Tetramethrin
71. Cymiazole 166. Malathion 261. Thiacloprid
72. Cypermethrin 167. Mecarbam 262. Thiamethoxam
73. Cyphenothrin 168. Mesulfenphos 263. Thiocyclam
74. Cyromazine 169. Metaflumizone 264. Thiodicarb
75. Deltamethrin 170. Metaldehyde 265. Thiofanox
76. Demeton M 171. Methamidophos 266. Thionazin
77. Demeton S 172. Methidathion 267. Thiosultap
78. Demeton-S-methyl 173. Methiocarb 268. Thuringiensin
79. Diafenthiuron 174. Methomyl 269. Tolfenpyrad
80. Diazinon 175. Methoprene 270. Tralomethrin
81. Dichlofenthion 176. Methothrin 271. Transfluthrin
82. Dichlorvos 177. Methoxyfenozide 272. Triarathene
83. Dicofol 178. Metofluthrin 273. Triazamate
84. Dicrotophos 179. Metolcarb 274. Triazophos
85. Dicyclanil 180. Metoxadiazone 275. Trichlorfon
86. Diethion 181. Mevinphos 276. Triflumuron
87. Diflovidazin 182. Milbemectin 277. Trimethacarb
88. Diflubenzuron 183. Milbemycin oxime 278. Vamidothion
89. Dimefluthrin 184. Monocrotophos 279. Vaniliprole
90. Dimethoate 185. Moxidectin 280. XMC (3,5,-Xylylmethylcarbamate)
91. Dimethylvinphos 186. Naled 281. Xylylcarb
92. Dinobuton 187. Nicotine 282. Zeta-cypermethrin
93. Dinocap 188. Nitenpyram 283. Zetamethrin
94. Dinotefuran 189. Novaluron 284. ZXI 8901 285. Afoxolaner 286. Sarolaner 287. fluralaner
95. Diofenolan 190. Noviflumuron Non-limitative examples of suitable anthelmintics are named in the following, a few representatives have anthelmintic activity in addition to the insecticidal and acaricidal activity.

Some of them are already listed above.

(A1) Abamectin (A2) Albendazole (A3) Cambendazole (A4) Closantel (A5) Diethylcarbamazine (A6) Doramectin (A7) Emodepside (A8) Eprinomectin (A9) Febantel (A10) Fendendazole (A11) Flubendazole (A12) Ivermectin
(A13) Levamisol (A14) Mebendazole (A15) Milbemectin
(A16) Milbemycin Oxime (A17) Morantel (A18) Moxidectin
(A19) Nitroscanate (A20) Omphalotin (A21) Oxantel
(A22) Oxfendazole (A23) Oxibendazole (A24) Phenothiazine
(A25) Piperazine (A26) PNU-97333 (A27) PNU-141962
(A28) Praziquantel (A29) Pyrantel (A30) Thiabendazole
(A31) Triclabendazole amino acetonitrile derivatives named in WO2005044784

Non-limitauve examples of suitable repellents and detachers are:
(R1) DEET (N, N-diethyl-m-toluamide)
(R2) KBR 3023 N-butyl-2-oxycarbonyl-(2-hydroxy)-piperidine (R3) Cymiazole=N,-2,3-dihydro-3-methyl-1,3-thiazol-2-ylidene-2,4-xylidene The above-specified combination partners are best known to specialists in this field. Most are described in various editions of the Pesticide Manual, The British Crop Protection Council, London, and others in the various editions of The Merck Index, Merck Co., inc., Rahway, N.J., USA or in patent literature. Therefore, the following listing is restricted to a few places where they may be found by way of example.

The commercially available compounds described in the table above can be found in The Pesticide Manual, 14th Ed. (2006), The British Crop Protection Council, London except for 99, 160, 183, 185, 238, A2, A6, A8, A9, A10, A12, A13, A16, A17. A18, A22, A23, A25, A28, A29, A30, which are described in the Compendium of Veterinary Products, 9th Ed. (2006), North American Compendiums, Inc,. Compounds Nos. 5, 7, 14, 66, 67, 100, 132, 163, 218, 221 228, 230, 240, 244, 268, and 279 can be found in the Internet, for example, in the online Merck Veterinary Manual and Compendium of Pesticide Common Names.

The pharmaceutical preparation comprising the thiadiazole derivatives, for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or prevention of a parasitic infection in a human or other mammal, the compounds utilized in the method of treatment are administered at an initial dosage of about 0.1 mg/kg to about 100 mg/kg per interval. Preferred intervals may be daily, weekly, monthly, quarterly, semi-annually, or annually. The dosages can be varied depending on the requirements of the patient, for example, the size of the human or mammal being treated, the severity of the condition being treated, the route of administration, and the potency of the compound being used. Determination of the proper dosage and route of administration for a particular situation is within the skill of the practitioner. Generally, the treatment will be initiated with smaller dosages which are less than the optimum dose of the compound, which can be increased in small increments until the optimum effect under the particular circumstances of the infection is reached. For convenience, the total daily dosage can be divided and administered in portions during the day if desired.

Methods of Treating Parasites

In one embodiment, there is provided a method of treating or preventing parasite infection in a subject, the method comprising administering to the subject an effective amount of thiadiazole derivative of formula (I) or a pesticidally acceptable salt thereof. In another embodiment there is provided the use of a thiadiazole derivative of formula (I) or a pesticidally acceptable salt thereof for treating or preventing parasite infection in a subject. In particular, the compounds of formula (I) are useful for the treatment or prophylaxis of parasitic helminth infections caused by nematodes, trematodes or cestodes, particularly in humans, companion animals, and veterinary animals, particularly dogs, cats, and agricultural livestock including cattle, sheep, goats, fish, pigs, equine and poultry. Such diseases include ascariasis, filariasis, loaiasis, onchocerciasis, schistosomiasis, trichinelliasis and hydatid disease.

The compounds of the invention are especially useful for the prophylaxis and/or treatment of lymphatic filariasis, subcutaneous filariasis, serous cavity filariasis, onchocerciasis (river blindness), elephantiasis, heartworm (dogs and cats), Verminous haemorrhagic dermatitis (cattle) and 'Summer bleeding' (horses).

Examples of parasitic nematodes include, but are not limited to, *Ostertagia lyrata, O. ostertagi, O. circumcincta, Cooperia oncophora, C. pectinata, C. punctata, C. surnabada, C. curtice a, Haemonchus contortus, H. placei, Trichostrongylus axei, T. colubriformis, T. vetrinus, Bunostomum phlebotomum, B. trigonocephalum, Oesophagostomum radiatum, O. dentatum, O. venulosum, O. columbianum, Strongyloides papiliosus, S. westeri, S. stercoralis, Nematodirus helvetianus, N. spathiger, N. filicolis, Trichuris* spp., *Strongylus vulgaris, S. edentatus, S. equinus, Triodontophorus* spp., *Oxyuris equ;, Parascaris equorum, Habronema muscae, Oncocerca* spp., *Dirofilaria immitis, Toxocara canis, Toxascaris leonina, Ancylostoma caninum, A. braziliense, A. duodenale, Thelazia* spp., *Uncinaria stenocephala, Chaberia ovina, Ascaris lumbricoides, Dictyocaulus vivaparus, D. arnfieldi, D. filaria, Brugia malayi, B. timori, Dioctophyma renare, Enterobius vermicularis, Loa loa, Mansonella ozzardi, M. perstans, M. streptocerca, Necator americanus, Onchocerca volvulus, Stronglyoides stercoralis, Trichinella spiralis, T. triciura* and *Wuchereria bancrofti*.

Examples of plant-damaging nematodes include, but are not limited to, the following genera: *Meloidogyne, Heterodera, Ditylenchus, Aphelenchoides, Radopholus, Globodera, Pratylenchus, longidorus* and *Xiphenema*.

Examples of parasitic cestodes include, but are not limited to: *Diphyllobothrium latum, D. Caninum, Echinococcus granulosus, E. multilocularis, Hymenolepsis diminuta, Taenia multiceps, T. saginatus, T. serialis, T. sohum* and *Vampirolepis nana*.

Examples of parasitic trematodes include, but are not limited to *Clonorchis sinensis, Dicrocoelium dendriticum, an echinostome, Fasciolopsis buski, Fasciola hepatica, a heterophyid, Nanophyetus salmincola, Opisthorchis felineus, O. viverrini, Paragonimus kellicotti P. westermani, Schistosoma haematobium, S. japonicum, S. mansoni, S. intercalatum* and *S. mekongi*.

SYNTHESIS

The following Examples illustrate the synthesis of representative compounds of formula (I). These examples are not intended, nor are they to be construed, as limiting the scope of the embodiments disclosed herein. It will be clear that various embodiments may be practiced otherwise than as particularly described herein. Numerous modifications and variations are possible in view of the teachings herein and, therefore, are within the scope.

Example 1

1-(4-methoxyphenyl)-3-[3-(2-pyridyl)-1,2,4-thiadiazol-5-yl]urea (Compound 1)

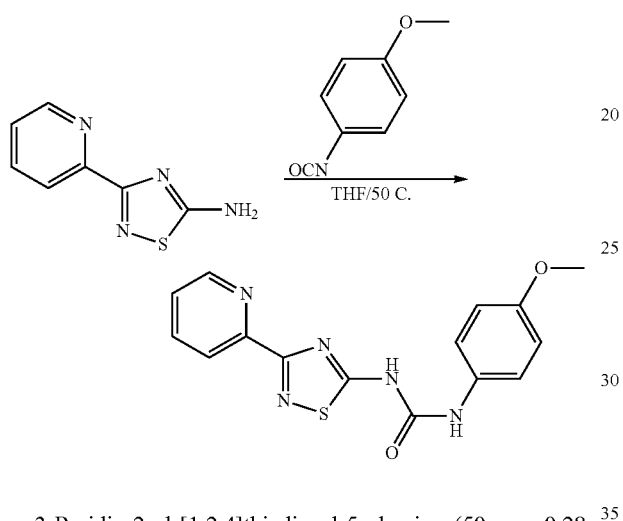

3-Pyridin-2-yl-[1,2,4]thiadiazol-5-ylamine (50 mg, 0.28 mmol) was dissolved in 1 mL of anhydrous tetrahydrofuran, to which solution was added p-methoxyphenyl isocyanate (36 µL, 0.28 mmol). The mixture was stirred at 50° C. overnight. Precipitation formed which was filtered and rinsed with methanol to yield a white solid (47.9 mg, 52%). $^1$H NMR (400 MHz, DMSO-$d_6$) δ ppm 3.74 (s, 3 H) 6.81-7.06 (m, 2 H) 7.32-7.46 (m, 2 H) 7.46-7.57 (m, 1 H) 7.83-8.06 (m, 1 H) 8.19 (d. J=7.86 Hz, 1 H) 8.60-8.90 (m, 1 H) 9.12 (s. 1 H) 11.49 (s, 1 H); LCMS (M/Z): M+H]$^+$328.

By proceeding in a similar manner, the following Compounds were also prepared:

Compound 2: 1-(2-chlorophenyl)-3-[3-(2-pyridyl)-1,2,4-thiadiazol-5-yl]urea

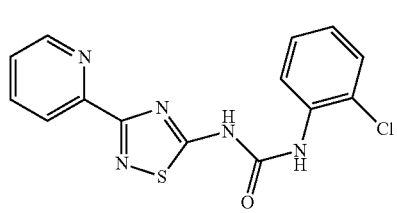 [SMILES: O=C(Nc1nc(-c2ccccn2)ns1)Nc1ccccc1Cl]

$^1$H NMR (400 MHz, DMSO-$d_6$) δ ppm 7.06-7.28 (m, 1 H) 7.30-7.46 (m, 1 H) 7.46-7.58 (m, 2 H) 7.91-8.04 (m, 1 H) 8.06-8.15 (m, 1 H) 8.20 (d, J=7.91 Hz, 1 H) 8.57-8.80 (m, 1 H) 8.91 (s, 1 H) 12.05 (s, 1 H); LCMS (M/Z): M+H]$^+$332.

Compound 3: 1-[3-(2-pyridyl)-1,2,4-thiadiazol-5-yl]-3-[4-(trifluoromethyl)phenyl]urea

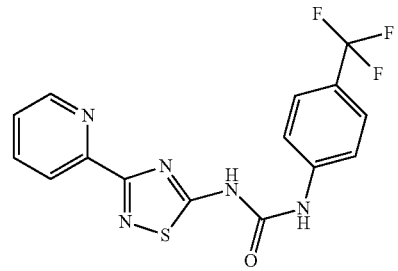 [SMILES: O=C(Nc1ccc(C(F)(F)F)cc1)Nc1nc(-c2ccccn2)ns1]

$^1$H NMR (400 MHz, DMSO-$d_6$) δ ppm 7.38-7.58 (m, 1 H) 7.65-7.87 (m, 4 H) 7.86-8.08 (m, 1 H) 8.20 (d, J=7.86 Hz, 1 H) 8.71 (d, J=3.95 Hz, 1 H) 9.73 (br. s., 1 H) 11.76 (s, 1 H); LCMS (M/Z): M+H]$^+$366.

Compound 4: 1-(3-methoxyphenyl)-3-[3-(2-pyridyl)-1,2,4-thiadiazol-5-yl]urea

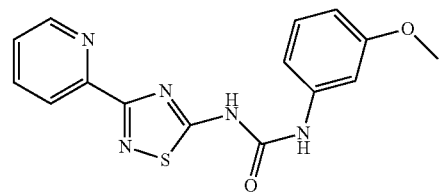 [SMILES: COc1cccc(NC(=O)Nc2nc(-c3ccccn3)ns2)c1]

$^1$H NMR (400 MHz, DMSO-$d_6$) δ ppm 3.76 (s, 3 H) 6.51-6.78 (m, 1 H) 7.06 (d, J=8.05 Hz, 1 H) 7.13-7.22 (m, 1 H) 7.26 (t, J=8.15 Hz, 1 H) 7.43-7.60 (m, 1 H) 7.83-8.10 (m, 1 H) 8.19 (d, J=7.86 Hz, 1 H) 8.59-8.82 (m, 1 H) 9.30 (s, 1 H) 11.52 (s, 1 H); LCMS (M/Z): M+H]$^+$328.

Compound 5: 1-[3-(2-pyridyl)-1,2,4-thiadiazol-5-yl]-3-[4-(trifluoromethoxy)phenyl]urea (as the hydrochloride salt)

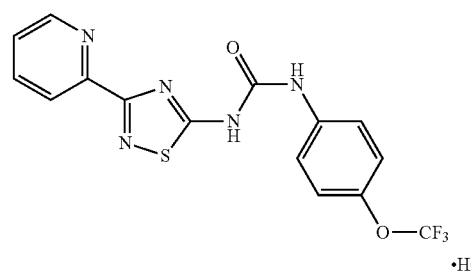

LCMS (M/Z): 382 (M+H). $^1$H NMR (400 MHz, DMSO-$d_6$) δ ppm 7.34 (d, J=8.59 Hz, 2 H) 7.52-7.69 (m, 3 H) 8.06 (t, J=7.42 Hz, 1 H) 8.24 (d, J=7.81 Hz, 1 H) 8.71 (d, J=4.49 Hz, 1 H) 9.88 (br. s., 1 H).

Compound 6: 1-[3-(2-pyridyl)-1,2,4-thiadiazol-5-yl]-3-[3-(trifluoromethyl)phenyl]urea

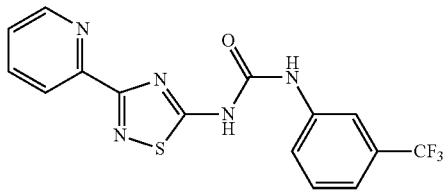 [SMILES: O=C(Nc1cccc(C(F)(F)F)c1)Nc1nc(-c2ccccn2)ns1]

LCMS (M/Z): 366 (M+H). ¹H NMR (400 MHz, DMSO-d₆) δ ppm 7.22(d, J=7.42 Hz, 1 H) 7.37-7.49 (m, 2 H) 7.77 (d, J=8.00 Hz, 1 H) 7.88 (t, J=7.42 Hz, 1 H) 8.07-8.21 (m, 2 H) 8.62 (d, J=3.71 Hz, 1 H).

Example 2

4-chloro-N-[3-(2-pyridyl)-1,2,4-thiadiazol-5-yl]benzamide (Compound 7)

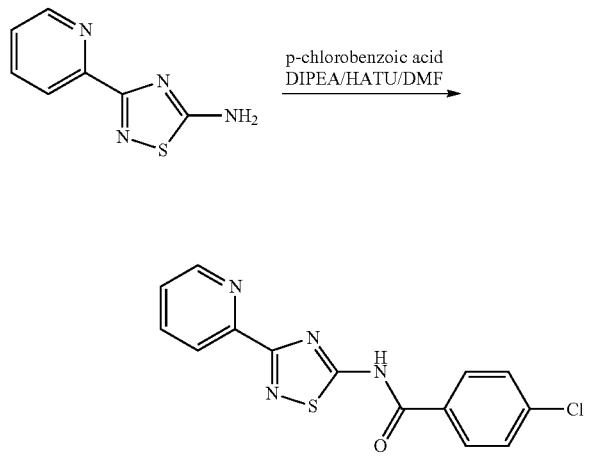

3-Pyridin-2-yl[1,2,4]thiadiazol-5-ylamine (50 mg, 0.28 mmol) and p-chlorobenzoic acid (44 mg, 0.28 mmol) were mixed in 1 mL of anhydrous dimethylformamide, to which solution was added N,N-diisopropylethylamine (0.1 mL, 0.58 mmol) followed by addition of 1-[bis(dimethylamino)methylene]-1H-1,2,3-triazolo[4,5-b]pyridinium 3-oxide hexafluorophosphate (114 mg, 0.30 mmol). The mixture was stirred under nitrogen at room temperature overnight. The reaction mixture was partitioned between ethyl acetate and water. The aqueous layer was extracted with ethyl acetate. The combined organic layer was dried over sodium sulfate, filtered and concentrated. The crude product was purified by flash chromatography to obtain Compound 7 as a white solid (53.5 mg, 60%). ¹H NMR (400 MHz, DMSO-d₆) δ ppm 7.36-7.64 (m, 1 H) 7.69 (d, J=8.69 Hz, 2 H) 7.91-8.10 (m, 1 H) 8.12-8.34 (m, 3 H) 8.72 (d, J=4.00 Hz, 1 H); LCMS (M/Z): M+H]⁺317.

By proceeding in a similar manner, the following Compounds were also prepared:

Compound 8: 3-chloro-N-[3-(2-pyridyl)-1,2,4-thiadiazol-5-yl]benzamide

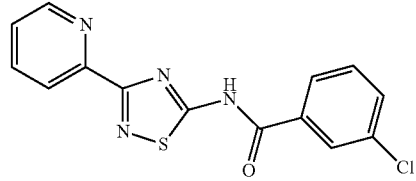 [SMILES: O=C(Nc1nc(-c2ccccn2)ns1)c1cccc(Cl)c1]

¹H NMR (400 MHz, DMSO-d₆) δ ppm 7.48-7.56 (m, 1 H) 7.60-7.68 (m, 1 H) 7.73-7.81 (m, 1 H) 7.95-8.08 (m, 1 H) 8.15 (d, J=8.30 Hz, 1 H) 8.20-8.31 (m, 2 H) 8.73 (d, J=3.95 Hz, 1 H); LCMS (M/Z): M+H]⁺317.

Compound 9: 4-cyano-N-[3-(2-pyridyl)-1,2,4-thiadiazol-5-yl]benzamide

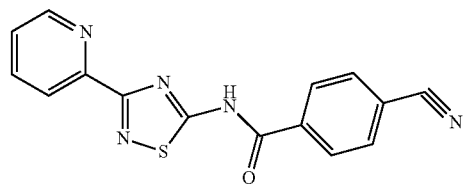 [SMILES: N#Cc1ccc(C(=O)Nc2nc(-c3ccccn3)ns2)cc1]

¹H NMR (400 MHz, DMSO-d₆) δ ppm 7.42-7.58 (m, 1 H) 7.87-8.05 (m, 2 H) 8.09 (d, J=8.54 Hz, 2 H) 8.25 (d, J=7.86 Hz, 1 H) 8.30-8.38 (m, 2 H) 8.68-8.77 (m, 1 H); LCMS (M/Z):M+H]³⁰ 308.

Compound 10: 3-fluoro-N-[3-(2-pyridyl)-thiadiazol-5-yl]benzamide

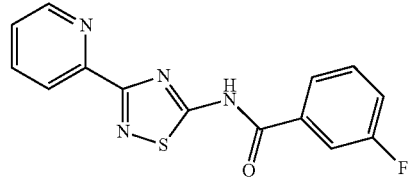 [SMILES: O=C(Nc1nc(-c2ccccn2)ns1)c1cccc(F)c1]

¹H NMR (400 MHz, DMSO-d₆) δ ppm 7.46-7.62 (m, 2 H) 7.62-7.75 (m, 1 H) 7.91-8.12 (m, 3 H) 8.25 (d, J=7.91 Hz, 1 H) 8.73 (d, J=4.00 Hz, 1 H) 13.89 (br. s., 1 H); LCMS (M/Z): M+H]⁺301.

Compound 11: N-[3-(2-pyridyl)-1,2,4-thiadiazol-5-yl]-4-(trifluoromethyl)benzamide

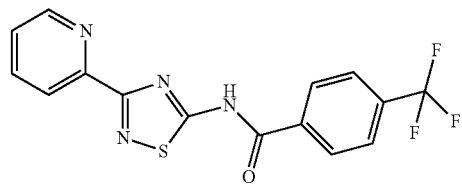 [SMILES: O=C(Nc1nc(-c2ccccn2)ns1)c1ccc(C(F)(F)F)cc1]

¹H NMR (400 MHz, DMSO-d₆) δ ppm 7.41-7.61 (m, 1 H) 7.97 (d, J=7.91 Hz, 3 H) 8.25 (d, J=7.86 Hz, 1 H) 8.38 (d, J=8.15 Hz, 2 H) 8.66-8.75 (m, 1 H); LCMS (M/Z): M+H]⁺ 351.

Compound 12: N-[3-(2-pyridyl)-1,2,4-thiadiazol-5-yl]naphthalene-2-carboxamide

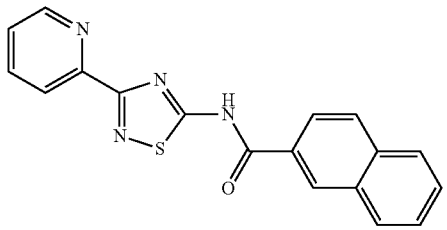 [SMILES: O=C(Nc1nc(-c2ccccn2)ns1)c1ccc2ccccc2c1]

¹H NMR (400 MHz, DMSO-d₆) δ ppm 7.48-7.57 (m, 1 H) 7.62-7.75 (m, 2 H) 7.96-8.03 (m, 1 H) 8.05 (d, J=7.81 Hz, 1 H) 8.11 (d, J=8.35 Hz, 2 H) 8.18-8.25 (m, 1 H) 8.27 (d, J=7.91 Hz, 1 H) 8.74 (d, J=3.95 Hz, 1 H) 8.92 (s, 1 H) 13.94 (br. s., 1 H); LCMS (M/Z): M+H]⁺333.

Compound 13: 4-trifluoromethoxy-N-[3-(2-pyridyl)-1,2,4-thiadiazol-5-]benzamide

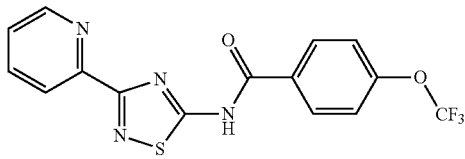 [SMILES: O=C(Nc1nc(-c2ccccn2)ns1)c1ccc(OC(F)(F)F)cc1]

LCMS (M/Z): 367 (M+H). ¹H NMR (400 MHz, acetone) δ ppm 7.45-7.52 (m, 2 H) 7.59 (d, J=8.40 Hz, 2 H) 7.95 (td, J=7.76, 1.66 Hz, 1 H) 8.11-8.19 (m, 1 H) 8.28 (d, J=7.81 Hz, 1 H) 8.43 (d, J=8.79 Hz, 2 H) 8.72 (d, J=4.30 Hz, 1 H).

Example 3

4-chloro-N-[3-(2-pyridyl)-1,2,4-thiadiazol-5-yl]benzenesulfonamide (Compound 14)

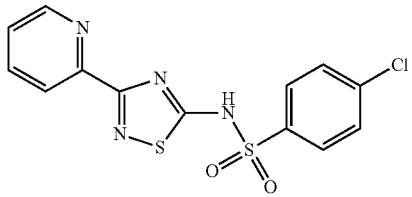 [SMILES: O=S(=O)(Nc1nc(-c2ccccn2)ns1)c1ccc(Cl)cc1]

3-(Pyridin-2-yl)-1,2,4-thiadiazol-5-amine (50 mg, 0.28 mmol) was dissolved in 1.5 mL pyridine. 4-Chlorobenzenesulfonyl chloride (65 mg, 0.31 mmol) was then added. The mixture was stirred for 16 hours at room temperature. The reaction was partitioned between dichloromethane and water. The aqueous layer was extracted with dichloromethane. The combined organic layer was dried over sodium sulfate, filtered and concentrated. The crude product was purified by flash chromatography to obtain Compound 14 as a tan solid. LCMS (M/Z): 352 (M+H). ¹H NMR (400 MHz, acetone) δ ppm 7.53-7.63 (m, 3 H) 7.91 (d, J=8.64 Hz, 2 H) 8.03 (td, J=7.75, 1.54 Hz, 1 H) 8.24 (d, J=8.00 Hz, 1 H) 8.66 (d, J=4.49 Hz, 1 H).

By proceeding in a similar manner, the following Compounds were also prepared:

Compound 15: 2-chloro-N-[3-(2-pyridyl)-1,2,4-thiadiazol-5-yl]benzenesulfonamide

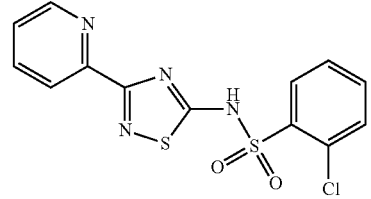 [SMILES: O=S(=O)(Nc1nc(-c2ccccn2)ns1)c1ccccc1Cl]

LCMS (M/Z): 352 (M+H). ¹H NMR (400 MHz, acetone) δ ppm 7.52-7.67 (m, 4 H) 8.07 (td, J=7.78, 1.71 Hz, 1 H) 8.17-8.28 (m, 2 H) 8.64-8.73 (m, 1 H).

Compound 16: 4-cyano-N-[3-(2-pyridyl)-1,2,4-thiadiazol-5-yl]benzenesulfonamide

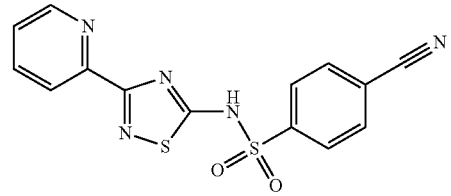 [SMILES: N#Cc1ccc(S(=O)(=O)Nc2nc(-c3ccccn3)ns2)cc1]

LCMS (M/Z): 344 (M+H). ¹H NMR (400 MHz, acetone) δ ppm 7.61 (ddd, J=7.57, 4.88, 1.02 Hz, 1 H) 7.97-8.02 (m, 2 H) 8.06 (td, J=7.80, 1.68 Hz, 1 H) 8.08-8.13 (m, 2 H) 8.24 (d, J=7.96 Hz, 1 H) 8.68 (d, J=4.54 Hz, 1 H).

Compound 17: 4-methoxy-N-[3-(2-pyridyl)-1,2,4-thiadiazol-5-yl]benzenesulfonamide

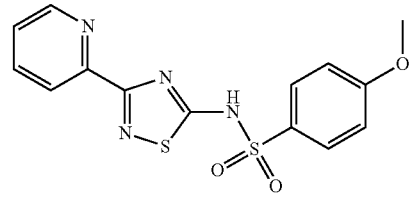 [SMILES: COc1ccc(S(=O)(=O)Nc2nc(-c3ccccn3)ns2)cc1]

LCMS (M/Z): 349 (M+H). ¹H NMR (400 MHz, acetone) δ ppm 3.88 (s, 3 H) 7.01-7.10 (m, 2 H) 7.58 (dd, J=7.10, 5.34 Hz, 1 H) 7.79-7.88 (m, 2 H) 8.03 (td, J=7.76, 1.61 Hz, 1 H) 8.22 (d, J=7.96 Hz, 1 H) 8.67 (d, J=4.88 Hz, 1 H).

Compound 18: 2-methoxy-N-[3-(2-pyridyl)-1,2,4-thiadiazol-5-yl]benzenesulfonamide

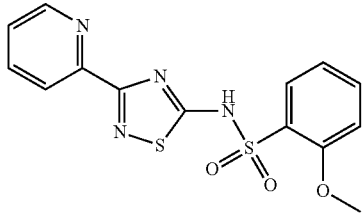 [SMILES: COc1ccccc1S(=O)(=O)Nc1nc(-c2ccccn2)ns1]

LCMS (M/Z): 349 (M+H). $^1$H NMR (400 MHz, acetone) δ ppm 3.81 (s, 3 H) 7.10 (td, J=7.63, 0.95 Hz, 1 H) 7.17 (d, J=8.25 Hz, 1 H) 7.52-7.64 (m, 2 H) 7.96 (dd, J=7.86, 1.71 Hz, 1 H) 8.05 (td, J=7.78, 1.71 Hz, 1 H) 8.25 (d, J=7.91 Hz, 1 H) 8.68 (d, J=4.64 Hz, 1 H).

Compound 19: N-[3-(2-pyridyl)-1,2,4-thiadiazol-5-yl]-3-(trifluoromethyl)benzenesulfonamide

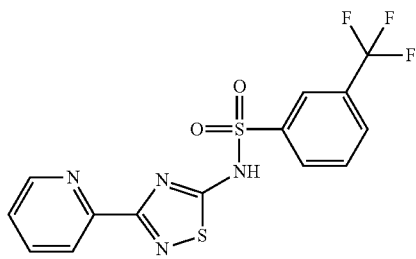 [SMILES: O=S(=O)(Nc1nc(-c2ccccn2)ns1)c1cccc(C(F)(F)F)c1]

LCMS (M/Z): 386 (M+H). $^1$H NMR (400 MHz, acetone) δ ppm 7.57-7.68 (m, 1 H) 7.83-7.91 (m, 1 H) 8.01 (d, J=7.81 Hz, 1 H) 8.07 (t, J=7.52 Hz, 1 H) 8.18 (s, 1 H) 8.23 (t, J=8.40 Hz, 2 H) 8.69 (d, J=4.30 Hz, 1 H).

Compound 20: N-[3-(2-pyridyl)-1,2,4-thiadiazol-5-yl]-4-(trifluoromethyl)benzenesulfonamide

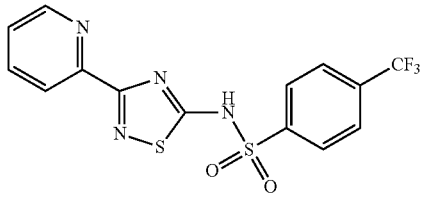 [SMILES: O=S(=O)(Nc1nc(-c2ccccn2)ns1)c1ccc(C(F)(F)F)cc1]

LCMS (M/Z): 387 (M+H). $^1$H NMR (400 MHz, DMSO-$d_6$) δ ppm 7.63-7.73 (m, 1 H) 7.92 (d, J=8.40 Hz, 2 H) 8.02 (d, J=8.20 Hz, 2 H) 8.08-8.17 (m, 1 H) 8.17-8.25 (m, 1 H) 8.69 (d, J=4.69 Hz, 1 H).

Example 4

N-[3-(3-Fluoro-2-pyridyl)-1,2,4-thiadiazol-5-yl]-4-(trifluoromethyl)benzamide (Compound 21)

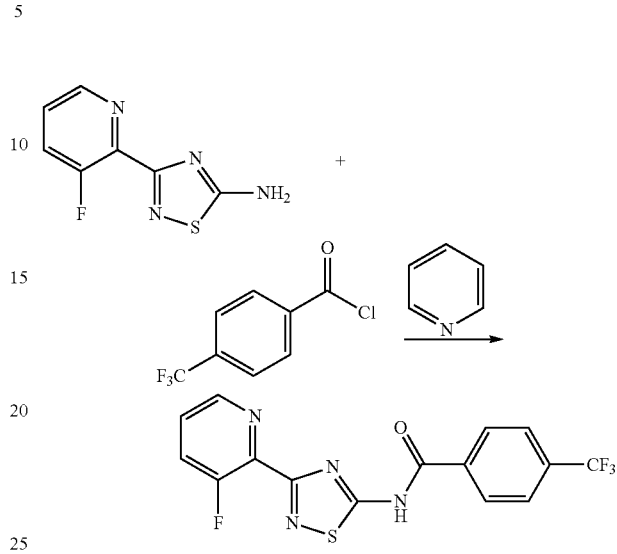

3-(3-Fluoro-2-pyridyl)-1,2,4-thiadiazol-5-amine (50 mg, 0.25 mmol) was dissolved in 2 mL dichloromethane. Pyridine (25 µL, 0.30 mmol) was added followed by 4-(trifluoromethyl)benzoyl chloride (45 µL, 0.28 mmol). The mixture was stirred under nitrogen at room temperature for 16 hours. The reaction mixture was partitioned between dichloromethane and water. The aqueous layer was extracted with dichloromethane. The combined organic layer was dried over sodium sulfate, filtered and concentrated. The crude product was purified by flash chromatography to obtain the Compound 21 as a white solid. LCMS (M/Z): 369 (M+H). $^1$H NMR (400 MHz, acetone) δ ppm 7.62 (dt, J=8.40, 4.20 Hz, 1 H) 7.73-7.85 (m, 1 H) 8.01 (d, J=8.40 Hz, 2 H) 8.50 (d, J=8.00 Hz, 2 H) 8.59 (d, J=4.49 Hz, 1 H).

Synthesis 3-fluoropyridine-2-carboxamidine

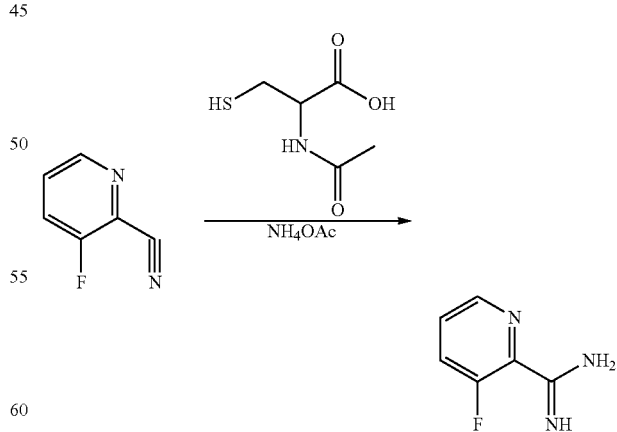

3-Fluoro-2-pyridinecarbonitrile (500 mg, 4.1 mmol) and N-acetyl-L-cysteine (75 mg, 0.45 mmol) were dissolved in 4 mL methanol. Ammonium acetate (380 mg, 4.9 mmol) was added and the reaction stirred at 50° C. for 14 hours. The solution was evaporated under reduced pressure and purified by flash chromatography. The product was recovered as a tan solid (70 mg, 30%). LCMS (M/Z): 140 (M+H).

Synthesis of 3-(3-fluoro-2-pyridyl)-1,2,4-thiadiazol-5-amine

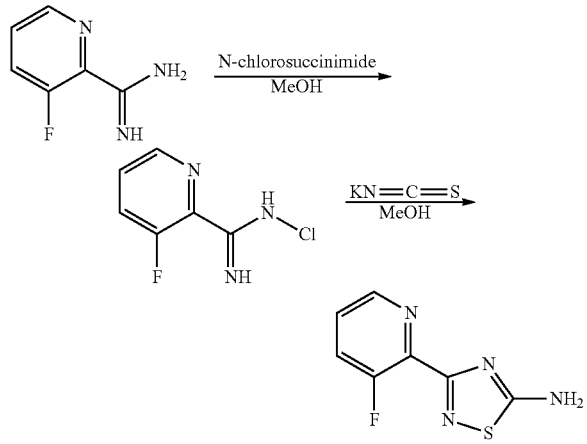

3-Fluoropyridine-2-carboxamidine (150 mg, 1.07 mmol) was dissolved in 3 mL methanol. Triethylamine (150 µL, 1.07 mmol) was added, followed by N-chlorosuccinimide (145 mg, 1.07 mmol). The reaction stirred at ambient temperature for 14 hours. LCMS of crude reaction (M/Z): 174 (M+H). Potassium thiocyanate (105 mg, 1.07 mmol) was added to the reaction mixture. After 1 hour the reaction was complete. The solution was evaporated under reduced pressure and purified by flash chromatography. The product was recovered as clear oil (170 mg, 80% over 2 steps). LCMS (M/Z): 197 (M+H). $^1$H NMR (400 MHz, DMSO-$d_6$) δ ppm 7.54 (dd, J=8.20, 4.10 Hz, 1 H) 7.80 (t, J=9.57 Hz, 1 H) 8.06 (br. s., 2 H) 8.46 (d, J=3.71 Hz, 1 H).

Example 5

4-methyl-N-[3-(2-pyridyl)-1,2,4-thiadiazol-5-yl]thiophene-2-carboxamide (Compound 53)

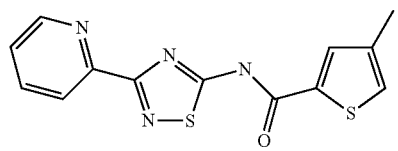 [SMILES: Cc1csc(C(=O)Nc2nc(-c3ccccn3)ns2)c1]

3-Pyridin-2-yl-[1,2,4]thiadiazol-5-ylamine (50 mg, 0.28 mmol) was placed in a vial and dissolved in dioxane (1.5 mL) and then added 3 N NaOH (1.5 mL). Then 4-methyl-thiophene-2-carbonyl chloride (45 mg, 0.28 mmol) was added and the reaction heated to 50° C. for 16 h. The reaction was then diluted with water and acidified with AcOH to force precipitation. The precipitates were collected by filtration. The collected solid was redissolved and concentrated onto celite (5 g). Then purified by normal phase chromatography (solvent A CH$_2$Cl$_2$, solvent B CH$_2$Cl$_2$/MeOH/NH$_4$OH 90:10:1, gradient from 0-60% B). Collected the desired product (72 mg, 0.24 mmol, 86%). $^1$H NMR (400 MHz, DMSO-$d_6$) δ ppm 2.25 (s, 3 H) 7.49 (ddd, J=7.55, 4.75, 1.12 Hz, 1 H) 7.65 (s, 1 H) 7.95 (td, J=7.74, 1.81 Hz, 1 H) 8.13 (d, J=1.02 Hz, 1 H) 8.20 (d, J=7.91 Hz, 1 H) 8.62-8.74 (m, 1 H) 13.75 (br, s., 1 H); LCMS (M/Z): M+H$^+$303.

Example 6

4-phenoxy-N-[3-(2-pyridyl)-1,2,4-thiadiazol-5-yl]benzamide (Compound 63)

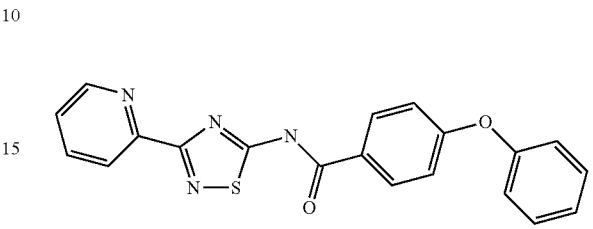

3-Pyridin-2-yl-[1,2,4]thiadiazol-5-ylamine (50 mg, 0.28 mmol), 4-phenoxybenzoic acid (120 mg, 0.56 mmol), and 1-[bis(dimethylamino)methylene]-1H-1,2,3-triazolo[4,5-b]pyridinium 3-oxid hexafluorophosphate (128 mg, 0.34 mmol) was placed in a vial. Then dissolved in DMF (3 mL, anhydrous), added N,N-diisopropylethylamine (98 µL, 0.56 mmol), and stirred at 50° C. for 16 h. The reaction was diluted with water and extracted with EtOAc (×3). The combined organic layers were dried and concentrated onto celite. Purified by normal phase chromatography (solvent A CH$_2$Cl$_2$, solvent B CH$_2$Cl$_2$/MeOH/NH$_4$OH 90:10:1, gradient from 0-50% B). Collected the desired product (25.2 mg, 0.0674 mmol, 24%). $^1$H NMR (400 MHz, DMSO-$d_6$) δ ppm 7.11 (d, J=8.83 Hz, 2 H) 7.16 (d, J=7.66 Hz, 2 H) 7.23-7.31 (m, 1 H) 7.43-7.56 (m, 3 H) 7.98 (td, J=7.75, 1.73 Hz, 1 H) 8.24 (d, J=8.74 Hz, 3 H) 8.72 (d, J=4.34 Hz, 1 H) 13.71 (br, s., 1 H); LCMS (M/Z): M+H$^+$375.

Example 7

4-(3-pyridyl)-N-[3-(2-pyridyl)-1,2,4-thiadiazol-5-yl]benzamide (Compound 111)

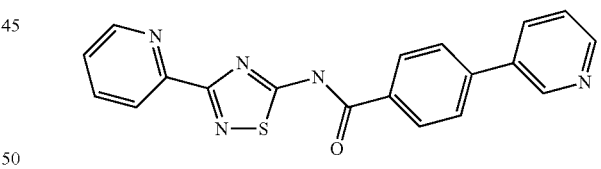

4-Iodo-N-[3-(2-pyridyl)-1,2,4-thiadiazol-5-yl]benzamide (50 mg, 0.12 minol), 3-pyridylboronic acid (30 mg, 0.24 mmol), PdCl$_2$(dppf)CH$_2$Cl$_2$ (50 mg, 0.061 mmol), and Cs$_2$CO$_3$ (120 mg, 0.37 mmol) were placed in a vial. Then added dioxane (2 mL, degassed) and water (200 µL, degassed). The reaction was then degassed, placed under N$_2$, and heated to 100° C. for 16 h. The reaction was cooled, added EtOAc and water, and extracted with EtOAc (×3). The combined organic layers were dried and concentrated onto celite (5 g). Purified by normal phase chromatography (solvent A CH$_2$Cl$_2$, solvent B CH$_2$Cl$_2$/MeOH/NH$_4$OH 90:10:1, gradient from 0-50% B). The collected product was redissolved in CH$_2$Cl$_2$/MeOH and concentrated onto celite (5 g). Then further purified by reverse phase chromatography (solvent A water with 0.1% formic acid, solvent B CH$_3$CN with 0.1% formic acid, gradient from 5-100% B).

Collected the desired product (1.7 mg, 0.0047 mmol, 4%). $^1$H NMR (400 MHz, DMSO-d$_6$) δ ppm 7.48 (ddd, J=7.44, 4.78, 0.95 Hz, 1 H) 7.53 (dd, J=7.96, 4.78 Hz, 1 H) 7.88-8.00 (m, 3 H) 8.20 (dt, J=8.00, 1.95 Hz, 1 H) 8.25 (d, J=7.86 Hz, 1 H) 8.33 (d, J=8.49 Hz, 2 H) 8.63 (dd, J=4.76, 1.54 Hz, 1 H) 8.71 (d, J=4.00 Hz, 1 H) 9.01 (d, J=1.81 Hz, 1 H); LCMS (M/Z): M+H$^+$360.

Example 8

4-(2-pyridylamino)-N-[3-(2-pyridyl)-1,2,4-thiadiazol-5-yl]benzamide (Compound 75)

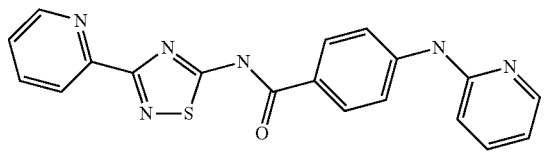 [SMILES: O=C(Nc1nc(-c2ccccn2)ns1)c1ccc(Nc2ccccn2)cc1]

4-Iodo-N-[3-(2-pyridyl)-1,2,4-thiadiazol-5-yl]benzamide (50 mg, 0.12 mmol), pyridin-2-amine (46 mg, 0.49 mmol), Pd$_2$(dba)$_3$ (56 mg, 0.061 mmol), X-Phos (58 mg, 0.12 mmol), and NaOt-Bu (71 mg, 0.73 mmol) were placed in a vial. Then added dioxane (2 mL, anhydrous, degassed). The reaction was then degassed, placed under N$_2$ and heated to 100° C. for 16 h. The reaction was cooled, added EtOAc and water, and extracted with EtOAc (×3). The combined organic layers were dried and concentrated onto celite (5 g). Purified by normal phase chromatography (solvent A CH$_2$Cl$_2$, solvent B CH$_2$Cl$_2$/MeOH/NH$_4$OH 90:10:1, gradient from 0-50% B). The collected product was redissolved in CH$_2$Cl$_2$/MeOH and concentrated onto celite (5 g). Then further purified by reverse phase chromatography (solvent A water with 0.1% formic acid, solvent B CH$_3$CN with 0.1% formic acid, gradient from 5-100% B). Collected the desired product (7.7 mg, 0.0206 mmol, 17%). $^1$H NMR (400 MHz, DMSO-d$_6$) δ ppm 7.50 (ddd, J=7.49, 4.76, 0.98 Hz, 1 H) 7.66 (ddd, J=8.49, 7.00, 1.93 Hz, 1 H) 7.88 (d, J=8.88 Hz, 2 H) 7.97 (td, J=7.72, 1.73 Hz, 1 H) 8.14 (d, J=8.88 Hz, 2 H) 8.21-8.30 (m, 3 H) 8.71 (d, J=3.95 Hz, 1 H) 9.57 (s, 1 H); LCMS (M/Z): M+H$^+$375.

Example 9

N-[3-[4-(triazolo[4,5-b]pyridin-3-yloxy)-2-pyridyl]-1,2,4-thiadiazol-5-yl]-4-(trifluoromethyl)benzamide (Compound 28)

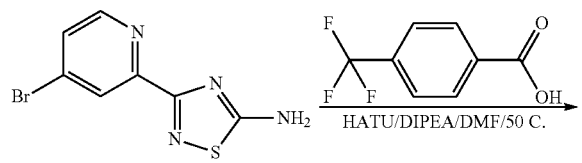

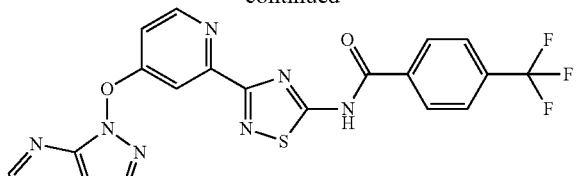

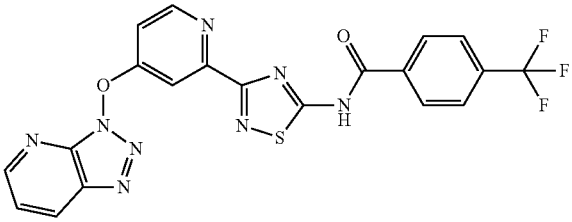

The amine (261.4 mg, 1.02 mmol) and p-trifluoromethylbenzoic acid (194 mg, 1.02 mmol) was dissolved in anhydrous DMF (5 mL) to which mixture was added N,N-diisopropylethylamine (0.36 mL, 2.04 mmol) and HATU (387 mg, 1.02 mmol). The mixture was heated at 50° C. overnight. The reaction mixture was cooled to room temperature and partitioned between EtOAc and water. The aqueous layer was extracted with EtOAc (5×). The combined organic layer was dried over Na$_2$SO$_4$, filtered and concentrated. The crude product was purified by ISCO to obtain the product (136.1 mg). $^1$H NMR (400 MHz, DMSO-d$_6$) δ ppm 7.37 (dd, J=5.66, 2.73 Hz, 1H) 7.66-7.79 (m, 2H) 7.99 (d, J=8.40 Hz, 2H) 8.35 (d, J=8.20 Hz, 2H) 8.77 (d, J=5.66 Hz, 1H) 8.84 (dd, J=8.49, 1.07 Hz, 1H) 8.86-8.89 (m, 1H) M+H]$^+$429

Example 10

N-[3-[4-[2-methoxyethyl(methyl)amino]-2-pyridyl]-1,2,4-thiadiazol-5-yl]-4-(trifluoromethyl)benzamide (Compound 25)

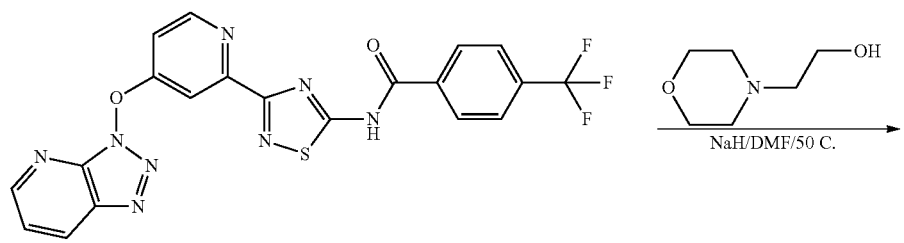

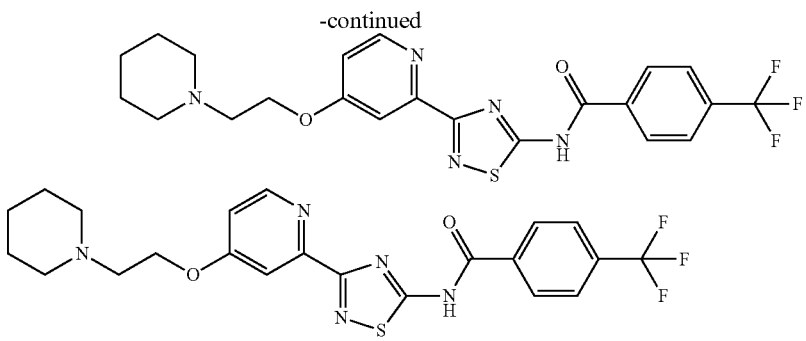

The mixture of N-[3-[4-(triazolo[4,5-b]pyridin-3-yloxy)-2-pyridyl]-1,2,4-thiadiazol-5-yl]-4-(trifluoromethyl)benzamide (30 mg, 0.063 mmol) and 2-methoxy-N-methylethanamine (34 µL, 0.31 mmol) in anhydrous DMF (1 mL) was heated at 50° C. overnight. The reaction mixture was directly purified by HPLC to obtain the product (7.2 mg). $^1$H NMR (400 MHz, DMSO-d$_6$) δ ppm 1.91 (s, 2H) 3.15 (s, 3H) 3.55-3.63 (m, 2H) 3.63-3.80 (m, 2H) 6.85 (d, J=3.71 Hz, 1H) 7.59 (d, J=2.73 Hz, 1H) 7.81 (d, J=8.40 Hz, 2H) 8.02-8.18 (m, 1H) 8.36 (d, J=8.00 Hz, 2H) M+H]$^+$438

N-[3-[4-[2-(1-piperidyl)ethoxy]-2-pyridyl]-1,2,4-thiadiazol-5-yl]-4-(trifluoromethyl)benzamide
(Compound 140)

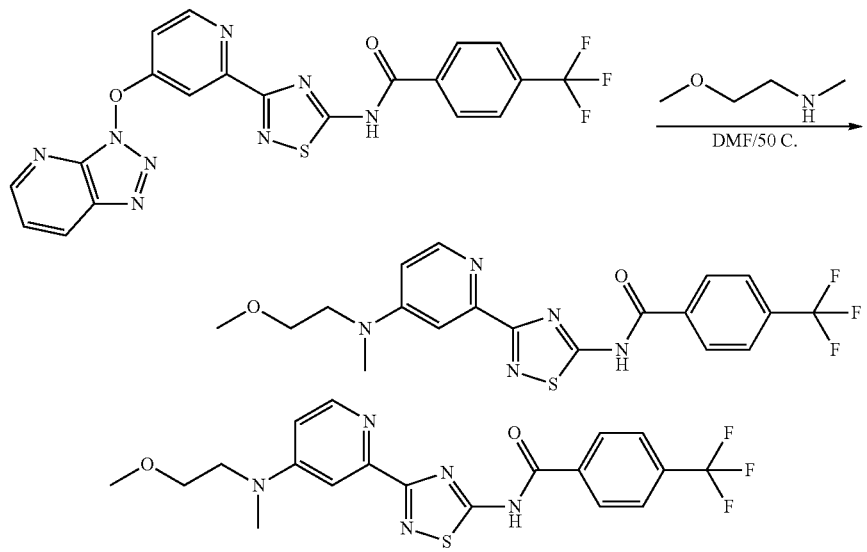

2-morpholinoethanol (67 µL, 0.52 mmol) was dissolved in anhydrous DMF (1 mL) to which solution was added sodium hydride (20 mg, 60 wt % in mineral oil, 0.46 mmol). Gas evolution. The mixture was stirred at 50° C. for 1 h before a solution of N-[3-[4-(triazolo[4,5-b]pyridin-3-yloxy)-2-pyridyl]-1,2,4-thiadiazol-5-yl]-4-(trifluoromethyl)benzamide (50 mg, 0.10 mmol, in 1 mL of anhydrous DMF) was added. The mixture was then stirred at 50° C. overnight. The crude mixture was directly purified by HPLC to obtain the product (11.8 mg). $^1$H NMR (400 MHz, DMSO-d$_6$) δ ppm 1.91 (s, 2H) 2.76 (t, J=5.56 Hz, 2H) 3.52-3.70 (m, 4H) 4.27 (t, J=5.66 Hz, 2H) 7.02 (d, J=2.93 Hz, 1H) 7.78 (d, J=2.34 Hz, 1H) 7.85 (d, J=8.20 Hz, 2H) 8.36 (d, J=801 Hz, 2H) 8.46 (d, J=5.66 Hz, 1H) M+H]$^+$480

By proceeding in a similar manner the following compounds of the invention were prepared using the procedures described in one of Examples 1 to 10.

Liquid chromatography—mass spectrometry (LCMS) experiments to determine retention times and associated mass ions were performed using one or more of the following Methods A, B, and C:

Method A: Waters BEH C18, 3.0×30 mm, 1.7 µm, was used at a temperature of 50° C. and at a flow rate of 1.5 mL/min, 2 µL injection, mobile phase: (A) water with 0.1% formic acid and 1% acetonitrile, mobile phase (B) MeOH with 0.1% formic acid; retention time given in minutes. Method A details: (I) ran on a Binary Pump G1312B with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP, 2.1×50 mm, 3.5 µm, was used at a temperature of 50° C. and at a flow rate of 0.8 mL/min, 2 µL injection, mobile phase: (A) water with 0.1% formic acid and 1% acetonitrile, mobile phase (B) MeOH with 0.1% formic acid; retention time given in minutes. Method details: (I) ran on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Method C: An API 150EX mass spectrometer linked to a Shimadzu LC-10AT LC system with a diode array detector was used. The spectrometer had an electrospray source operating in positive and negative ion mode. LC was carried out using an Agilent ZORBAX XDB 50×2.1 mm C18 column and a 0.5 mL/minute flow rate. Solvent A: 95% water, 5% acetonitrile containing 0.01% formic acid; Solvent B: acetonitrile. The gradient was shown as below. 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

TABLE 2

| Cpd. | Name | Mass found | LCMS retention time |
|---|---|---|---|
| 22 | N-[3-(4-morpholino-2-pyridyl)-1,2,4-thiadiazol-5-yl]-4-(trifluoromethyl)benzamide<br>$^1$H NMR (400 MHz, DMSO-$d_6$) δ ppm 3.54 (br s, 4H) 3.76 (t, J = 4.69 Hz, 4H) 7.07 (d, J = 4.10 Hz, 1H) 7.75 (d, J = 2.34 Hz, 1H) 7.87 (d, J = 8.00 Hz, 2H) 8.24 (d, J = 6.44 Hz, 1H) 8.36 (d, J = 8.20 Hz, 2H) M + H]$^+$ 436 | 436 | 1.35 |
| 23 | N-[3-[4-[benzyl(methyl)amino]-2-pyridyl]-1,2,4-thiadiazol-5-yl]-4-(trifluoromethyl)benzamide<br>$^1$H NMR (400 MHz, DMSO-$d_6$) δ ppm 1.91 (s, 3H) 4.88 (s, 2H) 6.93 (d, J = 5.08 Hz, 1H) 7.19-7.34 (m, 4H) 7.33-7.42 (m, 2H) 7.63 (s, 1H) 7.83 (d, J = 8.20 Hz, 2H) 8.08-8.25 (m, 1H) 8.09-8.21 (m, 1H) 8.35 (d, J = 8.20 Hz, 2H) 8.31-8.41 (m, 1H) M + H]$^+$ 470 | 470 | 1.63 |
| 24 | N-[3-[4-(dimethylamino)-2-pyridyl]-1,2,4-thiadiazol-5-yl]-4-(trifluoromethyl)benzamide<br>$^1$H NMR (400 MHz, DMSO-$d_6$) δ ppm 3.09 (br s, 1H) 3.25 (br s, 6H) 6.97 (d, J = 4.30 Hz, 1H) 7.60 (br s, 1H) 7.84 (d, J = 7.81 hz, 2H) 8.14 (d, J = 6.64 Hz, 1H) 8.36 (d, J = 8.00 Hz, 2H) M + H]$^+$ 408 | 394 | 1.36 |
| 25 | N-[3-[4-[2-methoxyethyl(methyl)amino]-2-pyridyl]-1,2,4-thiadiazol-5-yl]-4-(trifluoromethyl)benzamide<br>$^1$H NMR (400 MHz, DMSO-$d_6$) δ ppm 1.91 (s, 2H) 3.15 (s, 3H) 3.55-3.63 (m, 2H) 3.63-3.80 (m, 2H) 6.85 (d, J = 3.71 Hz, 1H) 7.59 (d, J = 2.73 Hz, 1H) 7.81 (d, J = 8.40 Hz, 2H) 8.02-8.18 (m, 1H) 8.36 (d, J = 8.00 Hz, 2H) M + H]$^+$ 438 | 438 | 1.31 |
| 26 | N-[3-(5-methoxy-2-pyridyl)-1,2,4-thiadiazol-5-yl]-4-(trifluoromethyl)benzamide<br>$^1$H NMR (400 MHz, DMSO-$d_6$) δ ppm 3.91 (s, 3H) 7.54 (dd, J = 8.79, 2.93 Hz, 1H) 7.95 (d, J = 8.20 Hz, 2H) 8.21 (d, J = 8.79 Hz, 1H) 8.31-8.46 (m, 3H) M + H]$^+$ 381 | 381 | 1.88 |
| 27 | N-[3-(4-methoxy-2-pyridyl)-1,2,4-thiadiazol-5-yl]-4-(trifluoromethyl)benzamide,<br>$^1$H NMR (400 MHz, DMSO-$d_6$) δ ppm 3.93 (s, 3H) 7.09 (dd, J = 5.66, 2.54 Hz, 1H) 7.78 (d, J = 2.34 Hz, 1H) 7.96 (d, J = 8.00 Hz, 2H) 8.38 (d, J = 8.20 Hz, 2H) 8.52 (d, J = 5.86 Hz, 1H) M + H]$^+$ 381 | 381 | 1.65 |
| 28 | N-[3-[4-(triazolo[4,5-b]pyridin-3-yloxy)-2-pyridyl]-1,2,4-thiadiazol-5-yl]-4-(trifluoromethyl)benzmide<br>$^1$H NMR (400 MHz, DMSO-$d_6$) δ ppm 7.37 (dd, J = 5.66, 2.73 Hz, 1H) 7.66-7.79 (m, 2H) 7.99 (d, J = 8.40 Hz, 2H) 8.35 (d, J = 8.20 Hz, 2H) 8.77 (d, J = 5.66 Hz, 1H) 8.84 (dd, J = 8.49, 1.07 Hz, 1H) 8.86-8.89 (m, 1H) M + H]$^+$ 429 | 485 | 1.91 |
| 29 | N-[3-(5-bromo-2-pyridyl)-1,2,4-thiadiazol-5-yl]-4-(trifluoromethyl)benzamide<br>$^1$H NMR (400 MHz, DMSO-$d_6$) δ ppm 7.97 (s, 2 H) 8.11-8.19 (m, 1 H) 8.23 (d, J = 2.29 Hz, 1H) 8.34 (d, J = 8.20 Hz, 2 H) 8.83 (d, J = 2.25 Hz, 1 H). | 429 | 1.97 |
| 30 | methyl 2-[5-[[4-(trifluoromethyl)benzoyl]amino]-1,2,4-thiadiazol-3-yl]pyridine-4-carboxylate<br>$^1$H NMR (400 MHz, DMSO-$d_6$) δ ppm 3.96 (s, 3H) 7.88-8.00 (m, 3H) 8.38 (d, J = 8.20 Hz, 2H) 8.71 (s, 1H) 8.93 (d, J = 5.08 Hz, 1H) M + H]$^+$ 409 | 409 | 1.88 |
| 31 | N-[3-(2-pyridyl)-1,2,4-thiadiazol-5-yl]isoquinoline-7-carboxamide<br>$^1$H NMR (400 MHz, DMSO-$d_6$) δ ppm 7.53 (dd, J = 6.74, 4.98 Hz, 1H) 7.93-8.05 (m, 2H) 8.18 (d, J = 8.59 Hz, 1H) 8.27 (d, J = 7.81 Hz, 1H) 8.46 (dd, | 334 | 1.29 |

TABLE 2-continued

| Cpd. | Name | Mass found | LCMS retention time |
|---|---|---|---|
|  | J = 8.59, 1.56 Hz, 1H) 8.67 (d, J = 5.66 Hz, 1H) 8.74 (d, J = 4.30 Hz, 1H) 9.09 (s, 1H) 9.49 (s, 1H) M + H]+ 334 | | |
| 32 | 4-acetamido-N-[3-(2-pyridyl)-1,2,4-thiadiazol-5-yl]benzamide<br>$^1$H NMR (400 MHz, DMSO-d$_6$) δ ppm 2.11 (s, 3H) 7.59 (dd, J = 6.64, 4.88 Hz, 1H) 7.79 (d, J = 8.79 Hz, 2H) 8.07 (td, J = 7.71, 1.56 Hz, 1H) 8.17 (d, J = 8.79 Hz, 2H) 8.29 (d, J = 7.81 Hz, 1H) 8.75 (d, J = 4.30 Hz, 1H) 10.39 (s, 1H) M + H]+ 340 | 340 | 1.48 |
| 33 | 4-fluoro-N-[3-(2-pyridyl)-1,2,4-thiadiazol-5-yl]benzamide<br>$^1$H NMR (400 MHz, DMSO-d$_6$) δ ppm 7.46 (t, J = 8.79 Hz, 2H) 7.54-7.64 (m, 1H) 8.06 (td, J = 7.71, 1.56 Hz, 1H) 8.23-8.35 (m, 3H) 8.75 (d, J = 4.30 Hz, 1H) M + H]+ 301 | 301 | 1.5 |
| 34 | 4-nitro-N-[3-(2-pyridyl)-1,2,4-thiadiazol-5-yl]benzamide<br>$^1$H NMR (400 MHz, DMSO-d$_6$) δ ppm 7.53 (dd, J = 6.64, 4.88 Hz, 1H) 7.99 (td, J = 7.71, 1.56 Hz, 1H) 8.26 (d, J = 7.81 Hz, 1H) 8.42 (s, 5H) 8.73 (d, J = 4.30 Hz, 1H) M + H]+ 328 | 328 | 1.49 |
| 35 | N-[3-(2-pyridyl)-1,2,4-thiadiazol-5-yl]quinoxaline-6-carboxamide<br>$^1$H NMR (400 MHz, DMSO-d$_6$) δ ppm 7.56 (dd, J = 7.03, 5.27 Hz, 1H) 8.03 (td, J = 7.71, 1.56 Hz, 1H) 8.30 (dd, J = 8.30, 5.37 Hz, 2H) 8.53 (dd, J = 8.79, 1.95 Hz, 1H) 8.75 (d, J = 4.30 Hz, 1H) 9.05 (d, J = 1.76 Hz, 1H) 9.11 (d, J = 1.37 Hz, 1H) M + H]+ 335 | 335 | 1.35 |
| 36 | N-[3-(2-pyridyl)-1,2,4-thiadiazol-5-yl]thiophene-2-carboxamide<br>$^1$H NMR (400 MHz, DMSO-d$_6$) δ ppm 7.28-7.39 (m, 1H) 7.58 (dd, J = 6.83, 5.08 Hz, 1H) 8.05 (td, J = 7.71, 1.56 Hz, 1H) 8.10 (d, J = 4.88 Hz, 1H) 8.27 (d, J = 7.81 Hz, 1H) 8.37 (d, J = 3.12 Hz, 1H) 8.74 (d, J = 4.30 Hz, 1H) M + H]+ 289 | 289 | 1.36 |
| 37 | N-[3-(2-pyridyl)-1,2,4-thiadiazol-5-yl]thiophene-3-carboxamide<br>$^1$H NMR (400 MHz, DMSO-d$_6$) δ ppm 7.51-7.62 (m, 1H) 7.69-7.79 (m, 1H) 7.79-7.87 (m, 1H) 8.05 (t, J = 7.71 Hz, 1H) 8.27 (d, J = 7.81 Hz, 1H) 8.69-8.79 (m, 1H) M + H]+ 289 | 289 | 1.92 |
| 38 | N-[3-(4-isopropyl-2-pyridyl)-1,2,4-thiadiazol-5-yl]-4-(trifluoromethyl)benzamide<br>$^1$H NMR (400 MHz, DMSO-d$_6$) δ ppm 1.17-1.44 (m, 6H) 3.07 (quin, J = 6.93 Hz, 1 H) 7.51 (d, J = 4.10 Hz, 1H) 8.01 (d, J = 8.20 Hz, 2H) 8.18 (s, 1H) 8.39 (d, J = 8.20 Hz, 2H) 8.65 (d, J = 5.08 Hz, 1H) M + H]+ 393 | 393 | 2.04 |
| 39 | N-[3-(3-isoquinolyl)-1,2,4-thiadiazol-5-yl]-4-(trifluoromethyl)benzamide<br>$^1$H NMR (400 MHz, DMSO-d$_6$) δ ppm 7.74-7.83 (m, 1H) 7.87 (t, J = 7.22 Hz, 1H) 8.00 (d, J = 8.40 Hz, 2H) 8.17 (d, J = 8.20 Hz, 1H) 8.23 (d, J = 8.20 Hz, 1H) 8.40 (d, J = 8.20 Hz, 2H) 8.73 (s, 1H) 9.46 (s, 1H) M + H]+ 401 | 401 | 1.96 |
| 40 | N-[3-(5-fluoro-2-pyridyl)-1,2,4-thiadiazol-5-yl]-4-(trifluoromethyl)benzamide<br>$^1$H NMR (400 MHz, DMSO-d$_6$) δ ppm 7.92 (td, J = 8.69, 2.93 Hz, 1H) 8.00 (d, J = 8.20 Hz, 2H) 8.33 (dd, J = 8.79, 4.49 Hz, 1H) 8.38 (d, J = 8.00 Hz, 2H) 8.73 (d, J = 2.93 Hz, 1H) M + H]+ 369 | 369 | 1.86 |
| 41 | N-[3-(5-methyl-2-pyridyl)-1,2,4-thiadiazol-5-yl]-4-(trifluoromethyl)benzamide<br>$^1$H NMR (400 MHz, DMSO-d$_6$) δ ppm 2.38 (s, 3 H) 7.78 (dd, J = 8.03, 1.59 Hz, 1 H) 7.97 (d, J = 8.25 Hz, 2 H) 8.14 (d, J = 8.00 Hz, 1 H) 8.37 (d, J = 8.15 Hz, 2 H) 8.56 (d, J = 1.85 Hz, 1 H); LCMS (M/Z): M + H+ 365. | 365 | 1.88 |

TABLE 2-continued

| Cpd. | Name | Mass found | LCMS retention time |
|---|---|---|---|
| 42 | 3-chloro-4-fluoro-N-[3-(5-fluoro-2-pyridyl)-1,2,4-thiadiazol-5-yl]benzamide<br>$^1$H NMR (400 MHz, DMSO-d6) d ppm 7.66 (t, J = 8.88 Hz, 1 H) 7.83-7.98 (m, 1 H) 8.21 (ddd, J = 8.49, 4.59, 2.15 Hz, 1 H) 8.30 (dd, J = 8.79, 4.49 Hz, 1 H) 8.44 (dd, J = 7.03, 1.95 Hz, 1 H) 8.71 (d, J = 2.54 Hz, 1 H); MS (M + H) = 353.0. | 353 | 1.86 |
| 43 | N-[3-(5-fluoro-2-pyridyl)-1,2,4-thiadiazol-5-yl]-4-(trifluoromethoxy)benzamide<br>$^1$H NMR (400 MHz, DMSO-d6) d ppm 7.60 (d, J = 8.20 Hz, 2 H) 7.84-7.98 (m, 1 H) 8.33 (d, J = 8.79 Hz, 3 H) 8.72 (d, J = 2.73 Hz, 1 H); MS (M + H) = 385.0. | 385 | 1.87 |
| 44 | 4-tert-butyl-N-[3-(5-fluoro-2-pyridyl)-1,2,4-thiadiazol-5-yl]benzamide<br>$^1$H NMR (400 MHz, DMSO-d6) d ppm 1.33 (s, 9 H) 7.62 (d, J = 8.59 Hz, 2 H) 7.83-7.98 (m, 1 H) 8.15 (d, J = 8.40 Hz, 2 H) 8.26-8.40 (m, 1 H) 8.71 (d, J = 2.73 Hz, 1 H); MS (M + H) = 357.0. | 357 | 1.99 |
| 45 | N-[3-(5-fluoro-2-pyridyl)-1,2,4-thiadiazol-5-yl]-3,5-bis(trifluoromethyl)benzamide<br>$^1$H NMR (400 MHz, DMSO-d6) d ppm 7.92 (d, J = 2.73 Hz, 1 H) 8.26-8.37 (m, 1 H) 8.49 (s, 1 H) 8.72 (d, J = 2.54 Hz, 1 H) 8.82 (s, 2 H); MS (M + H) = 437.0. | 437 | 2.05 |
| 46 | N-[3-(5-fluoro-2-pyridyl)-1,2,4-thiadiazol-5-yl]-3-(trifluoromethyl)benzamide<br>$^1$H NMR (400 MHz, DMSO-d6) d ppm 7.86 (s, 2 H) 8.07 (s, 1 H) 8.26-8.38 (m, 1 H) 8.45 (s, 1 H) 8.59 (s, 1 H) 8.72 (d, J = 2.93 Hz, 1 H); MS (M + H) = 369.0. | 369 | 1.84 |
| 47 | 3,4-dichloro-N-[3-(5-fluoro-2-pyridyl)-1,2,4-thiadiazol-5-yl]benzamide<br>$^1$H NMR (400 MHz, DMSO-d6) d ppm 7.87 (d, J = 8.40 Hz, 2 H) 8.07-8.19 (m, 1 H) 8.25-8.37 (m, 1 H) 8.44 (d, J = 1.95 Hz, 1 H) 8.71 (d, J = 2.73 Hz, 1 H); MS (M + H) = 368.9. | 369 | 1.97 |
| 48 | 3-methylsulfonyl-N-[3-(2-pyridyl)-1,2,4-thiadiazol-5-yl]benzamide<br>$^1$H NMR (400 MHz, DMSO-d$_6$) δ ppm 5.84 (br. s., 3 H) 7.65-7.77 (m, 1 H) 7.90 (t, J = 7.83 Hz, 1 H) 8.17-8.29 (m, 2 H) 8.36 (d, J = 7.81 Hz, 1 H) 8.49 (d, J = 7.91 Hz, 1 H) 8.74 (s, 1 H) 8.80 (d, J = 3.81 Hz, 1 H); LCMS (M/Z): M + H$^+$ 361. | 361 | 1.18 |
| 49 | N-[3-(2-pyridyl)-1,2,4-thiadiazol-5-yl]isoquinoline-5-carboxamide<br>$^1$H NMR (400 MHz, DMSO-d$_6$) δ ppm 7.65-7.75 (m, 1 H) 8.12 (t, J = 7.71 Hz, 1 H) 8.23 (t, J = 7.25 Hz, 1 H) 8.38 (d, J = 7.42 Hz, 1 H) 8.71 (d, J = 7.22 Hz, 1 H) 8.73-8.82 (m, 3 H) 8.86 (d, J = 6.83 Hz, 1 H) 10.00 (s, 1 H); LCMS (M/Z): M + H$^+$ 334. | 334 | 1.15 |
| 50 | 3-chloro-4-(4-methylpiperazin-1-yl)-N-[3-(2-pyridyl)-1,2,4-thiadiazol-5-yl]benzamide<br>$^1$H NMR (400 MHz, DMSO-d$_6$) δ ppm 2.83 (d, J = 4.39 Hz, 3 H) 3.11-3.36 (m, 4 H) 3.52 (d, J = 11.32 Hz, 2 H) 3.62 (d, J = 11.96 Hz, 2 H) 7.39 (d, J = 8.59 Hz, 1 H) 7.65 (dd, J = 6.93, 5.47 Hz, 1 H) 8.08-8.22 (m, 2 H) 8.25-8.38 (m, 2 H) 8.77 (d, J = 4.49 Hz, 1 H) 11.43 (br. s., 1 H); LCMS (M/Z): M + H$^+$ 415. | 415 | 1.07 |
| 51 | methyl 4-[[3-(2-pyridyl)-1,2,4-thiadiazol-5-yl]carbamoyl]benzoate<br>$^1$H NMR (400 MHz, DMSO-d$_6$) δ ppm 3.91 (s, 3 H) 7.52-7.65 (m, 1 H) 8.08 (t, J = 7.71 Hz, 1 H) 8.14 (d, J = 8.49 Hz, 2 H) 8.22-8.38 (m, 3 H) 8.76 (br. s., 1 H); LCMS (M/Z): M + H$^+$ 341. | 341 | 1.6 |
| 52 | 4-(diethylsulfamoyl)-N-[3-(2-pyridyl)-1,2,4-thiadiazol-5-yl]benzamide<br>$^1$H NMR (400 MHz, DMSO-d$_6$) δ ppm 1.07 (t, J = 7.10 Hz, 6 H) 3.23 (q = J = 7.11 Hz, 4 H) 7.59 (br. s., 1 H) 8.00 (s, 2 H) 8.06 (t, J = 7.69 Hz, 1 H) 8.29 (br. s., 1 H) 8.37 (d, J = 8.54 Hz, 2 H) 8.75 (br. s., 1 H); LCMS (M/Z): M + H$^+$ 418. | 418 | 1.64 |
| 53 | 4-methyl-N-[3-(2-pyridyl)-1,2,4-thiadiazol-5-yl]thiophene-2-carboxamide<br>$^1$H NMR (400 MHz, DMSO-d$_6$) δ ppm 2.25 (s, 3 | 3 | 1.54 |

TABLE 2-continued

| Cpd. | Name | Mass found | LCMS retention time |
|---|---|---|---|
| | H) 7.49 (ddd, J = 7.55, 4.75, 1.12 Hz, 1 H) 7.65 (s, 1 H) 7.95 (td, J = 7.74, 1.81 Hz, 1 H) 8.13 (d, J = 1.02 Hz, 1 H) 8.20 (d, J = 7.91 Hz, 1 H) 8.62-8.74 (m, 1 H) 13.75 (br. s., 1 H); LCMS (M/Z): M + H$^+$ 303 | | |
| 54 | 3-chloro-4-fluoro-N-[3-(2-pyridyl)-1,2,4-thiadiazol-5-yl]benzamide<br>$^1$H NMR (400 MHz, DMSO-d$_6$) δ ppm 7.53 (ddd, J = 7.55, 4.75, 1.12 Hz, 1 H) 7.67 (t, J = 8.91 Hz, 1 H) 7.99 (td, J = 7.74, 1.81 Hz, 1 H) 8.16-8.28 (m, 2 H) 8.46 (dd, J = 7.03, 2.25 Hz, 1 H) 8.67-8.76 (m, 1 H) 13.89 (br. s., 1 H); LCMS (M/Z): M + H$^+$ 335. | 335 | 1.81 |
| 55 | 2-fluoro-3-methoxy-N-[3-(2-pyridyl)-1,2,4-thiadiazol-5-yl]benzamide<br>$^1$H NMR (400 MHz, DMSO-d$_6$) δ ppm 3.92 (s, 3 H) 7.28-7.34 (m, 1 H) 7.35-7.40 (m, 1 H) 7.46 (td, J = 8.08, 1.81 Hz, 1 H) 7.52 (ddd, J = 7.55, 4.75, 1.12 Hz, 1 H) 7.99 (td, J = 7.75, 1.78 Hz, 1 H) 8.23 (d, J = 7.91 Hz, 1 H) 8.66-8.77 (m, 1 H) 13.71 (br. s., 1 H); LCMS (M/Z): M + H$^+$ 331. | 331 | 1.41 |
| 56 | N-[3-(2-pyridyl)-1,2,4-thiadiazol-5-yl]-3-(trifluoromethyl)benzamide<br>$^1$H NMR (400 MHz, DMSO-d$_6$) δ ppm 7.52 (ddd, J = 7.55, 4.75, 1.17 Hz, 1 H) 7.85 (t, J = 7.83 Hz, 1 H) 7.99 (td, J = 7.75, 1.78 Hz, 1 H) 8.08 (d, J = 7.86 Hz, 1 H) 8.25 (dt, J = 7.87, 0.97 Hz, 1 H) 8.46 (d, J = 7.96 Hz, 1 H) 8.59 (s, 1 H) 8.68-8.77 (m, 1 H) 14.01 (s, 1 H); LCMS (M/Z): M + H$^+$ 351. | 351 | 1.8 |
| 57 | 2,5-dimethyl-N-[3-(2-pyridyl)-1,2,4-thiadiazol-5-yl]furan-3-carboxamide<br>$^1$H NMR (400 MHz, DMSO-d$_6$) δ ppm 2.28 (s,, H) 2.59 (s, 3 H) 6.92 (d, J = 0.73 Hz, 1 H) 7.51 (ddd, J = 7.55, 4.75, 1.12 Hz, 1 H) 7.97 (td, J = 7.74, 1.81 Hz, 1 H) 8.23 (d, J = 7.86 Hz, 1 H) 8.68-8.75 (m, 1 H) 13.24 (s, 1 H); LCMS (M/Z): M + H$^+$ 301. | 301 | 1.64 |
| 58 | 4-tert-butyl-N-[3-(2-pyridyl)-1,2,4-thiadiazol-5-yl]benzamide<br>$^1$H NMR (400 MHz, DMSO-d$_6$) δ ppm 1.29 (s, 9 H) 7.49 (ddd, J = 7.54, 4.76, 1.17 Hz, 1 H) 7.54-7.62 (m, 2 H) 7.95 (td, J = 7.74, 1.81 Hz, 1 H) 8.08-8.16 (m, 1 H) 8.19-8.25 (m, 2 H) 8.65-8.72 (m, 1 H) 13.68 (br. s., 1 H); LCMS (M/Z): M + H$^+$ 339. | 339 | 1.97 |
| 59 | N-[3-(2-pyridyl)-1,2,4-thiadiazol-5-yl]-1,3-benzodioxole-5-carboxamide<br>$^1$H NMR (400 MHz, DMSO-d$_6$) δ ppm 6.15 (s, 2 H) 7.09 (d, J = 8.25 Hz, 1 H) 7.48 (ddd, J = 7.54, 4.78, 1.10 Hz, 1 H) 7.70 (d, J = 1.76 Hz, 1 H) 7.81 (dd, J = 8.25, 1.81 Hz, 1 H) 7.94 (td, J = 7.72, 1.78 Hz, 1 H) 8.21 (d, J = 7.86 Hz, 1 H) 8.68 (dt, J = 4.73, 0.83 Hz, 1 H) 13.55 (br. s., 1 H); LCMS (M/Z): M + H$^+$ 327. | 327 | 1.48 |
| 60 | 3,4-dichloro-N-[3-(2-pyridyl)-1,2,4-thiadiazol-5-yl]benzamide<br>$^1$H NMR (400 MHz, DMSO-d$_6$) δ ppm 7.52 (ddd, J = 7.54, 4.76, 1.17 Hz, 1 H) 7.88 (d, J = 8.44 Hz, 1 H) 7.98 (td, J = 7.74, 1.81 Hz, 1 H) 8.13 (dd, J = 8.42, 2.12 Hz, 1 H) 8.18-8.27 (m, 1 H) 8.45 (d, J = 2.05 Hz, 1 H) 8.67-8.76 (m, 1 H) 13.91 (br. s., 1 H); LCMS (M/Z): M + H$^+$ 351. | 351 | 1.96 |
| 61 | N-[3-(2-pyridyl)-1,2,4-thiadiazol-5-yl]-3,5-bis(trifluoromethyl)benzamide<br>$^1$H NMR (400 MHz, DMSO-d$_6$) δ ppm 7.52 (ddd, J = 7.54, 4.76, 1.17 Hz, 1 H) 7.88 (d, J = 8.44 Hz, 1 H) 7.98 (td, J = 7.74, 1.81 Hz, 1 H) 8.13 (dd, J = 8.42, 2.12 Hz, 1 H) 8.18-8.27 (m, 1 H) 8.45 (d, J = 2.05 Hz, 1 H) 8.67-8.76 (m, 1 H) 13.91 (br. s., 1 H); LCMS (M/Z): M + H$^+$ 351. | 419 | 2.04 |
| 62 | 4-methoxy-N-[3-(2-pyridyl)-1,2,4-thiadiazol-5-yl]benzamide<br>$^1$H NMR (400 MHz, DMSO-d$_6$) δ ppm 3.87 (s, 3 H) 7.08-7.19 (m, 2 H) 7.52 (ddd, J = 7.54, 4.76, 1.17 Hz, 1 H) 7.98 (td, J = 7.74, 1.76 Hz, 1 H) 8.14-8.28 (m, 3 H) 8.68-8.76 (m, 1 H) 13.61 (s, 1 H); LCMS (M/Z): M + H$^+$ 313. | 313 | 1.49 |

TABLE 2-continued

| Cpd. | Name | Mass found | LCMS retention time |
|---|---|---|---|
| 63 | 4-phenoxy-N-[3-(2-pyridyl)-1,2,4-thiadiazol-5-yl]benzamide<br>$^1$H NMR (400 MHz, DMSO-d$_6$) δ ppm 7.11 (d, J = 8.83 Hz, 2 H) 7.16 (d, J = 7.66 Hz, 2 H) 7.23-7.31 (m, 1 H) 7.43-7.56 (m, 3 H) 7.98 (td, J = 7.75, 1.73 Hz, 1 H) 8.24 (d, J = 8.74 Hz, 3 H) 8.72 (d, J = 4.34 Hz, 1 H) 13.71 (br. s., 1 H); LCMS (M/Z): M + H$^+$ 375. | 375 | 1.93 |
| 64 | 4-fluoro-N-[3-(2-pyridyl)-1,2,4-thiadiazol-5-yl]-2-(trifluoromethyl)benzamide<br>$^1$H NMR (400 MHz, DMSO-d$_6$) δ ppm 7.52 (ddd, J = 7.55, 4.75, 1.12 Hz, 1 H) 7.77 (td, J = 8.44, 2.54 Hz, 1 H) 7.90 (dd, J = 9.18, 2.54 Hz, 1 H) 7.94-8.08 (m, 2 H) 8.22 (d, J = 7.91 Hz, 1 H) 8.66-8.77 (m, 1 H) 13.95 (br. s., 1 H); LCMS (M/Z): M + H$^+$ 367. | 369 | 1.56 |
| 65 | N-[3-(2-pyridyl)-1,2,4-thiadiazol-5-yl]benzamide<br>$^1$H NMR (400 MHz, DMSO-d$_6$) δ ppm 7.52 (ddd, J = 7.53, 4.77, 1.12 Hz, 1 H) 7.56-7.66 (m, 2 H) 7.67-7.76 (m, 1 H) 7.99 (td, J = 7.74, 1.76 Hz, 1 H) 8.15-8.23 (m, 2 H) 8.25 (d, J = 7.86 Hz, 1 H) 8.65-8.78 (m, 1 H) 13.79 (br. s., 1 H); LCMS (M/Z): M + H$^+$ 283. | 283 | 1.46 |
| 66 | 4-[[3-(2-pyridyl)-1,2,4-thiadiazol-5-yl]carbamoyl]benzoic acid<br>$^1$H NMR (400 MHz, DMSO-d$_6$) δ ppm 7.45 (ddd, J = 7.52, 4.76, 1.10 Hz, 1 H) 7.87-7.97 (m, 1 H) 8.03 (d, J = 8.49 Hz, 2 H) 8.16-8.34 (m, 3 H) 8.62-8.72 (m, 1 H); LCMS (M/Z): M + H$^+$ 327. | 327 | 1.35 |
| 67 | 4-iodo-N-[3-(2-pyridyl)-1,2,4-thiadiazol-5-yl]benzamide<br>$^1$H NMR (400 MHz, DMSO-d$_6$) δ ppm 7.52 (ddd, J = 7.54, 4.76, 1.17 Hz, 1 H) 7.90-8.05 (m, 5 H) 8.24 (d, J = 7.86 Hz, 1 H) 8.69-8.75 (m, 1 H) 13.85 (br. s., 1 H); LCMS (M/Z): M + H$^+$ 408. | 408 | 1.79 |
| 68 | 4-morpholino-N-[3-(2-pyridyl)-1,2,4-thiadiazol-5-yl]benzamide<br>$^1$H NMR (400 MHz, DMSO-d$_6$) δ ppm 3.24-3.40 (m, 4 H) 3.67-3.81 (m, 4 H) 7.06 (d, J = 9.13 Hz, 2 H) 7.51 (ddd, J = 7.53, 4.75, 1.15 Hz, 1 H) 7.97 (td, J = 7.74, 1.81 Hz, 1 H) 8.11 (d, J = 8.98 Hz, 2 H) 8.24 (d, J = 7.86 Hz, 1 H) 8.67-8.75 (m, 1 H) 13.41 (br. s., 1 H); LCMS (M/Z): M + H$^+$ 368. | 368 | 1.44 |
| 69 | 4-(morpholine-4-carbonyl)-N-[3-(2-pyridyl)-1,2,4-thiadiazol-5-yl]benzamide<br>$^1$H NMR (400 MHz, DMSO-d$_6$) δ ppm 3.44-3.84 (m, 6 H) 7.45-7.55 (m, 1 H) 7.62 (d, J = 8.35 Hz, 2 H) 7.99 (td, J = 7.74, 1.71 Hz, 1 H) 8.16-8.34 (m, 3 H) 8.72 (d, J = 4.05 Hz, 1 H) 13.85 (br. s., 1 H); LCMS (M/Z): M + H$^+$ 396. | 396 | 1.21 |
| 70 | tert-butyl 4-[4-[[3-(2-pyridyl)-1,2,4-thiadiazol-5-yl]carbamoyl]benzoyl]piperazine-1-carboxylate<br>$^1$H NMR (400 MHz, DMSO-d$_6$) δ ppm 1.41 (s, 9 H) 3.35 (br. s., 2 H) 3.43 (br. s., 2 H) 3.62 (br. s., 2 H) 7.53 (ddd, J = 7.54, 4.76, 1.07 Hz, 1 H) 7.63 (d, J = 8.40 Hz, 2 H) 7.99 (td, J = 7.72, 1.78 Hz, 1 H) 8.21-8.30 (m, 3 H) 8.73 (d, J = 4.00 Hz, 1 H) 13.90 (br. s., 1 H); LCMS (M/Z): M + H$^+$ 495. | 495 | 1.66 |
| 71 | tert-butyl 4-[[4-[[3-(2-pyridyl)-1,2,4-thiadiazol-5-yl]carbamoyl]benzoyl]amino]piperidine-1-carboxylate<br>$^1$H NMR (400 MHz, DMSO-d$_6$) δ ppm 1.31-1.53 (m, 11 H) 1.81 (d, J = 9.57 Hz, 2 H) 2.86 (br. s., 2 H) 3.86-4.08 (m, 3 H) 7.53 (ddd, J = 7.55, 4.77, 1.10 Hz, 1 H) 7.94-8.07 (m, 3 H) 8.19-8.30 (m, 3 H) 8.50 (d, J = 7.81 Hz, 1 H) 8.73 (d, J = 4.00 Hz, 1 H) 13.91 (br. s., 1 H); LCMS (M/Z): M + H$^+$ 509. | 509 | 1.73 |
| 72 | 4-(piperidine-1-carbonyl)-N-[3-(2-pyridyl)-1,2,4-thiadiazol-5-yl]benzamide<br>$^1$H NMR (400 MHz, DMSO-d$_6$) δ ppm 1.38-1.71 (m, 6 H) 3.25 (br. s., 2 H) 3.61 (br. s., 2 H) 7.47-7.54 (m, 1 H) 7.57 (d, J = 8.30 Hz, 2 H) 7.99 (td, J = 7.72, 1.73 Hz, 1 H) 8.19-8.27 (m, 3 H) 8.73 (d, J = 4.10 Hz, 1 H) 13.81 (br. s., 1 H); LCMS (M/Z): M + H$^+$ 394. | 394 | 1.54 |

TABLE 2-continued

| Cpd. | Name | Mass found | LCMS retention time |
|---|---|---|---|
| 73 | 4-(piperazine-1-carbonyl)-N-[3-(2-pyridyl)-1,2,4-thiadiazol-5-yl]benzamide<br>$^1$H NMR (400 MHz, DMSO-d$_6$) δ ppm 3.15-3.25 (m, 4 H) 3.77 (br. s., 4 H) 7.47 (ddd, J = 7.47, 4.81, 1.10 Hz, 1 H) 7.53 (d, J = 8.30 Hz, 2 H) 7.95 (td, J = 7.71, 1.76 Hz, 1 H) 8.14-8.30 (m, 3 H) 8.63-8.74 (m, 1 H): LCMS (M/Z): M + H$^+$ 395 | 395 | 0.69 |
| 74 | N1-[3-(2-pyridyl)-1,2,4-thiadiazol-5-yl]terephthalamide<br>$^1$H NMR (400 MHz, DMSO-d$_6$) δ ppm 7.53 (ddd, J = 7.54, 4.76, 1.12 Hz, 1 H) 7.61 (s, 1 H) 8.00 (td, J = 7.74, 1.76 Hz, 1 H) 8.05 (d, J = 8.54 Hz, 2 H) 8.17 (s, 1 H) 8.21-8.31 (m, 3 H) 8.68-8.77 (m, 1 H) 13.90 (br. s., 1 H); LCMS (M/Z): M + H$^+$ 326. | 326 | |
| 75 | 4-(2-pyridylamino)-N-[3-(2-pyridyl)-1,2,4-thiadiazol-5-yl]benzamide<br>$^1$H NMR (400 MHz, DMSO-d$_6$) δ ppm 7.50 (ddd, J = 7.49, 4.76, 0.98 Hz, 1 H) 7.66 (ddd, J = 8.49, 7.00, 1.93 Hz, 1 H) 7.88 (d, J = 8.88 Hz, 2 H) 7.97 (td, J = 7.72, 1.73 Hz, 1 H) 8.14 (d, J = 8.88 Hz, 2 H) 8.21-8.30 (m, 3 H) 8.71 (d, J = 3.95 Hz, 1 H) 9.57 (s, 1 H); LCMS (M/Z): M + H$^+$ 375. | 375 | 1.36 |
| 76 | tert-butyl 4-[4-[[3-(2-pyridyl)-1,2,4-thiadiazol-5-yl]carbamoyl]anilino]piperidine-1-carboxylate<br>$^1$H NMR (400 MHz, DMSO-d$_6$) δ ppm 1.17-1.33 (m, 2 H) 1.34-1.50 (m, 9 H) 1.81-1.96 (m, 2 H) 2.93 (br. s., 2 H) 3.51-3.66 (m, 1 H) 3.90 (d, J = 13.23 Hz, 2 H) 6.60 (s, 1 H) 6.71 (s, 2 H) 7.51 (ddd, J = 7.55, 4.77, 1.15 Hz, 1 H) 7.90-8.05 (m, 3 H) 8.24 (s, 1 H) 8.66-8.75 (m, 1 H); LCMS (M/Z): M + H$^+$ 481. | 481 | 1.82 |
| 77 | 4-phenyl-N-[3-(2-pyridyl)-1,2,4-thiadiazol-5-yl]benzamide<br>$^1$H NMR (400 MHz, DMSO-d$_6$) δ ppm 7.40-7.48 (m, 1 H) 7.49-7.56 (m, 3 H) 7.77-7.84 (m, 2 H) 7.92 (d, J = 8.54 Hz, 2 H) 8.00 (td, J = 7.72, 1.78 Hz, 1 H) 8.26 (d, J = 7.86 Hz, 1 H) 8.31 (d, J = 8.54 Hz, 2 H) 8.70-8.77 (m, 1 H) 13.84 (s, 1 H); LCMS (M/Z): M + H$^+$ 359. | 359 | 1.91 |
| 78 | 4-piperazin-1-yl-N-[3-(2-pyridyl)-1,2,4-thiadiazol-5-yl]benzamide<br>$^1$H NMR (400 MHz, DMSO-d$_6$) δ ppm 3.24 (br. s., 4 H) 3.53-3.67 (m, 4 H) 7.14 (d, J = 9.13 Hz, 2 H) 7.53 (dd, J = 6.61, 4.86 Hz, 1 H) 8.00 (td, J = 7.74, 1.71 Hz, 1 H) 8.14 (d, J = 8.93 Hz, 2 H) 8.25 (d, J = 7.91 Hz, 1 H) 8.72 (d, J = 4.64 Hz, 1 H) 8.88 (br. s., 2 H) 13.49 (br. s., 1 H); LCMS (M/Z): M + H$^+$ 367. | 367 | 0.79 |
| 79 | 4-(4-piperidylamino)-N-[3-(2-pyridyl)-1,2,4-thiadiazol-5-yl]benzamide<br>$^1$H NMR (400 MHz, DMSO-d$_6$) δ ppm 1.59 (d, J = 10.69 Hz, 2 H) 2.07 (d, J = 12.25 Hz, 2 H) 3.05 (t, J = 10.54 Hz, 2 H) 3.31 (d, J = 11.52 Hz, 2 H) 3.65 (br. s., 1 H) 6.65 (d, J = 7.47 Hz, 1 H) 6.71 (d, J = 8.69 Hz, 2 H) 7.49 (m, J = 6.64, 4.88 Hz, 1 H) 7.96 (td, J = 7.75, 1.64 Hz, 1 H) 8.02 (s, 2 H) 8.23 (d, J = 7.86 Hz, 1 H) 8.34 (s, 1 H) 8.71 (d, J = 4.20 Hz, 1 H); LCMS (M/Z): M + H$^+$ 381. | 381 | 0.8 |
| 80 | tert-butyl 4-[4-[[3-(2-pyridyl)-1,2,4-thiadiazol-5-yl]carbamoyl]phenyl]piperazine-1-carboxylate<br>$^1$H NMR (400 MHz, DMSO-d$_6$) δ ppm 1.43 (s, 9 H) 3.38 (dd, J = 6.42, 3.59 Hz, 4 H) 3.43-3.49 (m, 4 H) 7.05 (d, J = 9.08 Hz, 2 H) 7.50 (ddd, J = 7.50, 4.80, 0.98 Hz, 1 H) 7.97 (td, J = 7.72, 1.73 Hz, 1 H) 8.10 (d, J = 8.98 Hz, 2 H) 8.25 (s, 1 H) 8.71 (d, J = 4.05 Hz, 1 H); LCMS (M/Z): M + H$^+$ 467. | 467 | 1.85 |
| 81 | 3-chloro-2-fluoro-N-[3-(2-pyridyl)-1,2,4-thiadiazol-5-yl]-5-(trifluoromethyl)benzamide<br>$^1$H NMR (400 MHz, DMSO-d$_6$) δ ppm 7.46-7.55 (m, 1 H) 7.98 (td, J = 7.74, 1.76 Hz, 1 H) 8.23 (d, J = 7.91 Hz, 1 H) 8.31 (dd, J = 5.49, 1.98 Hz, 1 H) 8.38 (dd, J = 6.08, 1.98 Hz, 1 H) 8.68-8.75 (m, 1 H); LCMS (M/Z): M + H$^+$ 403. | 403 | 1.87 |
| 82 | N-[3-(2-pyridyl)-1,2,4-thiadiazol-5-yl]-4-(1,1,2,2-tetrafluoroethoxy)benzamide<br>$^1$H NMR (400 MHz, DMSO-d$_6$) δ ppm | 399 | 1.74 |

TABLE 2-continued

| Cpd. | Name | Mass found | LCMS retention time |
|---|---|---|---|
| | 6.68-7.05 (m, 1 H) 7.45-7.57 (m, 3 H) 7.99 (td, J = 7.75, 1.73 Hz, 1 H) 8.24 (s, 1 H) 8.28-8.36 (m, 2 H) 8.68-8.77 (m, 1 H) 13.88 (br. s., 1 H); LCMS (M/Z): M + H$^+$ 399. | | |
| 83 | 2-methoxy-N-[3-(2-pyridyl)-1,2,4-thiadiazol-5-yl]-4-(trifluoromethoxy)benzamide<br>$^1$H NMR (400 MHz, DMSO-d$_6$) δ ppm 3.92 (s, 3 H) 7.08 (dd, J = 8.52, 0.85 Hz, 1 H) 7.21 (d, J = 1.81 Hz, 1 H) 7.48 (ddd, J = 7.54, 4.76, 1.12 Hz, 1 H) 7.82 (d, J = 8.54 Hz, 1 H) 7.95 (td, J = 7.74, 1.76 Hz, 1 H) 8.20 (d, J = 7.91 Hz, 1 H) 8.69 (dt, J = 4.75, 0.85 Hz, 1 H) 13.09 (br. s., 1 H); LCMS (M/Z): M + H$^+$ 397. | 397 | 1.8 |
| 84 | N-[3-(2-pyridyl)-1,2,4-thiadiazol-5-yl]-5-(trifluoromethyl)furan-2-carboxamide<br>$^1$H NMR (400 MHz, DMSO-d$_6$) δ ppm 7.46-7.59 (m, 2 H) 7.86 (d, J = 3.51 Hz, 1 H) 7.99 (td, J = 7.74, 1.76 Hz, 1 H) 8.24 (d, J = 7.86 Hz, 1 H) 8.68-8.77 (m, 1 H); LCMS (M/Z): M + H$^+$ 341. | 341 | 1.55 |
| 85 | N-[3-(2-pyridyl)-1,2,4-thiadiazol-5-yl]-5-(trifluoromethyl)thiophene-2-carboxamide<br>$^1$H NMR (400 MHz, DMSO-d$_6$) δ ppm 7.50 (ddd, J = 7.49, 4.81, 0.93 Hz, 1 H) 7.91 (dd, J = 4.03, 1.00 Hz, 1 H) 7.96 (td, J = 7.74, 1.71 Hz, 1 H) 8.21 (d, J = 7.86 Hz, 1 H) 8.33 (dd, J = 3.90, 1.07 Hz, 1 H) 8.70 (d, J = 4.30 Hz, 1 H); LCMS: M + H$^+$ 357. | 357 | 1.84 |
| 86 | 4-formyl-N-[3-(2-pyridyl)-1,2,4-thiadiazol-5-yl]benzamide<br>$^1$H NMR (400 MHz, DMSO-d$_6$) δ ppm 7.53 (ddd, J = 7.54, 4.76, 1.12 Hz, 1 H) 7.99 (td, J = 7.75, 1.78 Hz, 1 H) 8.06-8.14 (m, 2 H) 8.26 (d, J = 7.86 Hz, 1 H) 8.37 (d, J = 8.25 Hz, 2 H) 8.69-8.76 (m, 1 H) 10.14 (s, 1 H) 14.02 (s, 1 H); LCMS (M/Z): M + H$^+$ 311. | 311 | 1.34 |
| 87 | 4-[hydroxy(phenyl)methyl]-N-[3-(2-pyridyl)-1,2,4-thiadiazol-5-yl]benzamide<br>$^1$H NMR (400 MHz, DMSO-d$_6$) δ ppm 5.81 (s, 1 H) 6.09 (br. s., 1 H) 7.17-7.26 (m, 1 H) 7.32 (t, J = 7.54 Hz, 2 H) 7.42 (d, J = 7.22 Hz, 2 H) 7.51 (dd, J = 7.35, 4.95 Hz, 1 H) 7.59 (d, J = 8.20 Hz, 2 H) 7.97 (td, J = 7.74, 1.56 Hz, 1 H) 8.14 (d, J = 8.35 Hz, 2 H) 8.24 (d, J = 7.86 Hz, 1 H) 8.71 (d, J = 4.20 Hz, 1 H) 13.65 (br. s., 1 H); LCMS (M/Z): M + H$^+$ 389. | 389 | 1.62 |
| 88 | 3-bromo-N-[3-(2-pyridyl)-1,2,4-thiadiazol-5-yl]benzamide<br>$^1$H NMR (400 MHz, DMSO-d$_6$) δ ppm 7.53 (ddd, J = 7.54, 4.76, 1.12 Hz, 1 H) 7.58 (t, J = 7.93 Hz, 1 H) 7.88-7.94 (m, 1 H) 7.99 (td, J = 7.74, 1.81 Hz, 1 H) 8.15-8.21 (m, 1 H) 8.25 (d, J = 7.91 Hz, 1 H) 8.41 (t, J = 1.78 Hz, 1 H) 8.73 (dt, J = 4.73, 0.83 Hz, 1 H) 13.89 (br. s., 1 H); LCMS (M/Z): M + H$^+$ 363. | 363 | 1.76 |
| 89 | 4-benzyl-N-[3-(2-pyridyl)-1,2,4-thiadiazol-5-yl]benzamide<br>$^1$H NMR (400 MHz, DMSO-d$_6$) δ ppm 4.06 (s, 2 H) 7.14-7.24 (m, 1 H) 7.25-7.36 (m, 4 H) 7.46 (d, J = 8.30 Hz, 2 H) 7.56 (br. s., 1 H) 8.01 (t, J = 7.71 Hz, 1 H) 8.14 (d, J = 8.30 Hz, 2 H) 8.27 (br. s., 1 H) 8.74 (br. s., 1 H) 13.72 (br. s., 1 H); LCMS (M/Z): M + H$^+$ 373. | 373 | 1.91 |
| 90 | N4-[3-(2-pyridyl)-1,2,4-thiadiazol-5-yl]terephthalamide<br>$^1$H NMR (400 MHz, DMSO-d$_6$) δ ppm 7.53 (ddd, J = 7.54, 4.76, 1.12 Hz, 1 H) 7.61 (s, 1 H) 8.00 (td, J = 7.74, 1.76 Hz, 1 H) 8.05 (d, J = 8.54 Hz, 2 H) 8.17 (s, 1 H) 8.21-8.31 (m, 3 H) 8.68-8.77 (m, 1 H) 13.90 (br. s., 1 H); LCMS (M/Z): M + H$^+$ 326. | 326 | 1.04 |
| 91 | 4-bromo-N-[3-(2-pyridyl)-1,2,4-thiadiazol-5-yl]benzamide<br>$^1$H NMR (400 MHz, DMSO-d$_6$) δ ppm 7.53 (ddd, J = 7.54, 4.73, 1.15 Hz, 1 H) 7.78-7.87 (m, 2 H) 7.99 (td, J = 7.74, 1.81 Hz, 1 H) 8.08-8.17 (m, 2 H) 8.19-8.28 (m, 1 H) 8.64-8.78 (m, 1 H) 13.87 (s, 1 H); LCMS (M/Z): M + H$^+$ 361. | 361 | 1.72 |

TABLE 2-continued

| Cpd. | Name | Mass found | LCMS retention time |
|---|---|---|---|
| 92 | 3-chloro-N-[3-(2-pyridyl)-1,2,4-thiadiazol-5-yl]-4-(trifluoromethoxy)benzamide<br>$^1$H NMR (400 MHz, DMSO-d$_6$) δ ppm 7.52 (dd, J = 6.66, 4.86 Hz, 1 H) 7.81 (dd, J = 8.61, 1.24 Hz, 1 H) 7.99 (td, J = 7.72, 1.64 Hz, 1 H) 8.17-8.33 (m, 2 H) 8.51 (d, J = 2.10 Hz, 1 H) 8.72 (d, J = 4.15 Hz, 1 H); LCMS (M/Z): M + H$^+$ 401. | 401 | 1.98 |
| 93 | N-[3-(4-phenyl-2-pyridyl)-1,2,4-thiadiazol-5-yl]-4-(trifluoromethyl)benzamide<br>$^1$H NMR (400 MHz, DMSO-d$_6$) δ ppm 7.49-7.55 (m, 1 H) 7.56-7.63 (m, 2 H) 7.80-7.91 (m, 3 H) 7.97 (d, J = 8.35 Hz, 2 H) 8.39 (d, J = 8.10 Hz, 2 H) 8.53 (d, J = 1.22 Hz, 1 H) 8.78 (d, J = 5.12 Hz, 1 H); LCMS (M/Z): M + H$^+$ 427. | 427 | 2.09 |
| 94 | 4-(trifluoromethyl)-N-[3-[5-(trifluoromethyl)-2-pyridyl]-1,2,4-thiadiazol-5-yl]benzamide<br>$^1$H NMR (400 MHz, DMSO-d$_6$) δ ppm 7.97 (d, J = 8.35 Hz, 2 H) 8.30-8.50 (m, 4 H) 9.11 (s, 1 H); LCMS (M/Z): M + H$^+$ 419. | 419 | 2.03 |
| 95 | N4-phenyl-N1-[3-(2-pyridyl)-1,2,4-thiadiazol-5-yl]terephthalamide<br>$^1$H NMR (400 MHz, DMSO-d$_6$) δ ppm 7.09-7.20 (m, 1 H) 7.33-7.43 (m, 2 H) 7.48-7.58 (m, 1 H) 7.75-7.84 (m, 2 H) 8.00 (td, J = 7.74, 1.76 Hz, 1 H) 8.15 (d, J = 8.54 Hz, 2 H) 8.27 (d, J = 7.91 Hz, 1 H) 8.34 (d, J = 8.59 Hz, 2 H) 8.74 (d, J = 4.15 Hz, 1 H) 10.46 (s, 1 H) 13.96 (br. s., 1 H); LCMS (M/Z): M + H$^+$ 402. | 402 | |
| 96 | N-[3-(2-pyridyl)-1,2,4-thiadiazol-5-yl]-2-(trifluoromethyl) benzamide<br>$^1$H NMR (400 MHz, DMSO-d$_6$) δ ppm 7.53 (ddd, J = 7.55, 4.77, 1.15 Hz, 1 H) 7.77-7.96 (m, 4 H) 7.99 (td, J = 7.74, 1.81 Hz, 1 H) 8.18-8.26 (m, 1 H) 8.67-8.77 (m, 1 H) 13.92 (br. s., 1 H); LCMS (M/Z): M + H$^+$ 351. | 351 | |
| 97 | 2-fluoro-N-[3-(2-pyridyl)-1,2,4-thiadiazol-5-yl]-2-(trifluoromethoxy) benzamide<br>$^1$H NMR (400 MHz, DMSO-d$_6$) δ ppm 7.46 (dd, J = 8.69, 1.07 Hz, 1 H) 7.53 (ddd, J = 7.57, 4.76, 1.15 Hz, 1 H) 7.66 (dd, J = 10.79, 1.56 Hz, 1 H) 7.99 (td, J = 7.74, 1.76 Hz, 1 H) 8.04 (t, J = 8.35 Hz, 1 H) 8.19-8.28 (m, 1 H) 8.69-8.77 (m, 1 H) 13.82 (br. s., 1 H); LCMS (M/Z): M + H$^+$ 385. | 385 | |
| 98 | N-[3-(2-pyridyl)-1,2,4-thiadiazol-5-yl]-2-(trifluoromethoxy) benzamide<br>$^1$H NMR (400 MHz, DMSO-d$_6$) δ ppm 7.52 (ddd, J = 7.54, 4.76, 1.12 Hz, 1 H) 7.55-7.64 (m, 2 H) 7.70-7.81 (m, 1 H) 7.92 (dd, J = 7.61, 1.61 Hz, 1 H) 7.98 (td, J = 7.74, 1.81 Hz, 1 H) 8.23 (d, J = 7.86 Hz, 1 H) 8.72 (dd, J = 4.71, 0.76 Hz, 1 H) 13.84 (br. s., 1 H); LCMS (M/Z): M + H$^+$ 367. | 367 | |
| 99 | N-[3-(2-pyridyl)-1,2,4-thiadiazol-5-yl]-3-(trifluoromethoxy) benzamide<br>$^1$H NMR (400 MHz, DMSO-d$_6$) δ ppm 7.52 (ddd, J = 7.54, 4.76, 1.12 Hz, 1 H) 7.68-7.73 (m, 1 H) 7.73-7.79 (m, 1 H) 7.99 (td, J = 7.74, 1.81 Hz, 1 H) 8.18 (s, 1 H) 8.21-8.28 (m, 2 H) 8.67-8.76 (m, 1 H) 13.97 (br. s., 1 H); LCMS (M/Z): M + H$^+$ 367. | 367 | |
| 100 | 4-(4-fluorophenoxy)-N-[3-(2-pyridyl)-1,2,4-thiadiazol-5-yl] benzamide<br>$^1$H NMR (400 MHz, DMSO-d$_6$) δ ppm 7.08 (d, J = 8.83 Hz, 2 H) 7,17-7.25 (m, 2 H) 7.26-7.37 (m, 2 H) 7.49 (dd, J = 6.56, 4.81 Hz, 1 H) 7.96 (td, J = 7.72, 1.68 Hz, 1 H) 8.19-8.30 (m, 3 H) 8.70 (d, J = 4.05 Hz, 1 H); LCMS (M/Z): M + H$^+$ 393. | 393 | |
| 101 | 3-hydroxy-N-[3-(2-pyridyl)-1,2,4-thiadiazol-5-yl]-5-(trifluoromethyl) thiophene-2-carboxamide<br>$^1$H NMR (400 MHz, DMSO-d$_6$) δ ppm 7.40 (d, J = 0.98 Hz, 1 H) 7.58 (ddd, J = 7.54, 4.83, 1.05 Hz, 1 H) 8.03 (td, J = 7.75, 1.73 Hz, 1 H) 8.27 (4, J = 7.91 Hz, 1 H) 8.73 (dt, J = 4.78, 0.83 Hz, 1 H); LCMS (M/Z): M + H$^+$ 373. | 373 | |

TABLE 2-continued

| Cpd. | Name | Mass found | LCMS retention time |
|---|---|---|---|
| 102 | 4-(2,4-difluorophenoxy)-N-[3-(2-pyridyl)-1,2,4-thiadiazol-5-yl]benzamide<br>$^1$H NMR (400 MHz, DMSO-d$_6$) δ ppm 7.11 (d, J = 8.83 Hz, 2 H) 7.16-7.27 (m, 1 H) 7.37-7.62 (m, 3 H) 7.97 (td, J = 7.74, 1.76 Hz, 1 H) 8.17-8.29 (m, 3 H) 8.67-8.75 (m, 1 H) 13.72 (br. s., 1 H,); LCMS (M/Z): M + H$^+$ 411. | 411 | |
| 103 | N-[3-(2-pyridyl)-1,2,4-thiadiazol-5-yl]-4-[4-(trifluoromethyl)phenoxy] benzamide<br>$^1$H NMR (400 MHz, DMSO-d$_6$) δ ppm 7.25-7.30 (m, 2 H) 7.32 (4, J = 8.54 Hz, 2 H) 7.52 (ddd, J = 7.52, 4.78, 1.07 Hz, 1 H) 7.83 (d, J = 8.64 Hz, 2 H) 7.99 (td, J = 7.74, 1.76 Hz, 1 H) 8.25 (d, J = 7.91 Hz, 1 H) 8.27-8.34 (m, 2 H) 8.73 (d, J = 4.00 Hz, 1 H) 13.79 (s, 1 H); LCMS (M/Z): M + H$^+$ 443. | 443 | |
| 104 | N-[3-(2-pyridyl)-1,2,4-thiadiazol-5-yl]-3-[4-(trifluoromethyl)phenoxy]benzamide<br>$^1$H NMR (400 MHz, DMSO-d$_6$) δ ppm 7.26 (d, J = 8.49 Hz, 2 H) 7.45-7.56 (m, 2 H) 7.69 (t, J = 7.98 Hz, 1 H) 7.79 (d, J = 8.64 Hz, 2 H) 7.92-8.01 (m, 1 H) 8.03-8.11 (m, 1 H) 8.23 (d, J = 7.86 Hz, 1 H) 8.66-8.76 (m, 1 H) 13.85 (br. s., 1 H); LCMS (M/Z): M + H$^+$ 443. | 443 | |
| 105 | 3-(4-fluorophenoxy)-N-[3-(2-pyridyl)-1,2,4-thiadiazol-5-yl]benzamide<br>$^1$H NMR (400 MHz, DMSO-d$_6$) δ ppm 7.13-7.21 (m, 2 H) 7.25-7.32 (m, 2 H) 7.35 (ddd, J = 8.16, 2.48, 0.68 Hz, 1 H) 7.52 (ddd, J = 7.54, 4.76, 1.12 Hz, 1 H) 7.61 (t, J = 8.00 Hz, 1 H) 7.73-7.80 (m, 1 H) 7.92-8.03 (m, 2 H) 8.24 (d, J = 7.86 Hz, 1 H) 8.72 (dt, J = 4.70, 0.82 Hz, 1 H) 13.83 (br, s., 1 H); LCMS (M/Z); M + H$^+$ 393. | 393 | |
| 106 | 3-phenoxy-N-[3-(2-pyridyl)-1,2,4-thiadiazol-5-yl]benzamide<br>$^1$H NMR (400 MHz, DMSO-d$_6$) δ ppm 7.06-7.15 (m, 2 H) 7.17-7.27 (m, 1 H) 7.36 (ddd, J = 8.16, 2.45, 0.71 Hz, 1 H) 7.42-7.48 (m, 2 H) 7.52 (ddd, J = 7.54, 4.76, 1.12 Hz, 1 H) 7.62 (t, J = 8.00 Hz, 1 H) 7.76-7.84 (m, 1 H) 7.93-8.04 (m, 2 H) 8.24 (d, J = 7.86 Hz, 1 H) 8.68-8.75 (m, 1 H) 13.83 (s, 1 H); LCMS (M/Z): M + H$^+$ 375. | 375 | |
| 107 | N1-(4-piperidyl)-N4-[3-(2-pyridyl)-1,2,4-thiadiazol-5-yl]terephthalamide<br>$^1$H NMR (400 MHz, DMSO-d$_6$) δ ppm 1.71-1.89 (m, 2 H) 2.02 (d, J = 11.37 Hz, 2 H) 3.11 (t, J = 11.35 Hz, 2 H) 3.49 (d, J = 12.50 Hz, 2 H) 4.03-4.19 (m, 1 H) 7.42 (dd, J = 6.54, 4.98 Hz, 1 H) 7.84-7.96 (m, 3 H) 8.16-8.29 (m, 3 H) 8.49 (d, J = 7.47 Hz, 1 H) 8.67 (d, J = 4.20 Hz, 1 H); LCMS (M/Z): M + H$^+$ 409. | 409 | |
| 108 | N-[3-(5-piperazin-1-yl-2-pyridyl)-1,2,4-thiadiazol-5-yl]-4-(trifluoromethyl)benzamide<br>$^1$H NMR (400 MHz, DMSO-d$_6$) δ ppm 3.25 (br. s., 4 H) 3.43-3.60 (m, 4 H) 7.52 (d, J = 8.59 Hz, 1 H) 7.96 (d, J = 8.30 Hz, 2 H) 8.10 (d, J = 3.51 Hz, 1 H) 8.34 (d, J = 8.15 Hz, 2 H) 8.45 (br. s., 1 H) 8.89 (br. s., 2 H) 13.91 (br. s., 1 H); LCMS (M/Z): M + H$^+$ 435. | 435 | |
| 109 | 4-(4-piperidyloxy)-N-[3-(2-pyridyl)-1,2,4-thiadiazol-5-yl]pyridine-2-carboxamide<br>$^1$H NMR (400 MHz, DMSO-d$_6$) δ ppm 1.70-1.84 (m, 2 H) 1.90 (s, 3 H) 2.14 (d, J = 11.62 Hz, 2H) 3.10 (t, J = 9.18 Hz, 2 H) 3.24-3.36 (m, 2 H) 4.87 (d, J = 3.51 Hz, 1 H) 7.13 (dd, J = 5.59, 2.51 Hz, 1 H) 7.44 (dd, J = 6.91, 5.20 Hz, 1 H) 7.80 (d, J = 2.44 Hz, 1 H) 7.93 (t, J = 7.03 Hz, 1 H) 8.23 (d, J = 7.91 Hz, 1 H) 8.50 (d, J = 5.56 Hz, 1 H) 8.68 (d, J = 4.05 Hz, 1 H); LCMS (M/Z): M + H$^+$ 383. | 383 | |
| 110 | N-[3-(6-piperazin-1-yl-2-pyridyl)-1,2,4-thiadiazol-5-yl]-4-(trifluoromethyl)benzamide<br>$^1$H NMR (400 MHz, DMSO-d$_6$) δ ppm 3.19-3.26 (m, 4 H) 3.73-3.87 (m, 4 H) 7.00 (d, J = 8.40 Hz, 1 H) 7.61 (d, J = 7.32 Hz, 1 H) 7.69-7.80 (m, 1 H) 7.89 (d, J = 8.30 Hz, 2 H) 8.36 (d, J = 8.10 Hz, 2 H); LCMS (M/Z): M + H$^+$ 435. | 435 | |

TABLE 2-continued

| Cpd. | Name | Mass found | LCMS retention time |
|---|---|---|---|
| 111 | 4-(3-pyridyl)-N-[3-(2-pyridyl)-1,2,4-thiadiazol-5-yl] benzamide<br>$^1$H NMR (400 MHz, DMSO-d$_6$) δ ppm 7.48 (ddd, J = 7.44, 4.78, 0.95 Hz, 1 H) 7.53 (dd, J = 7.96, 4.78 Hz, 1 H) 7.88-8.00 (m, 3 H) 8.20 (dt, J = 8.00, 1.95 Hz, 1 H) 8.25 (d, J = 7.86 Hz, 1 H) 8.33 (d, J = 8.49 Hz, 2 H) 8.63 (dd, J = 4.76, 1.54 Hz, 1 H) 8.71 (d, J = 4.00 Hz, 1 H) 9.01 (d, J = 1.81 Hz, 1 H); LCMS (M/Z): M + H$^+$ 360. | 360 | |
| 112 | N-[3-(5-phenyl-2-pyridyl)-1,2,4-thiadiazol-5-yl]-4-(trifluoromethyl)benzamide<br>$^1$H NMR (400 MHz, DMSO-d$_6$) δ ppm 7.42-7.51 (m, 3 H) 7.55 (t, J = 7.49 Hz, 4 H) 7.78-7.87 (m, 2 H) 7.95 (d, J = 8.30 Hz, 2 H) 8.22-8.29 (m, 1 H) 8.30-8.35 (m, 1 H) 8.39 (d, J = 8.10 Hz, 2 H) 9.04 (d, J = 1.90 Hz, 1 H); LCMS (M/Z): M + H$^+$ 427. | 427 | |
| 113 | 4-(trifluoromethyl)-N-[3-(5-vinyl-2-pyridyl)-1,2,4-thiadiazol-5-yl]benzamide<br>$^1$H NMR (400 MHz, DMSO-d$_6$) δ ppm 5.50 (d, J = 11.23 Hz, 1 H) 6.09 (d, J = 17.77 Hz, 1 H) 6.87 (dd, J = 17.74, 11.10 Hz, 1 H) 7.98 (d, J = 8.35 Hz, 2 H) 8.12 (dd, J = 8.27, 2.17 Hz, 1 H) 8.23 (d, J = 8.20 Hz, 1 H) 8.38 (d, J = 8.15 Hz, 2 H) 8.79 (d, J = 1.95 Hz, 1 H); LCMS (M/Z): M + H$^+$ 377. | 377 | |
| 114 | N-[3-[5-(3,6-dihydro-2H-pyran-4-yl)-2-pyridyl]-1,2,4-thiadiazol-5-yl]-4-(trifluoromethyl)benzamide<br>$^1$H NMR (400 MHz, DMSO-d$_6$) δ ppm 2.53 (d, J = 1.66 Hz, 2 H) 3.86 (t, J = 5.42 Hz, 2 H) 4.27 (d, J = 2.64 Hz, 2 H) 6.53 (br. s., 1 H) 7.96 (d, J = 8.30 Hz, 2 H) 8.02 (dd, J = 8.27, 2.27 Hz, 1 H) 8.23 (s, 1 H) 8.39 (s, 2 H) 8.83 (d, J = 1.90 Hz, 1 H); LCMS (M/Z): M + H$^+$ 433. | 433 | |
| 115 | N-[3-(6-phenyl-2-pyridyl)-1,2,4-thiadiazol-5-yl]-4-(trifluoromethyl)benzamide<br>$^1$H NMR (400 MHz, DMSO-d$_6$) δ ppm 7.42-7.60 (m, 3 H) 7.99 (d, J = 7.57 Hz, 2 H) 8.09 (br. s., 2 H) 8.13-8.26 (m, 3 H) 8.39 (d, J = 7.61 Hz, 2 H) 14.03 (s, 1 H); LCMS (M/Z): M + H$^+$ 427. | 427 | |
| 116 | N-[3-[6-(3-pyridyl)-2-pyridyl]-1,2,4-thiadiazol-5-yl]-4-(trifluoromethyl)benzamide<br>$^1$H NMR (400 MHz, DMSO-d$_6$) δ ppm 7.99 (d, J = 7.81 Hz, 2 H) 8.11 (br. s., 1 H) 8.23 (br. s., 1 H) 8.29-8.45 (m, 5 H) 9.07 (br. s., 2 H) 9.66 (br. s., 1 H); LCMS (M/Z): M + H$^+$ 428. | 428 | |
| 117 | 4-anilino-N-[3-(2-pyridyl)-1,2,4-thiadiazol-5-yl]benzamide<br>$^1$H NMR (400 MHz, DMSO-d$_6$) δ ppm 7.03 (t, J = 7.32 Hz, 1 H) 7.12 (d, J = 8.88 Hz, 2 H) 7.22 (d, J = 7.52 Hz, 2 H) 7.31-7.39 (m, 2 H) 7.51 (ddd, J = 7.50, 4.77, 1.05 Hz, 1 H) 7.98 (td, J = 7.74, 1.76 Hz, 1 H) 8.10 (d, J = 8.83 Hz, 2 H) 8.24 (d, J = 7.86 Hz, 1 H) 8.68-8.75 (m, 1 H) 8.91 (s, 1 H) 13.42 (s, 1 H); LCMS (M/Z): M + H$^+$ 374. | 374 | |
| 118 | 4-(benzylamino)-N-[3-(2-pyridyl)-1,2,4-thiadiazol-5-yl]benzamide<br>$^1$H NMR (400 MHz, DMSO-d$_6$) δ ppm 4.39 (d, J = 5.95 Hz, 2 H) 6.68 (d, J = 8.83 Hz, 2 H) 7.17-7.41 (m, 7 H) 7.50 (dd, J = 6.83, 4.98 Hz, 1 H) 7.90-8.03 (m, 3 H) 8.23 (d, J = 7.86 Hz, 1 H) 8.70 (d, J = 4.10 Hz, 1 H); LCMS (M/Z): M + H$^+$ 388. | 388 | |
| 119 | 3-anilino-N-[3-(2-pyridyl)-1,2,4-thiadiazol-5-yl]benzamide<br>$^1$H NMR (400 MHz, DMSO-d$_6$) δ ppm 6.91 (t, J = 7.30 Hz, 1 H) 7.16 (d, J = 7.61 Hz, 2 H) 7.24-7.33 (m, 3 H) 7.41 (t, J = 7.86 Hz, 1 H) 7.50 (dd, J = 7.03, 5.03 Hz, 1 H) 7.65 (d, J = 7.66 Hz, 1 H) 7.87 (s, 1 H) 7.97 (td, J = 7.70, 1.54 Hz, 1 H) 8.24 (d, J = 7.86 Hz, 1 H) 8.44 (s, 1 H) 8.71 (d, J = 4.34 Hz, 1 H); LCMS (M/Z): M + H$^+$ 374. | 374 | |
| 120 | N-[3-[5-(3-pyridylamino)-2-pyridyl]-1,2,4-thiadiazol-5-yl]-4-(trifluoromethyl)benzamide<br>$^1$H NMR (400 MHz, DMSO-d$_6$) δ ppm 7.32 (dd, J = 8.27, 4.51 Hz, 1 H) 7.55-7.66 (m, 2 H) 7.82 (d, | 443 | |

TABLE 2-continued

| Cpd. | Name | Mass found | LCMS retention time |
|---|---|---|---|
| | J = 8.25 Hz, 2 H) 8.08-8.17 (m, 2 H) 8.36 (d, J = 8.00 Hz, 2 H) 8.44 (dd, J = 4.71, 2.81 Hz, 2 H) 8.78 (s, 1 H) 11.94 (br. s., 1 H); LCMS (M/Z): M + H⁺443. | | |
| 121 | N-[3-(5-morpholino-2-pyridyl)-1,2,4-thiadiazol-5-yl]-4-(trifluoromethyl)benzamide<br>¹H NMR (400 MHz, DMSO-d₆) δ ppm 3.28 (br. s., 4 H) 3.70-3.82 (m, 4 H) 7.44 (dd, J = 8.86, 2.95 Hz, 1 H) 7.94 (d, J = 8.35 Hz, 2 H) 8.09 (d, J = 8.79 Hz, 1 H) 8.37 (d, J = 8.15 Hz, 2 H) 8.41 (d, J = 2.83 Hz, 1 H); LCMS (M/Z): M + H⁺ 436. | 436 | |
| 122 | N-[3-[5-[2-methoxyethyl(methyl)amino]-2-pyridyl]-1,2,4-thiadiazol-5-yl]-4-(trifluoromethyl)benzamide<br>¹H NMR (400 MHz, DMSO-d₆) δ ppm 3.03 (s, 3 H) 3.26 (s, 3 H) 3.49-3.57 (m, 2 H) 3.61 (d, J = 5.22 Hz, 2 H) 7.19 (dd, J = 8.96, 3.05 Hz, 1 H) 7.97 (d, J = 8.35 Hz, 2 H) 8.04 (d, J = 8.88 Hz, 1 H) 8.20 (d, J = 2.93 Hz, 1 H) 8.37 (d, J = 8.15 Hz, 2 H); LCMS (M/Z): M + H⁺ 438. | 438 | |
| 123 | N-[3-(5-pyrrolidin-1-yl-2-pyridyl)-1,2,4-thiadiazol-5-yl]-4-(trifluoromethyl)benzamide<br>¹H NMR (400 MHz, DMSO-d₆) δ ppm 1.92-2.05 (m, 4 H) 3.35-3.39 (m, 4 H) 7.00 (dd, J = 8.79, 2.93 Hz, 1 H) 7.93 (d, J = 8.30 Hz, 2 H) 8.02 (d, J = 2.68 Hz, 1 H) 8.06 (s, 1 H) 8.37 (d, J = 8.10 Hz, 2 H); LCMS (M/Z): M + H⁺ 420. | 420 | |
| 124 | N-[3-[5-(2-pyridylamino)-2-pyridyl]-1,2,4-thiadiazol-5-yl]-4-(trifluoromethyl)benzamide<br>¹H NMR (400 MHz, DMSO-d₆) δ ppm 6.86 (dd, J = 6.74, 5.32 Hz, 1 H) 6.94 (s, 1 H) 7.58-7.70 (m, 1 H) 7.92 (d, J = 8.35 Hz, 2 H) 8.16 (d, J = 8.74 Hz, 1 H) 8.25 (dd, J = 5.00, 1.49 Hz, 1 H) 8.38 (d, J = 8.15 Hz, 2 H) 8.47 (dd, J = 8.74, 2.64 Hz, 1 H) 8.86 (d, J = 2.54 Hz, 1 H) 9.54 (s, 1 H); LCMS (M/Z): M + H⁺ 443. | 443 | |
| 125 | N-[3-[5-(4-methylpiperazin-1-yl)-2-pyridyl]-1,2,4-thiadiazol-5-yl]-4-(trifluoromethyl)benzamide<br>¹H NMR (400 MHz, DMSO-d₆) δ ppm 2.34 (s, 3 H) 2.57-2.68 (m, 4 H) 3.33-3.41 (m, 4 H) 7.44 (dd, J = 8.79, 2.93 Hz, 1 H) 7.95 (d, J = 8.20 Hz, 2 H) 8.08 (d, J = 8.79 Hz, 1 H) 8.37 (d, J = 8.20 Hz, 2 H) 8.41 (d J = 2.93 Hz, 1 H); LCMS (M/Z): M + H⁺ 449. | 449 | |
| 126 | tert-butyl 4-[6-[5-[[4-(trifluoromethyl)benzoyl]amino]-1,2,4-thiadiazol-3-yl]-3-pyridyl]piperazine-1-carboxylate<br>¹H NMR (400 MHz, DMSO-d₆) δ ppm 1.43 (s, 9 H) 3.42-3.58 (m, 4 H) 7.45 (dd, J = 8.88, 2.93 Hz, 1 H) 7.98 (d, J = 8.35 Hz, 2 H) 8.09 (d, J = 8.79 Hz, 1 H) 8.37 (d, J = 8.20 Hz, 2 H) 8.42 (d, J = 2.88 Hz, 1 H) 13.94 (br. s., 1 H); LCMS (M/Z): M + H⁺ 535. | 535 | |
| 127 | N-[3-[5-(1-piperidyl)-2-pyridyl]-1,2,4-thiadiazol-5-yl]-4-(trifluoromethyl)benzamide<br>¹H NMR (400 MHz, DMSO-d₆) δ ppm 1.61 (br. s., 6 H) 3.22-3.40 (m, 4 H) 7.26 (br. s., 1 H) 7.41 (dd, J = 8.91, 2.95 Hz, 1 H) 7.97 (s, 2 H) 8.07 (s, 1 H) 8.27-8.45 (m, 3 H) 13.90 (br. s., 1 H); LCMS (M/Z): M + H⁺ 434. | 434 | |
| 128 | N-[3-(5-anilino-2-pyridyl)-1,2,4-thiadiazol-5-yl]-4-(trifluoromethyl)benzamide<br>¹H NMR (400 MHz, DMSO-d₆) δ ppm 6.98 (t, J = 7.32 Hz, 1 H) 7.21 (d, J = 7.57 Hz, 2 H) 7.30-7.37 (m, 2 H) 7.58 (dd, J = 8.69, 2.78 Hz, 1 H) 7.98 (d, J = 8.35 Hz, 2 H) 8.10 (d, J = 8.69 Hz, 1 H) 8.38 (d, J = 8.15 Hz, 2 H) 8.43 (d, J = 2.73 Hz, 1 H) 8.76 (s, 1 H) 13.91 (br. s., 1 H); LCMS (M/Z): M + H⁺ 442. | 442 | |

TABLE 2-continued

| Cpd. | Name | Mass found | LCMS retention time |
|---|---|---|---|
| 129 | N-[3-[5-(4-hydroxy-1-piperidyl)-2-pyridyl]-1,2,4-thiadiazol-5-yl]-4-(trifluoromethyl)benzamide<br>$^1$H NMR (400 MHz, DMSO-$d_6$) δ ppm 1.47 (dtd, J = 12.86, 9.34, 9.34, 3.86 Hz, 2 H) 1.78-1.89 (m, 2 H) 3.05 (ddd, J = 12.81, 9.96, 2.95 Hz, 2 H) 3.64-3.78 (m, 3 H) 4.74 (d, J = 3.37 Hz, 1 H) 7.42 (dd, J = 8.93, 2.98 Hz, 1 H) 7.96 (d, J = 8.35 Hz, 2 H) 8.05 (d, J = 8.83 Hz, 1 H) 8.29-8.44 (m, 3 H); LCMS (M/Z): M + H$^+$ 450. | 450 | |
| 130 | N-[3-[6-(4-methylpiperazin-1-yl)-2-pyridyl]-1,2,4-thiadiazol-5-yl]-4-(trifluoromethyl)benzamide<br>$^1$H NMR (400 MHz, DMSO-$d_6$) δ ppm 1.91 (s, 4 H) 2.32 (s, 3 H) 2.54 (br. s., 4 H) 3.62 (br. s., 4 H) 6.92 (d, J = 8.44 Hz, 1 H) 7.53 (d, J = 7.32 Hz, 1 H) 7.62-7.73 (m, 1 H) 7.90 (d, J = 8.25 Hz, 2 H) 8.37 (d, J = 8.15 Hz, 2 H); LCMS (M/Z): M + H$^+$ 449. | 449 | |
| 131 | tert-butyl 4-[6-[5-[[4-(trifluoromethyl)benzoyl]amino]-1,2,4-thiadiazol-3-yl]-2-pyridyl]piperazine-1-carboxylate<br>$^1$H NMR (400 MHz, DMSO-$d_6$) δ ppm 1.44 (s, 9 H) 3.46 (d, J = 5.12 Hz, 4 H) 3.60 (br. s., 4 H) 6.96 (d, J = 8.44 Hz, 1 H) 7.54 (d, J = 7.27 Hz, 1 H) 7.67-7.79 (m, 1 H) 7.96 (d, J = 8.35 Hz, 2 H) 8.37 (d, J = 8.15 Hz, 2 H); LCMS (M/Z): M + H$^+$ 535. | 535 | |
| 132 | N-[3-(4-Methyl-2-pyridyl)-1,2,4-thiadiazol-5-yl]-4-(trifluoromethyl)benzamide<br>$^1$H NMR (400 MHz, DMSO-$d_6$) δ ppm 2.43 (s, 3 H) 7.34 (d, J = 4.69 Hz, 1 H) 7.97 (d, J = 7.81 Hz, 2 H) 8.10 (s, 1 H) 8.38 (d, J = 8.20 Hz, 2 H) 8.57 (d, J = 4.88 Hz, 1 H) M + H]$^+$ 365. | 365 | |
| 133 | N-[3-(6-Methyl-2-pyridyl)-1,2,4-thiadiazol-5-yl]-4-(trifluoromethyl)benzamide<br>$^1$H NMR (400 MHz, DMSO-$d_6$) δ ppm 2.56 (s, 3 H) 7.39 (d, J = 7.81 Hz, 1 H) 7.87 (t, J = 7.71 Hz, 1 H) 8.00 (d, J = 8.20 Hz, 2 H) 8.07 (d, J = 7.42 Hz, 2 H) 8.39 (d, J = 8.20 Hz, 2 H) M + H]$^+$ 365. | 365 | |
| 134 | N-[3-[4-(dimethylaminomethyl)-2-pyridyl]-1,2,4-thiadiazol-5-yl]-4-(trifluoromethyl)benzamide<br>$^1$H NMR (400 MHz, DMSO-$d_6$) δ ppm 1.91 (s, 2H) 2.24 (s, 7H) 3.56 (s, 2H) 7.37 (d, J = 4.10 Hz, 1H) 7.89 (d, J = 8.40 Hz, 2H) 8.24 (s, 1H) 8.37 (d, J = 8.20 Hz, 2H) 8.61 (d, J = 4.88 Hz, 1H) M + H]$^+$ 408. | 408 | |
| 135 | N-[3-[4-[methyl-[2-(1-piperidyl)ethyl]amino]-2-pyridyl]-1,2,4-thiadiazol-5-yl]-4-(trifluoromethyl)benzamide<br>$^1$H NMR (400 MHz, DMSO-$d_6$) δ ppm 1.37 (d, J = 4.69 Hz, 2H) 1.47 (d, J = 4.88 Hz, 4H) 2.44 (br s, 4H) 2.52-2.56 (m, 2H) 3.16 (s, 3H) 3.68 (t, J = 6.44 Hz, 2H) 6.86 (dd, J = 6.64, 2.34 Hz, 1H) 7.58 (d, J = 2.54 Hz, 1H) 7.81 (d, J = 8.20 Hz, 2H) 8.13 (d, J = 6.64 Hz, 1H) 8.36 (d, J = 8.00 Hz, 2H) M + H]$^+$ 491. | 491 | |
| 136 | N-[3-[4-[methyl(2-morpholinoethyl)amino]-2-pyridyl]-1,2,4-thiadiazol-5-yl]-4-(trifluoromethyl)benzamide<br>$^1$H NMR (400 MHz, DMSO-$d_6$) δ ppm 1.81 (s, 2H) 2.45 (br s, 5H) 2.52-2.55 (m, 2H) 3.12 (s, 3H) 3.30-3.37 (m, 4H) 3.53-3.59 (m, 4H) 3.65 (t, J = 6.54 Hz, 2H) 6.78 (dd, J = 6.25, 2.54 Hz, 1H) 7.57 (d, J = 2.54 Hz, 1H) 7.80 (d, J = 8.20 Hz, 2H) 8.15 (d, J = 6.44 Hz, 1H) 8.36 (d, J = 8.00 Hz, 2H) M + H]$^+$ 493 | 493 | |
| 137 | N-[3-(4-pyrrolidin-1-yl-2-pyridyl)-1,2,4-thiadiazol-5-yl]-4-(trifluoromethyl)benzamide<br>$^1$H NMR (400 MHz, DMSO-$d_6$) δ ppm 2.03 (t, J = 6.35 Hz, 4H) 3.51 (br s, 4H) 6.72 (d, J = 4.30 Hz, 1H) 7.44 (d, J = 2.34 Hz, 1 H) 7.81 (d, J = 8.20 Hz, 2H) 8.13 (d, J = 6.64 Hz, 1H) 8.36 (d, J = 8.20 Hz, 2H) M + H]$^+$ 420 | 420 | |

TABLE 2-continued

| Cpd. | Name | Mass found | LCMS retention time |
|---|---|---|---|
| 138 | N-[3-[4-(4-methylpiperazin-1-yl)-2-pyridyl]-1,2,4-thiadiazol-5-yl]-4-(trifluoromethyl)benzamide<br>$^1$H NMR (400 MHz, DMSO-d$_6$) δ ppm 2.70-2.96 (m, 6H) 3.04-3.28 (m, 3H) 3.55-3.80 (m, 4H) 4.43 (br s, 1H) 7.37 (dd, J = 6.93, 2.05 Hz, 1H) 7.82 (d, J = 2.34 Hz, 1H) 8.02 (d, J = 8.20 Hz, 2H) 8.33-8.45 (m, 3H) M + H]$^+$ 449. | 449 | |
| 139 | N-[3-[4-[2-hydroxyethyl(methyl)amino]-2-pyridyl]-1,2,4-thiadiazol-5-yl]-4-(trifluoromethyl)benzamide<br>$^1$H NMR (400 MHz, DMSO-d$_6$) δ ppm 3.27 (s, 3H) 3.65-3.82 (m, 4H) 7.84 (d, J = 8.00 Hz, 1H) 8.01 (d, J = 8.20 Hz, 2H) 8.06 (d, J = 8.00 Hz, 1H) 8.21 (d, J = 7.22 Hz, 1H) 8.39 (d, J = 8.20 Hz, 2H) M + H]$^+$ 424. | 424 | |
| 140 | N-[3-[4-[2-(1-piperidyl)ethoxy]-2-pyridyl]-1,2,4-thiadiazol-5-yl]-4-(trifluoromethyl)benzamide<br>$^1$H NMR (400 MHz, DMSO-d$_6$) δ ppm 1.91 (s, 2H) 2.76 (t, J = 5.56 Hz, 2H) 3.52-3.70 (m, 4H) 4.27 (t, J = 5.66 Hz, 2H) 7.02 (d, J = 2.93 Hz, 1H) 7.78 (d, J = 2.34 Hz, 1H) 7.85 (d, J = 8.20 Hz, 2H) 8.36 (d, J = 8.01 Hz, 2H) 8.46 (d, J = 5.66 Hz, 1H) M + H]$^+$ 480. | 480 | |
| 141 | N-[3-[4-(2-methoxyethoxy)-2-pyridyl]-1,2,4-thiadiazol-5-yl]-4-(trifluoromethyl)benzamide<br>$^1$H NMR (400 MHz, DMSO-d$_6$) δ ppm 3.33 (s, 3H) 3.65-3.80 (m, 2H) 4.34-4.48 (m, 3H) 7.37 (d, J = 3.90 Hz, 1H) 7.88 (d, J = 1.76 Hz, 1H) 8.01 (d, J = 8.20 Hz, 2H) 8.39 (d, J = 8.20 Hz, 2H) 8.64 (d, J = 6.25 Hz, 1H) M + H]$^+$ 425. | 425 | |
| 142 | N-[3-[4-(2-dimethylaminoethyloxy)-2-pyridyl]-1,2,4-thiadiazol-5-yl]-4-(trifluoromethyl)benzamide<br>$^1$H NMR (400 MHz, DMSO-d$_6$) δ ppm 2.84 (d, J = 3.90 Hz, 6H) 3.59 (br s, 2H) 4.66 (br s, 2H) 7.83 (d, J = 8.20 Hz, 2H) 8.00 (d, J = 8.00 Hz, 2H) 8.07 (d, J = 8.00 Hz, 2H) 8.40 (d, J = 8.01 Hz, 2H) M + H]$^+$ 438. | 438 | |
| 143 | N-[3-[4-(2,2-dimethylpropoxy)-2-pyridyl]-1,2,4-thiadiazol-5-yl]-4-(trifluoromethyl)benzamide<br>$^1$H NMR (400 MHz, DMSO-d$_6$) δ ppm 1.04 (s, 9H) 3.94 (s, 2H) 7.36 (br s, 1H) 7.90 (br s, 1H) 8.04 (d, J = 8.00 Hz, 2H) 8.39 (d, J = 8.01 Hz, 2H) 8.61 (br s, 1H) M + H]$^+$ 437. | 437 | |
| 144 | N-[3-[4-[(1-methyl-4-piperidyl)oxy]-2-pyridyl]-1,2,4-thiadiazol-5-yl]-4-(trifluoromethyl)benzamide<br>$^1$H NMR (400 MHz, DMSO-d$_6$) δ ppm 1.88-2.13 (m, 2H) 2.15-2.32 (m, 2H) 2.71 (d, J = 12.10 Hz, 3H) 3.13 (br s, 2H) 3.27 (br s, 2H) 4.78-4.94 (m, 1H) 5.04 (br s, 1H) 7.18-7.31 (m, 1H) 7.74-7.87 (m, 1H) 7.97 (d, J = 5.66 Hz, 2H) 8.36 (d, J = 5.66 Hz, 2H) 8.57 (br s, 1H) M + H]$^+$ 464. | 464 | |
| 145 | N-[3-(4-tetrahydropyran-4-yloxy-2-pyridyl)-1,2,4-thiadiazol-5-yl]-4-(trifluoromethyl)benzamide<br>$^1$H NMR (400 MHz, DMSO-d$_6$) δ ppm 1.64-1.76 (m, 2H) 2.01-2.09 (m, 2H) 3.46-3.61 (m, 2H) 3.83-3.93 (m, 2H) 4.98 (dt, J = 8.15, 4.22 Hz, 1H) 7.38 (d, J = 4.69 Hz, 1H) 7.85 (d, J = 2.34 Hz, 1H) 8.01 (d, J = 8.20 Hz, 2H) 8.39 (d, J = 8.00 Hz, 2H) 8.61 (d, J = 6.05 Hz, 1H) M + H]$^+$ 451. | 451 | |
| 146 | N-[3-[4-(oxetan-3-yloxy)-2-pyridyl]-1,2,4-thiadiazol-5-yl]-4-(trifluoromethyl)benzamide<br>$^1$H NMR (400 MHz, DMSO-d$_6$) δ ppm 3.61-3.82 (m, 2H) 3.84-3.97 (m, 1H) 3.97-4.09 (m, 1H) 4.91-5.10 (m, 1H) 7.43 (d, J = 3.71 Hz, 1H) 7.94 (s, 1H) 8.01 (d, J = 8.20 Hz, 2H) 8.39 (d, J = 8.20 hz, 2H) 8.64 (d, J = 6.25 Hz, 1H) M + H]$^+$ 423. | 423 | |
| 147 | N-[3-[4-(hydroxymethyl)-2-pyridyl]-1,2,4-thiadiazol-5-yl]-4-(trifluoromethyl)benzamide<br>$^1$H NMR (400 MHz, DMSO-d$_6$) δ ppm 4.62 (br s, 2H) 5.49 (br s, 1H) 7.31 (d, J = 4.49 Hz, 1H) 7.78 (d, J = 8.20 Hz, 2H) 8.22 (s, 1H) 8.36 (d, J = 8.01 Hz, 2H) 8.56 (d, J = 4.88 Hz, 1H) M + H]$^+$ 381. | 381 | |

3-Pyridin-2-yl-[1,2,4]thiadiazol-5-ylamine was obtained from commercial sources.

Parasiticidal Activity

The compounds of formula (I) were tested for activity against *Dirofilaria immitis*.

*Dirofilaria immitis* Microfilariae Motility Assay

*Dirofilaria immitis* microfilariae are isolated by filtration from blood of an infected beagle dog allowed to incubate at 37C/5% $CO_2$/95% RH in RPMI media. For assay 500 microfilariae are added into 96-well plates followed by addition of compounds diluted in DMSO for single-point or dose response (5-point) analysis. Ivermectin or emodepside are included as a positive control and DMSO-only wells are included as negative controls. Plates containing parasites and compounds are incubated at 37° C./5% $CO_2$/95% RH for 72 hours and motility is assessed using an LCD camera imaging system. Percent motility inhibition values are generated relative to the average of the DMSO-only wells. For dose response analysis, data points were averaged and curve fitting software is used to generate sigmoidal curves for the determination of $EC_{50}$ values (i.e. the effective concentration to kill 50% of the organism).

*Dirofilaria immitis* L4 Stage Assay

L3 larvae of *D. immitis* are isolated from infected mosquitoes and allowed to moult into L4 stages in culture. Approximately 5-10 *D. immitis* L4 stage parasites are added to 96-well plates containing RPMI media and incubated at 37C/5% $CO_2$/95% RH. The compounds of the invention are diluted in dimethyl sulfoxide (DMSO) and added at a single dose to identify those that affect parasite motility upon microscopic inspection or automated imaging after 72 hours of incubation. Compounds with activity at that concentration are progressed to a five-point dose titration assay and evaluated by microscopic examination or automated imaging of the wells after incubation for 72 hours, Efficacy is based on reduction in motility of the treated L4 larvae as compared to the positive (invermectin or emodepside) and negative (DMSO) controls. Compounds are evaluated in duplicate and efficacy is reported as the lowest dose that gives 100% inhibition of parasite motility (MIC100) is reported for microscopy assays. For automated imaging assays, percent motility inhibition values are generated relative to the average of the DMSO-only wells and $EC_{90}$ or $EC_{50}$ values are generated using curve fitting software.

L929 Mouse Fibroblast Cytotoxicity Assay

For evaluation of mammalian cell cytotoxicity, L929 fibroblasts are seeded at 2,000 cells/well and exposed to 2-fold dilutions of test compounds directly parallel to the assay for parasitic activity. Plates with parasites or L929 cells are incubated with compounds wider appropriate conditions for each cell type. Tamoxifen and taxol are included as a positive control and DMSO-only wells are included as negative controls, After 72 hours of incubation, resazurin (20 μL of 12.5 mg/mL stock in phosphate buffered saline) was added each well and plates are incubated for an additional 4-6 h. To assess cell viability, fluorescence is read in the EnVisiong® plate reader (Perkin Elmer, Waltham, Mass.) at an excitation wavelength of 530 nm and emission of 590 nm. Data points are averaged and curve-fitting software is used to generate sigmoidal dose-response curves for the determination of $IC_{50}$ values.

Generally, at concentrations of 100 μM or less, the compounds of the invention demonstrated activity against *D. immitis* microfilariae or *D. immitis* L4 stage. The following compounds were determined to have $EC_{50}$ values less than 5 μM: Compounds 1-47,49-65,67, 70 72, 74-77, 79,89, 91-94, 96-106, 11-14, 116, 118, 119, 121-129, 131-141, 143, 145-147.

All publications, patents and patent applications cited in this specification are incorporated herein by reference in their entireties as if each individual publication, patent or patent application were specifically and individually indicated to he incorporated by reference. While the foregoing has been described in terms of various embodiments, the skilled artisan will appreciate that various modifications, substitutions, omissions, and changes may be made without departing from the spirit thereof.

The invention claimed is:

1. A compound of formula (I)

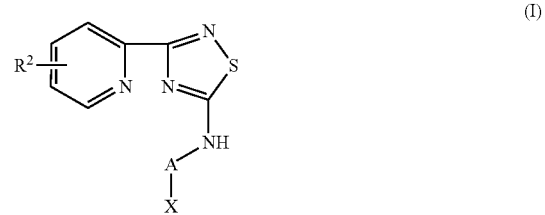

wherein:

A is C=O or $SO_2$;

X is $R^1$ or $NHR^1$;

$R^1$ is:

phenyl optionally substituted by from one to three substituents, which are the same or different, each selected from the group consisting of nitro, —$NR^3R^4$, cyano, —$NR^3COR^5$, alkyl, —$SO_2R^5$, —$NR^3SO_2R^5$, —$SO_2NR^3R^4$, —$CONR^3R^4$, —$CONHC_6H_5$, hydroxy, alkoxy, aryloxy, aryl, heterocyclyl, haloalkyl, haloalkoxy, mercapto, thioalkyl and halogen;

naphthyl optionally substituted by from one to three substituents, which are the same or different, each independently selected from the group consisting of nitro, —$NR^3R^4$, cyano, —$NR^3COR^5$, alkyl, —$SO_2R^5$, —$NR^3SO_2R^5$, —$SO_2NR^3R^4$, —$CONR^3R^4$, —$CONHC_6H_5$, hydroxy, alkoxy, aryloxy, aryl, heterocyclyl, haloalkyl, haloalkoxy, mercapto, thioalkyl and halogen;

quinoxolinyl optionally substituted by from one to three substituents, which are the same or different, each independently selected from the group consisting of nitro, —$NR^3R^4$, cyano, —$NR^3COR^5$, alkyl, —$SO_2R^5$, —$NR^3SO_2R^5$, —$SO_2NR^3R^4$, —$CONR^3R^4$, —$CONHC_6H_5$, hydroxy, alkoxy, aryloxy, aryl, heterocyclyl, haloalkyl, haloalkoxy, mercapto, thioalkyl and halogen;

quinolinyl optionally substituted by from one to three substituents, which are the same or different, each independently selected from the group consisting nitro, —$NR^3R^4$, cyano, —$NR^3COR^5$, alkyl, —$SO_2R^5$, —$NR^3SO_2R^5$, —$SO_2NR^3R^4$, —$CONR^3R^4$, —$CONHC_6H_5$, hydroxy, alkoxy, aryloxy, aryl, heterocyclyl, haloalkyl, haloalkoxy, mercapto, thioalkyl and halogen;

or thionyl or furyl optionally substituted by from one to three substituents which are the same or different, each selected from the group consisting of nitro, —$NR^3R^4$, cyano, —$NR^3COR^5$, alkyl, —$SO_2R^5$, —$NR^3SO_2R^5$, —$SO_2NR^3R^4$, —$CONR^3R^4$, —$CONHC_6H_5$, hydroxy, alkoxy, aryloxy, aryl, heterocyclyl, haloalkyl, haloalkoxy, mercapto (—SH), thioalkyl and halogen;

$R^2$ is hydrogen, halogen, alkyl, alkoxy, haloalkyl or haloalkoxy, aminoalkyl, alkylaminoalkyl, aryl, heterocyclyl or —CONR$^3$R$^4$; or R$^2$, together with two adjacent carbons of the pyridyl ring to which it is attached, forms a saturated or unsaturated ring containing from 4 to 6 ring atoms;

$R^3$ and $R^4$, which are the same or different, each independently represent hydrogen or alkyl; or when $R^3$ and $R^4$ are each attached to a nitrogen atom, they may form a saturated or unsaturated heterocyclic ring containing from 4 to 6 ring atoms $R^5$ is alkyl or haloalkyl;

or a pesticidally acceptable salt thereof.

2. The compound of claim 1, where $R^2$ is hydrogen or halogen.

3. The compound of claim 1, where $R^1$ is phenyl substituted by from one to three substituents which are the same or different, each selected from the group consisting of halogen, cyano, haloalkyl, alkoxy and haloalkoxy; or $R^1$ is naphthyl optionally substituted by from one to three substituents which are the same or different, each selected from the group consisting of halogen, cyano, haloalkyl, alkoxy and haloalkoxy.

4. The compound of claim 1, where:
A is C═O;
X is NHR$^1$;
$R^1$ is phenyl optionally substituted by from one to three substituents which are the same or different, each selected from the group consisting of trifluoromethyl, trifluoromethoxy, halogen, cyano, methyl, ethyl, methoxy, ethoxy, thiomethyl, —SO$_2$CH$_3$, —SO$_2$NH$_2$, —SO$_2$NHCH$_3$, —SO$_2$N(CH$_3$)$_2$ and —NHSO$_2$CH$_3$;
and $R^2$ is hydrogen, fluoro, methyl, trifluoromethyl, methoxy or trifluoromethoxy.

5. The compound of claim 1, where:
A is C═O;
X is R$^1$;
$R^1$ is phenyl substituted by from one to three substituents which are the same or different selected from the group consisting of trifluoromethyl, trifluoromethoxy, chloro, fluoro, cyano, methyl, ethyl, methoxy, ethoxy, aryloxy, thiomethyl, —SO$_2$CH$_3$, —SO$_2$NH$_2$, —SO$_2$NHCH$_3$, —SO$_2$N(CH$_3$)$_2$ and —NHSO$_2$CH$_3$; and
$R^2$ is hydrogen, fluoro, methyl, trifluoromethyl, methoxy, trifluoromethoxy, morpholino, aminoalkyl or dimethylaminomethyl.

6. The compound of claim 1, where:
A is SO$_2$;
X is R$^1$;
$R^1$ is phenyl substituted by from one to three substituents which are the same or different selected from the group consisting of trifluoromethyl, trifluoromethoxy, chloro, fluoro, cyano, methyl, ethyl, methoxy, ethoxy, thiomethyl, methanesulfonyl, sulfonamide, methylsulfonamide, dimethylsulfonamide, and methylsulfonanilide; and
$R^2$ is hydrogen.

7. The compound of claim 1, where:
A is C═O or SO$_2$;
X is R$^1$ or NHR$^1$;
$R^1$ is:
phenyl optionally substituted by from one to three substituents which are the same or different, each selected from the group consisting of nitro, —NR$^3$R$^4$, cyano, —NR$^3$COR$^5$, alkyl, alkoxy, aryl, heterocyclyl, aryloxy, haloalkyl, haloalkoxy, mercapto (—SH), thioalkyl and halogen;

$R^2$ is hydrogen, fluoro, methyl, trifluoromethyl, methoxy, trifluoromethoxy, morpholino, aminoalkyl or dimethylaminomethyl.

8. A compound selected from:
1-(4-methoxyphenyl)-3-[3-(2-pyridyl)-1,2,4-thiadiazol-5-yl]urea;
1-(2-chlorophenyl)-3-[3-(2-pyridyl)-1,2,4-thiadiazol-5-yl]urea;
1-[3-(2-pyridyl)-1,2,4-thiadiazol-5-yl]-3-[4-(trifluoromethyl)phenyl]urea;
1-(3-methoxyphenyl)-3-[3-(2-pyridyl)-1,2,4-thiadiazol-5-yl]urea;
1-[3-(2-pyridyl)-1,2,4-thiadiazol-5-yl]-3-[4-(trifluoromethoxy)phenyl]urea;
1-[3-(2-pyridyl)-1,2,4-thiadiazol-5-yl]-3-[3-(trifluoromethyl)phenyl]urea;
4-chloro-N-[3-(2-pyridyl)-1,2,4-thiadiazol-5-yl]benzamide;
3-chloro-N-[3-(2-pyridyl)-1,2,4-thiadiazol-5-yl]benzamide;
4-cyano-N-[3-(2-pyridyl)-1,2,4-thiadiazol-5-yl]benzamide;
3-fluoro-N-[3-(2-pyridyl)-1,2,4-thiadiazol-5-yl]benzamide;
N-[3-(2-pyridyl)-1,2,4-thiadiazol-5-yl]-4-(trifluoromethyl)benzamide;
N-[3-(2-pyridyl)-1,2,4-thiadiazol-5-yl]naphthalene-2-carboxamide;
4-trifluoromethoxy-N-[3-(2-pyridyl)-1,2,4-thiadiazol-5-yl]benzamide;
4-chloro-N-[3-(2-pyridyl)-1,2,4-thiadiazol-5-yl]benzenesulfonamide;
2-chloro-N-[3-(2-pyridyl)-1,2,4-thiadiazol-5-yl]benzenesulfonamide;
4-cyano-N-[3-(2-pyridyl)-1,2,4-thiadiazol-5-yl]benzenesulfonamide;
4-methoxy-N-[3-(2-pyridyl)-1,2,4-thiadiazol-5-yl]benzenesulfonamide;
2-methoxy-N-[3-(2-pyridyl)-1,2,4-thiadiazol-5-yl]benzenesulfonamide;
N-[3-(2-pyridyl)-1,2,4-thiadiazol-5-yl]-3-(trifluoromethyl)benzenesulfonamide;
N-[3-(2-pyridyl)-1,2,4-thiadiazol-5-yl]-4-(trifluoromethyl)benzenesulfonamide;
N-[3-(3-fluoro-2-pyridyl)-1,2,4-thiadiazol-5-yl]-4-(trifluoromethyl)benzamide;
N-[3-(4-morpholino-2-pyridyl)-1,2,4-thiadiazol-5-yl]-4-(trifluoromethyl)benzamide;
N-[3-[4-[benzyl(methyl)amino]-2-pyridyl]-1,2,4-thiadiazol-5-yl]-4-(trifluoromethyl)benzamide;
N-[3-[4-(dimethylamino)-2-pyridyl]-1,2,4-thiadiazol-5-yl]-4-(trifluoromethyl)benzamide;
N-[3-[4-[2-methoxyethyl(methyl)amino]-2-pyridyl]-1,2,4-thiadiazol-5-yl]-4-(trifluoromethyl)benzamide;
N-[3-(5-methoxy-2-pyridyl)-1,2,4-thiadiazol-5-yl]-4-(trifluoromethyl)benzamide;
N-[3-(4-methoxy-2-pyridyl)-1,2,4-thiadiazol-5-yl]-4-(trifluoromethyl)benzamide;
N-[3-[4-(triazolo[4,5-b]pyridin-3-yloxy)-2-pyridyl]-1,2,4-thiadiazol-5-yl]-4-(trifluoromethyl)benzamide;
N-[3-(5-bromo-2-pyridyl)-1,2,4-thiadiazol-5-yl]-4-(trifluoromethyl)benzamide;
methyl 2-[5-[[4-(trifluoromethyl)benzoyl]amino]-1,2,4-thiadiazol-3-yl]pyridine-4-carboxylate;

N-[3-(2-pyridyl)-1,2,4-thiadiazol-5-yl]isoquinoline-7-carboxamide;
4-acetamido-N-[3-(2-pyridyl)-1,2,4-thiadiazol-5-yl]benzamide;
4-fluoro-N-[3-(2-pyridyl)-1,2,4-thiadiazol-5-yl]benzamide;
4-nitro-N-[3-(2-pyridyl)-1,2,4-thiadiazol-5-yl]benzamide;
N-[3-(2-pyridyl)-1,2,4-thiadiazol-5-yl]quinoxaline-6-carboxamide;
N-[3-(2-pyridyl)-1,2,4-thiadiazol-5-yl]thiophene-2-carboxamide;
N-[3-(2-pyridyl)-1,2,4-thiadiazol-5-yl]thiophene-3-carboxamide;
N-[3-(4-isopropyl-2-pyridyl)-1,2,4-thiadiazol-5-yl]-4-(trifluoromethyl)benzamide;
N-[3-(3-isoquinolyl)-1,2,4-thiadiazol-5-yl]-4-(trifluoromethyl)benzamide;
N-[3-(5-fluoro-2-pyridyl)-1,2,4-thiadiazol-5-yl]-4-(trifluoromethyl)benzamide;
N-[3-(5-methyl-2-pyridyl)-1,2,4-thiadiazol-5-yl]-4-(trifluoromethyl)benzamide;
3-chloro-4-fluoro-N-[3-(5-fluoro-2-pyridyl)-1,2,4-thiadiazol-5-yl]benzamide;
N-[3-(5-fluoro-2-pyridyl)-1,2,4-thiadiazol-5-yl]-4-(trifluoromethoxy)benzamide;
4-tert-butyl-N-[3-(5-fluoro-2-pyridyl)-1,2,4-thiadiazol-5-yl]benzamide;
N-[3-(5-fluoro-2-pyridyl)-1,2,4-thiadiazol-5-yl]-3,5-bis(trifluoromethyl)benzamide;
N-[3-(5-fluoro-2-pyridyl)-1,2,4-thiadiazol-5-yl]-3-(trifluoromethyl)benzamide;
3,4-dichloro-N-[3-(5-fluoro-2-pyridyl)-1,2,4-thiadiazol-5-yl]benzamide;
3-methylsulfonyl-N-[3-(2-pyridyl)-1,2,4-thiadiazol-5-yl]benzamide;
N-[3-(2-pyridyl)-1,2,4-thiadiazol-5-yl]isoquinoline-5-carboxamide;
3-chloro-4-(4-methylpiperazin-1-yl)-N-[3-(2-pyridyl)-1,2,4-thiadiazol-5-yl]benzamide;
methyl 4-[[3-(2-pyridyl)-1,2,4-thiadiazol-5-yl]carbamoyl]benzoate;
4-(diethylsulfamoyl)-N-[3-(2-pyridyl)-1,2,4-thiadiazol-5-yl]benzamide;
4-methyl-N-[3-(2-pyridyl)-1,2,4-thiadiazol-5-yl]thiophene-2-carboxamide;
3-chloro-4-fluoro-N-[3-(2-pyridyl)-1,2,4-thiadiazol-5-yl]benzamide;
2-fluoro-3-methoxy-N-[3-(2-pyridyl)-1,2,4-thiadiazol-5-yl]benzamide;
N-[3-(2-pyridyl)-1,2,4-thiadiazol-5-yl]-3-(trifluoromethyl)benzamide;
2,5-dimethyl-N-[3-(2-pyridyl)-1,2,4-thiadiazol-5-yl]furan-3-carboxamide;
4-tert-butyl-N-[3-(2-pyridyl)-1,2,4-thiadiazol-5-yl]benzamide;
N-[3-(2-pyridyl)-1,2,4-thiadiazol-5-yl]-1,3-benzodioxole-5-carboxamide;
3,4-dichloro-N-[3-(2-pyridyl)-1,2,4-thiadiazol-5-yl]benzamide;
N-[3-(2-pyridyl)-1,2,4-thiadiazol-5-yl]-3,5-bis(trifluoromethyl)benzamide;
4-methoxy-N-[3-(2-pyridyl)-1,2,4-thiadiazol-5-yl]benzamide;
4-phenoxy-N-[3-(2-pyridyl)-1,2,4-thiadiazol-5-yl]benzamide;
4-fluoro-N-[3-(2-pyridyl)-1,2,4-thiadiazol-5-yl]-2-(trifluoromethyl)benzamide;
N-[3-(2-pyridyl)-1,2,4-thiadiazol-5-yl]benzamide;
4-[[3-(2-pyridyl)-1,2,4-thiadiazol-5-yl]carbamoyl]benzoic acid;
4-iodo-N-[3-(2-pyridyl)-1,2,4-thiadiazol-5-yl]benzamide;
4-morpholino-N-[3-(2-pyridyl)-1,2,4-thiadiazol-5-yl]benzamide;
4-(morpholine-4-carbonyl)-N-[3-(2-pyridyl)-1,2,4-thiadiazol-5-yl]benzamide;
tert-butyl 4-[4-[[3-(2-pyridyl)-1,2,4-thiadiazol-5-yl]carbamoyl]benzoyl]piperazine-1-carboxylate;
tert-butyl 4-[[4-[[3-(2-pyridyl)-1,2,4-thiadiazol-5-yl]carbamoyl]benzoyl]amino]piperidine-1-carboxylate;
4-(piperidine-1-carbonyl)-N-[3-(2-pyridyl)-1,2,4-thiadiazol-5-yl]benzamide;
4-(piperazine-1-carbonyl)-N-[3-(2-pyridyl)-1,2,4-thiadiazol-5-yl]benzamide;
N1-[3-(2-pyridyl)-1,2,4-thiadiazol-5-yl]terephthalamide;
4-(2-pyridylamino)-N-[3-(2-pyridyl)-1,2,4-thiadiazol-5-yl]benzamide;
tert-butyl 4-[4-[[3-(2-pyridyl)-1,2,4-thiadiazol-5-yl]carbamoyl]anilino]piperidine-1-carboxylate;
4-phenyl-N-[3-(2-pyridyl)-1,2,4-thiadiazol-5-yl]benzamide;
4-piperazin-1-yl-N-[3-(2-pyridyl)-1,2,4-thiadiazol-5-yl]benzamide;
4-(4-piperidylamino)-N-[3-(2-pyridyl)-1,2,4-thiadiazol-5-yl]benzamide;
tert-butyl 4-[4-[[3-(2-pyridyl)-1,2,4-thiadiazol-5-yl]carbamoyl]phenyl]piperazine-1-carboxylate;
3-chloro-2-fluoro-N-[3-(2-pyridyl)-1,2,4-thiadiazol-5-yl]-5-(trifluoromethyl)benzamide;
N-[3-(2-pyridyl)-1,2,4-thiadiazol-5-yl]-4-(1,1,2,2-tetrafluoroethoxy)benzamide;
2-methoxy-N-[3-(2-pyridyl)-1,2,4-thiadiazol-5-yl]-4-(trifluoromethoxy)benzamide;
N-[3-(2-pyridyl)-1,2,4-thiadiazol-5-yl]-5-(trifluoromethyl)furan-2-carboxamide;
N-[3-(2-pyridyl)-1,2,4-thiadiazol-5-yl]-5-(trifluoromethyl)thiophene-2-carboxamide;
4-formyl-N-[3-(2-pyridyl)-1,2,4-thiadiazol-5-yl]benzamide;
4-[hydroxy(phenyl)methyl]-N-[3-(2-pyridyl)-1,2,4-thiadiazol-5-yl]benzamide;
3-bromo-N-[3-(2-pyridyl)-1,2,4-thiadiazol-5-yl]benzamide;
4-benzyl-N-[3-(2-pyridyl)-1,2,4-thiadiazol-5-yl]benzamide;
N4-[3-(2-pyridyl)-1,2,4-thiadiazol-5-yl]terephthalamide;
4-bromo-N-[3-(2-pyridyl)-1,2,4-thiadiazol-5-yl]benzamide;
3-chloro-N-[3-(2-pyridyl)-1,2,4-thiadiazol-5-yl]-4-(trifluoromethoxy)benzamide;
N-[3-(4-phenyl-2-pyridyl)-1,2,4-thiadiazol-5-yl]-4-(trifluoromethyl)benzamide;
4-(trifluoromethyl)-N-[3-[5-(trifluoromethyl)-2-pyridyl]-1,2,4-thiadiazol-5-yl]benzamide;
N4-phenyl-N-[3-(2-pyridyl)-1,2,4-thiadiazol-5-yl]terephthalamide;
N-[3-(2-pyridyl)-1,2,4-thiadiazol-5-yl]-2-(trifluoromethyl) benzamide;
2-fluoro-N-[3-(2-pyridyl)-1,2,4-thiadiazol-5-yl]-4-(trifluoromethoxy)benzamide;
N-[3-(2-pyridyl)-1,2,4-thiadiazol-5-yl]-2-(trifluoromethoxy)benzamide;

N-[3-(2-pyridyl)-1,2,4-thiadiazol-5-yl]-3-(trifluoromethoxy)benzamide;
4-(4-fluorophenoxy)-N-[3-(2-pyridyl)-1,2,4-thiadiazol-5-yl]benzamide;
3-hydroxy-N-[3-(2-pyridyl)-1,2,4-thiadiazol-5-yl]-5-(trifluoromethyl)thiophene-2-carboxamide;
4-(2,4-difluorophenoxy)-N-[3-(2-pyridyl)-1,2,4-thiadiazol-5-yl]benzamide;
N-[3-(2-pyridyl)-1,2,4-thiadiazol-5-yl]-4-[4-(trifluoromethyl)phenoxy]benzamide;
N-[3-(2-pyridyl)-1,2,4-thiadiazol-5-yl]-3-[4-(trifluoromethyl)phenoxy]benzamide;
3-(4-fluorophenoxy)-N-[3-(2-pyridyl)-1,2,4-thiadiazol-5-yl]benzamide;
3-phenoxy-N-[3-(2-pyridyl)-1,2,4-thiadiazol-5-yl]benzamide;
N1-(4-piperidyl)-N4-[3-(2-pyridyl)-1,2,4-thiadiazol-5-yl]terephthalamide;
N-[3-(5-piperazin-1-yl-2-pyridyl)-1,2,4-thiadiazol-5-yl]-4-(trifluoromethyl)benzamide;
4-(4-piperidyloxy)-N-[3-(2-pyridyl)-1,2,4-thiadiazol-5-yl]pyridine-2-carboxamide;
N-[3-(6-piperazin-1-yl-2-pyridyl)-1,2,4-thiadiazol-5-yl]-4-(trifluoromethyl)benzamide;
4-(3-pyridyl)-N-[3-(2-pyridyl)-1,2,4-thiadiazol-5-yl]benzamide;
N-[3-(5-phenyl-2-pyridyl)-1,2,4-thiadiazol-5-yl]-4-(trifluoromethyl)benzamide;
4-(trifluoromethyl)-N-[3-(5-vinyl-2-pyridyl)-1,2,4-thiadiazol-5-yl]benzamide;
N-[3-[5-(3,6-dihydro-2H-pyran-4-yl)-2-pyridyl]-1,2,4-thiadiazol-5-yl]-4-(trifluoromethyl)benzamide;
N-[3-(6-phenyl-2-pyridyl)-1,2,4-thiadiazol-5-yl]-4-(trifluoromethyl)benzamide;
N-[3-[6-(3-pyridyl)-2-pyridyl]-1,2,4-thiadiazol-5-yl]-4-trifluoromethyl)benzamide;
4-anilino-N-[3-(2-pyridyl)-1,2,4-thiadiazol-5-yl]benzamide;
4-(benzylamino)-N-[3-(2-pyridyl)-1,2,4-thiadiazol-5-yl]benzamide;
3-anilino-N-[3-(2-pyridyl)-1,2,4-thiadiazol-5-yl]benzamide;
N-[3-[5-(3-pyridylamino)-2-pyridyl]-1,2,4-thiadiazol-5-yl]-4-(trifluoromethyl)benzamide;
N-[3-(5-morpholino-2-pyridyl)-1,2,4-thiadiazol-5-yl]-4-(trifluoromethyl)benzamide;
N-[3-[5-[2-methoxyethyl(methyl)amino]-2-pyridyl]-1,2,4-thiadiazol-5-yl]-4-(trifluoromethyl)benzamide;
N-[3-(5-pyrrolidin-1-yl-2-pyridyl)-1,2,4-thiadiazol-5-yl]-4-(trifluoromethyl)benzamide;
N-[3-[5-(2-pyridylamino)-2-pyridyl]-1,2,4-thiadiazol-5-yl]-4-(trifluoromethyl)benzamide;
N-[3-[5-(4-methylpiperazin-1-yl)-2-pyridyl]-1,2,4-thiadiazol-5-yl]-4-(trifluoromethyl)benzamide;
tert-butyl 4-[6-[5-[[4-(trifluoromethyl)benzoyl]amino]-1,2,4-thiadiazol-3-yl]-3-pyridyl]piperazine-1-carboxylate;
N-[3-[5-(1-piperidyl)-2-pyridyl]-1,2,4-thiadiazol-5-yl]-4-(trifluoromethyl)benzamide;
N-[3-(5-anilino-2-pyridyl)-1,2,4-thiadiazol-5-yl]-4-(trifluoromethyl)benzamide;
N-[3-[5-(4-hydroxy-1-piperidyl)-2-pyridyl]-1,2,4-thiadiazol-5-yl]-4-(trifluoromethyl)benzamide;
N-[3-[6-(4-methylpiperazin-1-yl)-2-pyridyl]-1,2,4-thiadiazol-5-yl]-4-(trifluoromethyl)benzamide;
tert-butyl 4-[6-[5-[[4-(trifluoromethyl)benzoyl]amino]-1,2,4-thiadiazol-3-yl]-2-pyridyl]piperazine-1-carboxylate;
N-[3-(4-Methyl-2-pyridyl)-1,2,4-thiadiazol-5-yl]-4-(trifluoromethyl)benzamide;
N-[3-(6-Methyl-2-pyridyl)-1,2,4-thiadiazol-5-yl]-4-(trifluoromethyl)benzamide;
N-[3-[4-(dimethylaminomethyl)-2-pyridyl]-1,2,4-thiadiazol-5-yl]-4-(trifluoromethyl)benzamide;
N-[3-[4-[methyl-[2-(1-piperidyl)ethyl]amino]-2-pyridyl]-1,2,4-thiadiazol-5-yl]-4-(trifluoromethyl)benzamide;
N-[3-[4-[methyl(2-morpholinoethyl)amino]-2-pyridyl]-1,2,4-tiadiazol-5-yl]-4-(trifluoromethyl)benzamide;
N-[3-(4-pyrrolidin-1-yl-2-pyridyl)-1,2,4-thiadiazol-5-yl]-4-(trifluoromethyl)benzamide;
N-[3-[4-(4-methylpiperazin-1-yl)-2-pyridyl]-1,2,4-thiadiazol-5-yl]-4-(trifluoromethyl)benzamide;
N-[3-[4-[2-hydroxyethyl(methyl)amino]-2-pyridyl]-1,2,4-thiadiazol-5-yl]-4-(trifluoromethyl)benzamide;
N-[3-[4-[2-(1-piperidyl)ethoxy]-2-pyridyl]-1,2,4-thiadiazol-5-yl]-4-(trifluoromethyl)benzamide;
N-[3-[4-(2-methoxyethoxy)-2-pyridyl]-1,2,4-thiadiazol-5-yl]-4-(trifluoromethyl)benzamide;
N-[3-[4-(2-dimethylaminoethyloxy)-2-pyridyl]-1,2,4-thiadiazol-5-yl]-4-(trifluoromethyl)benzamide;
N-[3-[4-(2,2-dimethylpropoxy)-2-pyridyl]-1,2,4-thiadiazol-5-yl]-4-(trifluoromethyl)benzamide;
N-[3-[4-[(1-methyl-4-piperidyl)oxy]-2-pyridyl]-1,2,4-thiadiazol-5-yl]-4-(trifluoromethyl)benzamide;
N-[3-(4-tetrahydropyran-4-yloxy-2-pyridyl)-1,2,4-thiadiazol-5-yl]-4-(trifluoromethyl)benzamide;
N-[3-[4-(oxetan-3-yloxy)-2-pyridyl]-1,2,4-thiadiazol-5-yl]-4-(trifluoromethyl)benzamide; and
N-[3-[4-(hydroxymethyl)-2-pyridyl]-1,2,4-thiadiazol-5-yl]-4-(trifluoromethyl)benzamide
or a pesticidally acceptable salt thereof.

9. The compound of claim 8, selected from the group consisting of:
1-(4-methoxyphenyl)-3-[3-(2-pyridyl)-1,2,4-thiadiazol-5-yl]urea;
1-(2-chlorophenyl)-3-[3-(2-pyridyl)-1,2,4-thiadiazol-5-yl]urea;
1-[3-(2-pyridyl)-1,2,4-thiadiazol-5-yl]-3-[4-(trifluoromethyl)phenyl]urea;
1-(3-methoxyphenyl)-3-[3-(2-pyridyl)-1,2,4-thiadiazol-5-yl]urea;
1-[3-(2-pyridyl)-1,2,4-thiadiazol-5-yl]-3-[4-(trifluoromethoxy)phenyl]urea;
1-[3-(2-pyridyl)-1,2,4-thiadiazol-5-yl]-3-[3-(trifluoromethyl)phenyl]urea;
4-chloro-N-[3-(2-pyridyl)-1,2,4-thiadiazol-5-yl]benzamide;
3-chloro-N-[3-(2-pyridyl)-1,2,4-thiadiazol-5-yl]benzamide;
4-cyano-N-[3-(2-pyridyl)-1,2,4-thiadiazol-5-yl]benzamide;
3-fluoro-N-[3-(2-pyridyl)-1,2,4-thiadiazol-5-yl]benzamide;
N-[3-(2-pyridyl)-1,2,4-thiadiazol-5-yl]-4-(trifluoromethyl)benzamide;
N-[3-(2-pyridyl)-1,2,4-thiadiazol-5-yl]naphthalene-2-carboxamide;
4-trifluoromethoxy-N-[3-(2-pyridyl)-1,2,4-thiadiazol-5-yl]benzamide;
4-chloro-N-[3-(2-pyridyl)-1,2,4-thiadiazol-5-yl]benzenesulfonamide;

2-chloro-N-[3-(2-pyridyl)-1,2,4-thiadiazol-5-yl]benzenesulfonamide;
4-cyano-N-[3-(2-pyridyl)-1,2,4-thiadiazol-5-yl]benzenesulfonamide;
4-methoxy-N-[3-(2-pyridyl)-1,2,4-thiadiazol-5-yl]benzenesulfonamide;
2-methoxy-N-[3-(2-pyridyl)-1,2,4-thiadiazol-5-yl]benzenesulfonamide;
N-[3-(2-pyridyl)-1,2,4-thiadiazol-5-yl]-3-(trifluoromethyl)benzenesulfonamide;
N-[3-(2-pyridyl)-1,2,4-thiadiazol-5-yl]-4-(trifluoromethyl)benzenesulfonamide;
N-[3-(3-fluoro-2-pyridyl)-1,2,4-thiadiazol-5-yl]-4-(trifluoromethyl)benzamide;
N-[3-(4-morpholino-2-pyridyl)-1,2,4-thiadiazol-5-yl]-4-(trifluoromethyl)benzamide;
N-[3-[4-[benzyl(methyl)amino]-2-pyridyl]-1,2,4-thiadiazol-5-yl]-4-(trifluoromethyl)benzamide;
N-[3-[4-(dimethylamino)-2-pyridyl]-1,2,4-thiadiazol-5-yl]-4-(trifluoromethyl)benzamide;
N-[3-[4-[2-methoxyethyl(methyl)amino]-2-pyridyl]-1,2,4-thiadiazol-5-yl]-4-(trifluoromethyl)benzamide;
N-[3-(5-methoxy-2-pyridyl)-1,2,4-thiadiazol-5-yl]-4-(trifluoromethyl)benzamide;
N-[3-(4-methoxy-2-pyridyl)-1,2,4-thiadiazol-5-yl]-4-(trifluoromethyl)benzamide;
N-[3-[4-(triazolo[4,5-b]-pyridin-3-yloxy)-2-pyridyl]-1,2,4-thiadiazol-5-yl]-4-(trifluoromethyl)benzamide;
N-[3-(5-bromo-2-pyridyl)-1,2,4-thiadiazol-5-yl]-4-(trifluoromethyl)benzamide;
methyl 2-[5-[[4-(trifluoromethyl)benzoyl]amino]-1,2,4-thiadiazol-3-yl]pyridine-4-carboxylate;
N-[3-(2-pyridyl)-1,2,4-thiadiazol-5-yl]isoquinoline-7-carboxamide;
4-acetamido-N-[3-(2-pyridyl)-1,2,4-thiadiazol-5-yl]benzamide;
4-fluoro-N-[3-(2-pyridyl)-1,2,4-thiadiazol-5-yl]benzamide;
4-nitro-N-[3-(2-pyridyl)-1,2,4-thiadiazol-5-yl]benzamide;
N-[3-(2-pyridyl)-1,2,4-thiadiazol-5-yl]-quinoxaline-6-carboxamide;
N-[3-(2-pyridyl)-1,2,4-thiadiazol-5-yl]thiophene-2-carboxamide;
N-[3-(2-pyridyl)-1,2,4-thiadiazol-5-yl]thiophene-3-carboxamide;
N-[3-(4-isopropyl-2-pyridyl)-1,2,4-thiadiazol-5-yl]-4-(trifluoromethyl)benzamide;
N-[3-(3-isoquinolyl)-1,2,4-thiadiazol-5-yl]-4-(trifluoromethyl)benzamide;
N-[3-(5-fluoro-2-pyridyl)-1,2,4-thiadiazol-5-yl]-4-(trifluoromethyl)benzamide;
N-[3-(5-methyl-2-pyridyl)-1,2,4-thiadiazol-5-yl]-4-(trifluoromethyl)benzamide;
3-chloro-4-fluoro-N-[3-(5-fluoro-2-pyridyl)-1,2,4-thiadiazol-5-yl]benzamide;
N-[3-(5-fluoro-2-pyridyl)-1,2,4-thiadiazol-5-yl]-4-(trifluoromethoxy)benzamide;
4-tert-butyl-N-[3-(5-fluoro-2-pyridyl)-1,2,4-thiadiazol-5-yl]benzamide;
N-[3-(5-fluoro-2-pyridyl)-1,2,4-thiadiazol-5-yl]-3,5-bis(trifluoromethyl)benzamide;
N-[3-(5-fluoro-2-pyridyl)-1,2,4-thiadiazol-5-yl]-3-(trifluoromethyl)benzamide;
3,4-dichloro-N-[3-(5-fluoro-2-pyridyl)-1,2,4-thiadiazol-5-yl]benzamide;
N-[3-(2-pyridyl)-1,2,4-thiadiazol-5-yl]isoquinoline-5-carboxamide;
3-chloro-4-(4-methylpiperazin-1-yl)-N-[3-(2-pyridyl)-1,2,4-thiadiazol-5-yl]benzamide;
methyl 4-[[3-(2-pyridyl)-1,2,4-thiadiazol-5-yl]carbamoyl]benzoate;
4-(diethylsulfamoyl)-N-[3-(2-pyridyl)-1,2,4-thiadiazol-5-yl]benzamide;
4-methyl-N-[3-(2-pyridyl)-1,2,4-thiadiazol-5-yl]thiophene-2-carboxamide;
3-chloro-4-fluoro-N-[3-(2-pyridyl)-1,2,4-thiadiazol-5-yl]benzamide;
2-fluoro-3-methoxy-N-[3-(2-pyridyl)-1,2,4-thiadiazol-5-yl]benzamide;
N-[3-(2-pyridyl)-1,2,4-thiadiazol-5-yl]-3-(trifluoromethyl)benzamide;
2,5-dimethyl-N-[3-(2-pyridyl)-1,2,4-thiadiazol-5-yl]furan-3-carboxamide;
4-tert-butyl-N-[3-(2-pyridyl)-1,2,4-thiadiazol-5-yl]benzamide;
N-[3-(2-pyridyl)-1,2,4-thiadiazol-5-yl]-1,3-benzodioxole-5-carboxamide;
3,4-dichloro-N-[3-(2-pyridyl)-1,2,4-thiadiazol-5-yl]benzamide;
N-[3-(2-pyridyl)-1,2,4-thiadiazol-5-yl]-3,5-bis(trifluoromethyl)benzamide;
4-methoxy-N-[3-(2-pyridyl)-1,2,4-thiadiazol-5-yl]benzamide;
4-phenoxy-N-[3-(2-pyridyl)-1,2,4-thiadiazol-5-yl]benzamide;
4-fluoro-N-[3-(2-pyridyl)-1,2,4-thiadiazol-5-yl]-2-(trifluoromethyl)benzamide;
N-[3-(2-pyridyl)-1,2,4-thiadiazol-5-yl]benzamide;
4-iodo-N-[3-(2-pyridyl)-1,2,4-thiadiazol-5-yl]benzamide;
tert-butyl 4-[4-[[3-(2-pyridyl)-1,2,4-thiadiazol-5-yl]carbamoyl]benzoyl]piperazine-1-carboxylate;
4-(piperidine-1-carbonyl)-N-[3-(2-pyridyl)-1,2,4-thiadiazol-5-yl]benzamide;
N1-[3-(2-pyridyl)-1,2,4-thiadiazol-5-yl]terephthalamide;
4-(2-pyridylamino)-N-[3-(2-pyridyl)-1,2,4-thiadiazol-5-yl]benzamide;
tert-butyl 4-[4-[[3-(2-pyridyl)-1,2,4-thiadiazol-5-yl]carbamoyl]anilino]piperidine-1-carboxylate;
4-phenyl-N-[3-(2-pyridyl)-1,2,4-thiadiazol-5-yl]benzamide;
4-(4-piperidylamino)-N-[3-(2-pyridyl)-1,2,4-thiadiazol-5-yl]benzamide;
4-benzyl-N-[3-(2-pyridyl)-1,2,4-thiadiazol-5-yl]benzamide;
4-bromo-N-[3-(2-pyridyl)-1,2,4-thiadiazol-5-yl]benzamide;
3-chloro-N-[3-(2-pyridyl)-1,2,4-thiadiazol-5-yl](trifluoromethoxy)benzamide;
N-[3-(4-phenyl-2-pyridyl)-1,2,4-thiadiazol-5-yl]-4-(trifluoromethyl)benzamide;
4-(trifluoromethyl)-N-[3-[5-(trifluoromethyl)-2-pyridyl]-1,2,4-thiadiazol-5-yl]benzamide;
N-[3-(2-pyridyl)-1,2,4-thiadiazol-5-yl]-2-(trifluoromethyl)benzamide;
2-fluoro-N-[3-(2-pyridyl)-1,2,4-thiadiazol-5-yl](trifluoromethoxy)benzamide;
N-[3-(2-pyridyl)-1,2,4-thiadiazol-5-yl]-2-(trifluoromethoxy)benzamide;
N-[3-(2-pyridyl)-1,2,4-thiadiazol-5-yl]-3-(trifluoromethoxy)benzamide;

4-(4-fluorophenoxy)-N-[3-(2-pyridyl)-1,2,4-thiadiazol-5-yl]benzamide;

3-hydroxy-N-[3-(2-pyridyl)-1,2,4-thiadiazol-5-yl]-5-(trifluoromethyl)thiophene-2-carboxamide;

4-(2,4-difluorophenoxy)-N-[3-(2-pyridyl)-1,2,4-thiadiazol-5-yl]benzamide;

N-[3-(2-pyridyl)-1,2,4-thiadiazol-5-yl]-4-[4-(trifluoromethyl)phenoxy]benzamide;

N-[3-(2-pyridyl)-1,2,4-thiadiazol-5-yl]-3-[4-(trifluoromethyl)phenoxy]benzamide;

3-(4-fluorophenoxy)-N-[3-(2-pyridyl)-1,2,4-thiadiazol-5-yl]benzamide;

3-phenoxy-N-[3-(2-pyridyl)-1,2,4-thiadiazol-5-yl]benzamide;

4-(3-pyridyl)-N-[3-(2-pyridyl)-1,2,4-thiadiazol-5-yl]benzamide;

N-[3-(5-phenyl-2-pyridyl)-1,2,4-thiadiazol-5-yl]-4-(trifluoromethyl)benzamide;

4-(trifluoromethyl)-N-[3-(5-vinyl-2-pyridyl)-1,2,4-thiadiazol-5-yl]benzamide;

N-[3-[5-(3,6-dihydro-2H-pyran-4-yl)-2-pyridyl]-1,2,4-thiadiazol-5-yl]-4-(trifluoromethyl)benzamide;

N-[3-[6-(3-pyridyl)-2-pyridyl]-1,2,4-thiadiazol-5-yl]-4-(trifluoromethyl)benzamide;

4-(benzylamino)-N-[3-(2-pyridyl)-1,2,4-thiadiazol-5-yl]benzamide;

3-anilino-N-[3-(2-pyridyl)-1,2,4-thiadiazol-5-yl]benzamide;

N-[3-(5-morpholino-2-pyridyl)-1,2,4-thiadiazol-5-yl]-4-(trifluoromethyl)benzamide;

N-[3-[5-[2-methoxyethyl(methyl)amino]-2-pyridyl]-1,2,4-thiadiazol-5-yl]-4-(trifluoromethyl)benzamide;

N-[3-(5-pyrrolidin-1-yl-2-pyridyl)-1,2,4-thiadiazol-5-yl]-4-(trifluoromethyl)benzamide;

N-[3-[5-(2-pyridylamino)-2-pyridyl]-1,2,4-thiadiazol-5-yl]-4-(trifluoromethyl)benzamide;

N-[3-[5-(4-methylpiperazin-1-yl)-2-pyridyl]-1,2,4-thiadiazol-5-yl]-4-(trifluoromethyl)benzamide;

tert-butyl 4-[6-[5-[[4-(trifluoromethyl)benzoyl]amino]-1,2,4-thiadiazol-3-yl]-3-pyridyl]piperazine-1-carboxylate;

N-[3-[5-(1-piperidyl)-2-pyridyl]-1,2,4-thiadiazol-5-yl]-4-(trifluoromethyl)benzamide;

N-[3-(5-anilino-2-pyridyl)-1,2,4-thiadiazol-5-yl]-4-(trifluoromethyl)benzamide;

N-[3-[5-(4-hydroxy-1-piperidyl)-2-pyridyl]-1,2,4-thiadiazol-5-yl]-4-(trifluoromethyl)benzamide;

tert-butyl 4-[6-[5-[[4-(trifluoromethyl)benzoyl]amino]-1,2,4-thiadiazol-3-yl]-2-pyridyl]piperazine-1-carboxylate;

N-[3-(4-Methyl-2-pyridyl)-1,2,4-thiadiazol-5-yl]-4-(trifluoromethyl)benzamide;

N-[3-(6-Methyl-2-pyridyl)-1,2,4-thiadiazol-5-yl]-4-(trifluoromethyl)benzamide;

N-[3-[4-(dimethylaminomethyl)-2-pyridyl]-1,2,4-thiadiazol-5-yl]-4-(trifluoromethyl)benzamide;

N-[3-[4-[methyl-[2-(1-piperidyl)ethyl]amino]-2-pyridyl]-1,2,4-thiadiazol-5-yl]-4-(trifluoromethyl)benzamide;

N-[3-[4-[methyl(2-morpholinoethyl)amino]-2-pyridyl]-1,2,4-thiadiazol-5-yl]-4-(trifluoromethyl)benzamide;

N-[3-(4-pyrrolidin-1-yl-2-pyridyl)-1,2,4-thiadiazol-5-yl]-4-(trifluoromethyl)benzamide;

N-[3-[4-(4-methylpiperazin-1-yl)-2-pyridyl]-1,2,4-thiadiazol-5-yl]-4-(trifluoromethyl)benzamide;

N-[3-[4-[2-hydroxyethyl(methyl)amino]-2-pyridyl]-1,2,4-thiadiazol-5-yl]-4-(trifluoromethyl)benzamide;

N-[3-[4-[2-(1-piperidyl)ethoxy]-2-pyridyl]-1,2,4-thiadiazol-5-yl]-4-(trifluoromethyl)benzamide;

N-[3-[4-(2-methoxyethoxy)-2-pyridyl]-1,2,4-thiadiazol-5-yl]-4-(trifluoromethyl)benzamide;

N-[3-[4-(2,2-dimethylpropoxy)-2-pyridyl]-1,2,4-thiadiazol-5-yl]-4-(trifluoromethyl)benzamide;

N-[3-(4-tetrahydropyran-4-yloxy-2-pyridyl)-1,2,4-thiadiazol-5-yl]-4-(trifluoromethyl)benzamide;

N-[3-[4-(oxetan-3-yloxy)-2-pyridyl]-1,2,4-thiadiazol-5-yl]-4-(trifluoromethyl)benzamide; and N-[3-[4-(hydroxymethyl)-2-pyridyl]-1,2,4-thiadiazol-5-yl]-4-(trifluoromethyl)benzamide;

or a pesticidally acceptable salt thereof.

10. A pesticidal composition comprising a compound of claim 1 and a pesticidally acceptable carrier.

11. The compound of claim 1 further comprising one or more other pesticidally active substances in combination.

12. A method of manufacturing a compound of formula (I) of claim 1 in which X is $R^1$, comprising reacting a compound of formula (II):

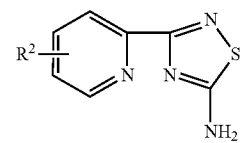

wherein $R^2$ is as defined in claim 1, with a compound of formula (III):

(III)

wherein $R^1$ and A are as defined in claim 1 and $X^1$ is a leaving group.

13. The composition of claim 10 further comprising one or more other pesticidally active substances.

* * * * *